(12) United States Patent
Dai

(10) Patent No.: US 7,931,371 B2
(45) Date of Patent: Apr. 26, 2011

(54) SYSTEMS AND METHODS FOR WAVEFRONT RECONSTRUCTION FOR APERTURE WITH ARBITRARY SHAPE

(75) Inventor: Guangming Dai, Fremont, CA (US)

(73) Assignee: AMO Manufacturing USA, LLC., Santa Ana, CA (US)

(*) Notice: Subject to any disclaimer, the term of this patent is extended or adjusted under 35 U.S.C. 154(b) by 0 days.

(21) Appl. No.: 12/793,348

(22) Filed: Jun. 3, 2010

(65) Prior Publication Data
US 2010/0238407 A1 Sep. 23, 2010

Related U.S. Application Data

(63) Continuation of application No. 11/690,409, filed on Mar. 23, 2007, now Pat. No. 7,780,294.

(60) Provisional application No. 60/785,967, filed on Mar. 23, 2006.

(51) Int. Cl.
*A61B 3/10* (2006.01)
(52) U.S. Cl. .......................................... 351/212; 351/200
(58) Field of Classification Search .................. 351/212
See application file for complete search history.

(56) References Cited

U.S. PATENT DOCUMENTS

| | | |
|---|---|---|
| 3,936,160 A | 2/1976 | Von Bieren |
| 4,665,913 A | 5/1987 | L'Esperance, Jr. |
| 5,144,630 A | 9/1992 | Lin |
| 5,220,360 A | 6/1993 | Verdooner et al. |
| 5,233,517 A | 8/1993 | Jindra |
| 5,520,679 A | 5/1996 | Lin |
| 5,646,791 A | 7/1997 | Glockler |
| 5,683,379 A | 11/1997 | Hohla |
| 5,713,892 A | 2/1998 | Shimmick |
| 5,737,059 A | 4/1998 | Tanaka |
| 5,742,626 A | 4/1998 | Mead et al. |
| 5,745,309 A | 4/1998 | Salmon |
| 5,777,719 A | 7/1998 | Williams et al. |
| 5,782,822 A | 7/1998 | Telfair et al. |
| 5,818,957 A | 10/1998 | Mammone |
| 5,936,720 A | 8/1999 | Neal et al. |
| 6,004,313 A | 12/1999 | Shimmick et al. |
| 6,090,102 A | 7/2000 | Telfair et al. |

(Continued)

FOREIGN PATENT DOCUMENTS

WO  WO 92/01417  2/1992

(Continued)

OTHER PUBLICATIONS

Guirao, Antonio et al., "*Corneal wave aberration from videokeratography: Accuracy and limitations of the procedure,*" J. Opt. Soc. Am. A, vol. 17, No. 6, Jun. 2000, pp. 955-965.

(Continued)

*Primary Examiner* — Jordan M. Schwartz
*Assistant Examiner* — James C Jones

(57) ABSTRACT

Systems, methods, and devices for determining an aberration in an optical tissue system of an eye are provided. Techniques include inputting optical data from the optical tissue system of the eye, where the optical data includes set of local gradients corresponding to a non-circular shaped aperture, processing the optical data with an iterative Fourier transform to obtain a set of Fourier coefficients, converting the set of Fourier coefficients to a set of modified Zernike coefficients that are orthogonal over the non-circular shaped aperture, and determining the aberration in the optical tissue system of the eye based on the set of modified Zernike coefficients.

20 Claims, 27 Drawing Sheets

U.S. PATENT DOCUMENTS

| | | | |
|---|---|---|---|
| 6,095,651 | A | 8/2000 | Williams et al. |
| 6,130,419 | A | 10/2000 | Neal |
| 6,184,974 | B1 | 2/2001 | Neal et al. |
| 6,199,986 | B1 | 3/2001 | Williams et al. |
| 6,271,915 | B1 | 8/2001 | Frey et al. |
| 6,299,311 | B1 | 10/2001 | Williams et al. |
| 6,331,059 | B1 | 12/2001 | Kudryashov et al. |
| 6,460,997 | B1 | 10/2002 | Frey et al. |
| 6,595,642 | B2 | 7/2003 | Wirth |
| 6,607,274 | B2 | 8/2003 | Stantz et al. |
| 6,634,750 | B2 | 10/2003 | Neal et al. |
| 6,659,613 | B2 | 12/2003 | Applegate et al. |
| 6,738,511 | B1 | 5/2004 | Farrell et al. |
| 6,924,899 | B2 | 8/2005 | Hutchin et al. |
| 7,168,807 | B2 | 1/2007 | Chernyak et al. |
| 7,175,278 | B2 | 2/2007 | Chernyak et al. |
| 7,780,294 | B2 | 8/2010 | Dai |
| 2001/0041884 | A1 | 11/2001 | Frey et al. |
| 2002/0027640 | A1 | 3/2002 | Campin |
| 2002/0097376 | A1 | 7/2002 | Applegate et al. |
| 2002/0097377 | A1 | 7/2002 | Kudryashov et al. |
| 2002/0135736 | A1 | 9/2002 | Stark et al. |
| 2005/0012898 | A1 | 1/2005 | Chernyak et al. |
| 2007/0058132 | A1 | 3/2007 | Dai |
| 2008/0212031 | A1 | 9/2008 | Chernyak et al. |
| 2009/0036980 | A1* | 2/2009 | Norrby et al. ............ 623/5.11 |

FOREIGN PATENT DOCUMENTS

| | | |
|---|---|---|
| WO | WO 02/19901 | 2/2002 |
| WO | WO 02/30273 | 4/2002 |
| WO | WO 2007/027674 A | 3/2007 |

OTHER PUBLICATIONS

Hamam, Habib "*A Quick Method for Analyzing Hartmann-Shack Patterns: Application to Refractive Surgery*" Journal of Refractive Surgery, vol. 16, Sep./Oct. 2000, pp. S636-S642.

Ishkander et al., "*An Alternative Polynomial Representation of the Wavefront Error Function*," Invest Ophthalmol Vis Sci 2002;43: E-Abstract, downloaded on Nov. 19, 2004 from http://abstracts.iovs.org/cgi/content/abstract/43/12/1898?maxtoshow=&HITS=10&RESUTLF, 1 page.

Ishkander et al., "*Modeling of Corneal Surfaces With Radial Polynomials*," IEEE Transactions on Biomedical Engineering, vol. 49, No. 4, Apr. 2002, pp. 320-328.

Klein, Stanley A. et al., "*Line of Sight and Alternative Representations of Aberrations of the Eye*" Journal of Refractive Surgery, vol. 16, Sep./Oct. 2000, pp. S630-S635.

Liang et al., In "*Objective Measurement of Wave Aberrations of the Human Eye with the Use of a Harman-Shack Wave-front Sensor,*" Journal Optical Society of America, Jul. 1994, vol. 11, No. 7, pp. 1949-1957.

*Notice of Erroneous Posting of Application Information on Sep. 1, 2005.* U.S. Appl. No. 10/032,469, United States Patent and Trademark Office (Oct. 11, 2005), 2 pages.

Roddier, Francois et al., "*Wavefront reconstruction using iterative Fourier transforms*," Applied Optics, vol. 30, No. 11, Apr. 10, 1991, pp. 1325-1327.

Schweigerling, Jim et al.., "*Using Corneal Height Maps and Polynomial Decomposition to Determine Corneal Aberrations,*" Optometry and Vision Science, vol. 74, No. 11, Nov. 1997, pp. 906-916.

Thibos, Larry N., "*Wavefront Data Reporting and Terminology*" Journal of Refractive Surgery, vol. 17 Sep./Oct. 2001, pp. S578-S583.

Upton, R. et al., "*Gram-Schmidt orthogonalization of the Zernike polynomial of apertures of arbitrary shape,*" Opt. Lett. 29 (2004), pp. 2840-2842.

Noll, R.J., "*Aernike polynomials and atmospheric turbulence,*" J. Opt. Soc. Am. 66 (1976), pp. 207-211.

Mahajan, V.N., "*Zernike polynomials and aberration balancing,*" SPIE Proc., vol. 5173 (2003), pp. 1-17.

Dai, G., "Zernike Abberation Coefficients Transformed To and From Fourier Series Coefficients for Wavefront Representation," Optics Letters, OSA, Optical Society America, Washington, DC, vol. 31, No. 4, Feb. 15, 2006, pp. 501-503.

* cited by examiner

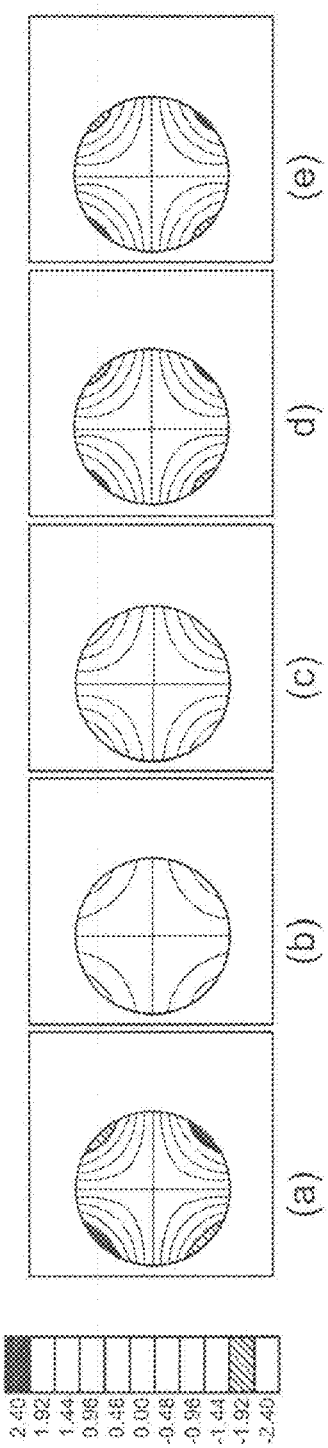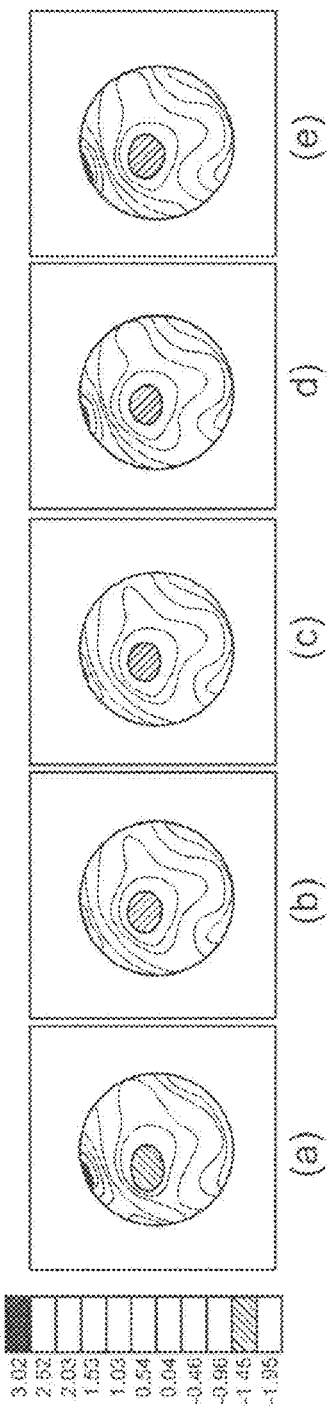
FIG. 13
FIG. 14

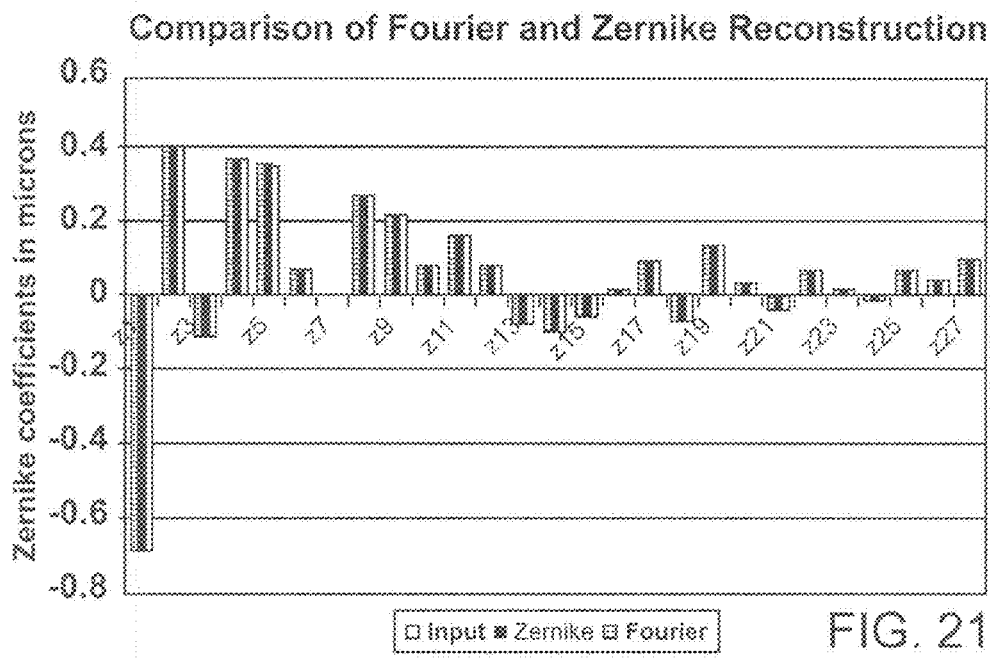
FIG. 21
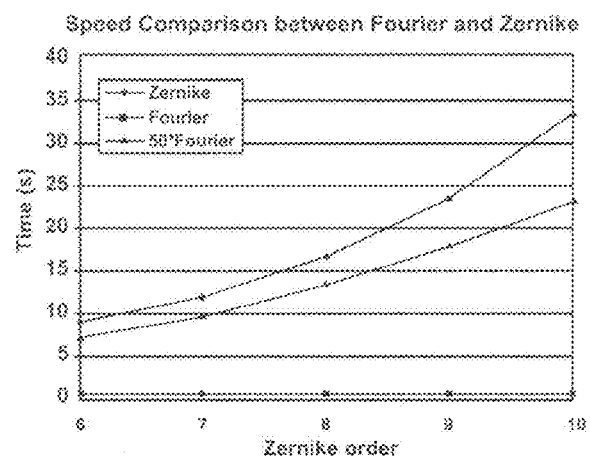
FIG. 22
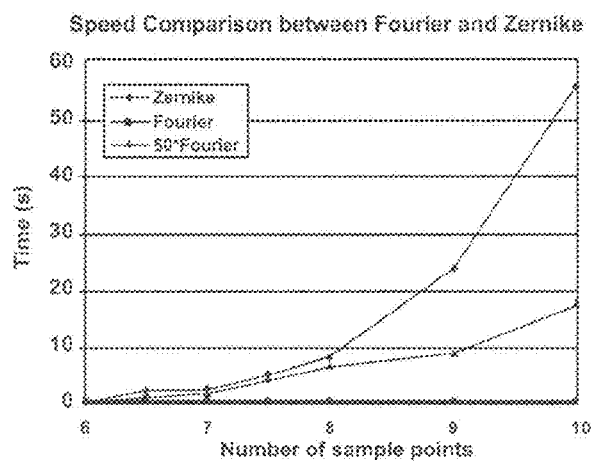

SYSTEMS AND METHODS FOR WAVEFRONT RECONSTRUCTION FOR APERTURE WITH ARBITRARY SHAPE

CROSS-REFERENCES TO RELATED APPLICATIONS

This application is a continuation of U.S. patent application Ser. No. 11/690,409 filed Mar. 23, 2007, which claims the benefit of U.S. Patent Application No. 60/785,967 filed Mar. 23, 2006. This application is also related to U.S. patent application Ser. No. 10/601,048 filed Jun. 20, 2003, U.S. patent application Ser. No. 10/872,107 filed Jun. 17, 2004, and U.S. patent application Ser. No. 11/218,833 filed Sep. 2, 2005. The entire content of each of these applications is incorporated herein by reference for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention generally relates to measuring optical errors of optical systems. More particularly, the invention relates to improved methods and systems for determining an optical surface model for an optical tissue system of an eye, to improved methods and systems for reconstructing a wavefront surface/elevation map of optical tissues of an eye, and to improved systems for calculating an ablation pattern.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, and the like.

Known corneal correction treatment methods have generally been successful in correcting standard vision errors, such as myopia, hyperopia, astigmatism, and the like. However, as with all successes, still further improvements would be desirable. Toward that end, wavefront measurement systems are now available to accurately measure the refractive characteristics of a particular patient's eye. One exemplary wavefront technology system is the VISX WaveScan® System, which uses a Hartmann-Shack wavefront lenslet array that can quantify aberrations throughout the entire optical system of the patient's eye, including first- and second-order sphero-cylindrical errors, coma, and third and fourth-order aberrations related to coma, astigmatism, and spherical aberrations.

Wavefront measurement of the eye may be used to create an ocular aberration map, a high order aberration map, or wavefront elevation map that permits assessment of aberrations throughout the optical pathway of the eye, e.g., both internal aberrations and aberrations on the corneal surface. The aberration map may then be used to compute a custom ablation pattern for allowing a surgical laser system to correct the complex aberrations in and on the patient's eye. Known methods for calculation of a customized ablation pattern using wavefront sensor data generally involve mathematically modeling an optical surface of the eye using expansion series techniques.

Reconstruction of the wavefront or optical path difference (OPD) of the human ocular aberrations can be beneficial for a variety of uses. For example, the wavefront map, the wavefront refraction, the point spread function, and the treatment table can all depend on the reconstructed wavefront.

Known wavefront reconstruction can be categorized into two approaches: zonal reconstruction and modal reconstruction. Zonal reconstruction was used in early adaptive optics systems. More recently, modal reconstruction has become popular because of the use of Zernike polynomials. Coefficients of the Zernike polynomials can be derived through known fitting techniques, and the refractive correction procedure can be determined using the shape of the optical surface of the eye, as indicated by the mathematical series expansion model.

Conventional Zernike function methods of surface reconstruction and their accuracy for normal eyes have limits. For example, 6th order Zernike polynomials may not accurately represent an actual wavefront in all circumstances. The discrepancy may be most significant for eyes with a keratoconus condition. Known Zernike polynomial modeling methods may also result in errors or "noise" which can lead to a less than ideal refractive correction. Furthermore, the known surface modeling techniques are somewhat indirect, and may lead to unnecessary errors in calculation, as well as a lack of understanding of the physical correction to be performed.

Therefore, in light of above, it would be desirable to provide improved methods and systems for mathematically modeling optical tissues of an eye.

BRIEF SUMMARY OF THE INVENTION

The present invention provides novel methods and systems for determining an optical surface model. What is more, the present invention provides systems, software, and methods for measuring errors and reconstructing wavefront elevation maps in an optical system and for determining opthalmological prescription shapes.

In a first aspect, the present invention provides a method of determining an optical surface model for an optical tissue system of an eye. The method can include inputting a Fourier transform of optical data from the optical tissue system, inputting a conjugate Fourier transform of a basis function surface, determining a Fourier domain sum of the Fourier transform and the conjugate Fourier transform, calculating an estimated basis function coefficient based on the Fourier domain sum, and determining the optical surface model based on the estimated basis function coefficient. The Fourier transform can include an iterative Fourier transform. The basis function surface can include a Zernike polynomial surface and the estimated basis function coefficient can include an estimated Zernike polynomial coefficient. In some aspects, the estimated Zernike polynomial coefficient includes a member selected from the group consisting of a low order aberration term and a high order aberration term. Relatedly, the estimated Zernike polynomial coefficient can include a member selected from the group consisting of a sphere term, a cylinder term, a coma term, and a spherical aberration term. In some aspects, the basis function surface can include a Fourier series surface and the estimated basis function coefficient can include an estimated Fourier series coefficient. In another aspect, the basis function surface can include a Taylor monomial surface and the estimated basis function coefficient can include an estimated Taylor monomial coefficient. In some aspects, the optical data is derived from a wavefront map of the optical system. In some aspects, the optical data can include nondiscrete data. Relatedly, the optical data can include a set of N×N discrete grid points, and the Fourier transform and the conjugate transform can be in a numerical format. In another aspect, the optical data can include a set of N×N discrete grid points, and the Fourier transform and the conjugate transform can be in an analytical format. Relatedly, a y-axis separation distance between each neighboring grid point can be 0.5 and an x-axis separation distance between each neighboring grid point can be 0.5.

In one aspect, the present invention provides a system for calculating an estimated basis function coefficient for an optical tissue system of an eye. The system can include a light source for transmitting an image through the optical tissue system, a sensor oriented for determining a set of local gradients for the optical tissue system by detecting the transmitted image, a processor coupled with the sensor, and a memory coupled with the processor, where the memory is configured to store a plurality of code modules for execution by the processor. The plurality of code modules can include a module for inputting a Fourier transform of the set of local gradients for the optical tissue system, a module for inputting a conjugate Fourier transform of a basis function surface, a module for determining a Fourier domain sum of the Fourier transform and the conjugate Fourier transform, and a module for calculating the estimated basis function coefficient based on the Fourier domain sum. In a related aspect, the basis function surface can include a member selected from the group consisting of a Zernike polynomial surface, a Fourier series surface, and a Taylor monomial surface. In some embodiments, the optical tissue system of the eye can be represented by a two dimensional surface comprising a set of N×N discrete grid points, and the Fourier transform and the conjugate transform are can be a numerical format. In some aspects, optical tissue system of the eye can be represented by a two dimensional surface that includes a set of N×N discrete grid points, the Fourier transform and the conjugate transform can be in an analytical format, a y-axis separation distance between each neighboring grid point can be 0.5, and an x-axis separation distance between each neighboring grid point can be 0.5.

In another aspect, the present invention provides a method of calculating an estimated basis function coefficient for a two dimensional surface. The method can include inputting a Fourier transform of the two dimensional surface, inputting a conjugate Fourier transform of a basis function surface, determining a Fourier domain sum of the Fourier transform and the conjugate Fourier transform, and calculating the estimated basis function coefficient based on the Fourier domain sum. In some aspects, the basis function surface includes a member selected from the group consisting of an orthogonal basis function surface and a non-orthogonal basis function surface. In a related aspect, the two dimensional surface includes a set of N×N discrete grid points, and the Fourier transform and the conjugate transform are in a numerical format. Relatedly, the two dimensional surface can include a set of N×N discrete grid points, the Fourier transform and the conjugate transform can be in an analytical format, a y-axis separation distance between each neighboring grid point can be 0.5, and an x-axis separation distance between each neighboring grid point can be 0.5.

The methods and apparatuses of the present invention may be provided in one or more kits for such use. For example, the kits may comprise a system for determining an optical surface model that corresponds to an optical tissue system of an eye. Optionally, such kits may further include any of the other system components described in relation to the present invention and any other materials or items relevant to the present invention. The instructions for use can set forth any of the methods as described above. It is further understood that systems according to the present invention may be configured to carry out any of the method steps described herein.

In a further aspect, embodiments provide methods of determining an aberration in an optical tissue system of an eye. Methods can include inputting optical data from the optical tissue system of the eye, where the optical data comprising set of local gradients corresponding to a non-circular shaped aperture, processing the optical data with an iterative Fourier transform to obtain a set of Fourier coefficients, converting the set of Fourier coefficients to a set of modified Zernike coefficients that are orthogonal over the non-circular shaped aperture, and determining the aberration in the optical tissue system of the eye based on the set of modified Zernike coefficients. Embodiments may also provide systems for determining an aberration in an optical tissue system of an eye. Systems can include a light source for transmitting an image through the optical tissue system, a sensor oriented for determining a set of local gradients for the optical tissue system by detecting the transmitted image where the set of local gradients correspond to a non circular shaped aperture, a processor coupled with the sensor, and a memory coupled with the processor. The memory can be configured to store a plurality of code modules for execution by the processor, and the plurality of code modules can include a module for inputting optical data from the optical tissue system of the eye where the optical data includes the set of local gradients, a module for processing the optical data with an iterative Fourier transform to obtain a set of Fourier coefficients, a module for converting the set of Fourier coefficients to a set of modified Zernike coefficients that are orthogonal over the non-circular shaped aperture, and a module for determining the aberration in the optical tissue system of the eye based on the set of modified Zernike coefficients. Embodiments can also provide methods of determining an optical surface model for an optical tissue system of an eye. Methods can include inputting optical data from the optical tissue system of the eye where the optical data includes a set of local gradients corresponding to a non-circular shaped aperture, processing the optical data with an iterative Fourier transform to obtain a set of Fourier coefficients, deriving a reconstructed surface based on the set of Fourier coefficients, and determining the optical surface model based on the reconstructed surface. Methods can also include establishing a prescription shape for the eye based on the optical surface model.

For a fuller understanding of the nature and advantages of the present invention, reference should be had to the ensuing detailed description taken in conjunction with the accompanying drawings.

BRIEF DESCRIPTION OF THE DRAWINGS

FIG. 13 illustrates surface plots of wavefront reconstruction according to one embodiment of the present invention.

FIG. 14 illustrates surface plots of wavefront reconstruction according to one embodiment of the present invention.

FIG. 21 illustrates input and calculated output $6^{th}$ order Zernike coefficients using 2000 discrete points in a reconstruction with Fourier transform according to one embodiment of the present invention.

FIG. 22 illustrates speed comparisons between various algorithms according to one embodiment of the present invention.

DETAILED DESCRIPTION OF THE INVENTION

The present invention provides systems, software, and methods that can use high speed and accurate Fourier or iterative Fourier transformation algorithms to mathematically determine an optical surface model for an optical tissue system of an eye or to otherwise mathematically reconstruct optical tissues of an eye.

The present invention is generally useful for enhancing the accuracy and efficacy of laser eye surgical procedures, such as photorefractive keratectomy (PRK), photo therapeutic keratectomy (PTK), laser in situ keratomileusis (LASIK), and the like. The present invention can provide enhanced optical accuracy of refractive procedures by improving the methodology for measuring the optical errors of the eye and hence calculate a more accurate refractive ablation program. In one particular embodiment, the present invention is related to therapeutic wavefront-based ablations of pathological eyes.

The present invention can be readily adapted for use with existing laser systems, wavefront measurement systems, and other optical measurement devices. By providing a more direct (and hence, less prone to noise and other error) methodology for measuring and correcting errors of an optical system, the present invention may facilitate sculpting of the cornea so that treated eyes regularly exceed the normal 20/20 threshold of desired vision. While the systems, software, and methods of the present invention are described primarily in the context of a laser eye surgery system, it should be understood the present invention may be adapted for use in alternative eye treatment procedures and systems such as spectacle lenses, intraocular lenses, contact lenses, corneal ring implants, collagenous corneal tissue thermal remodeling, and the like.

Figure 1:
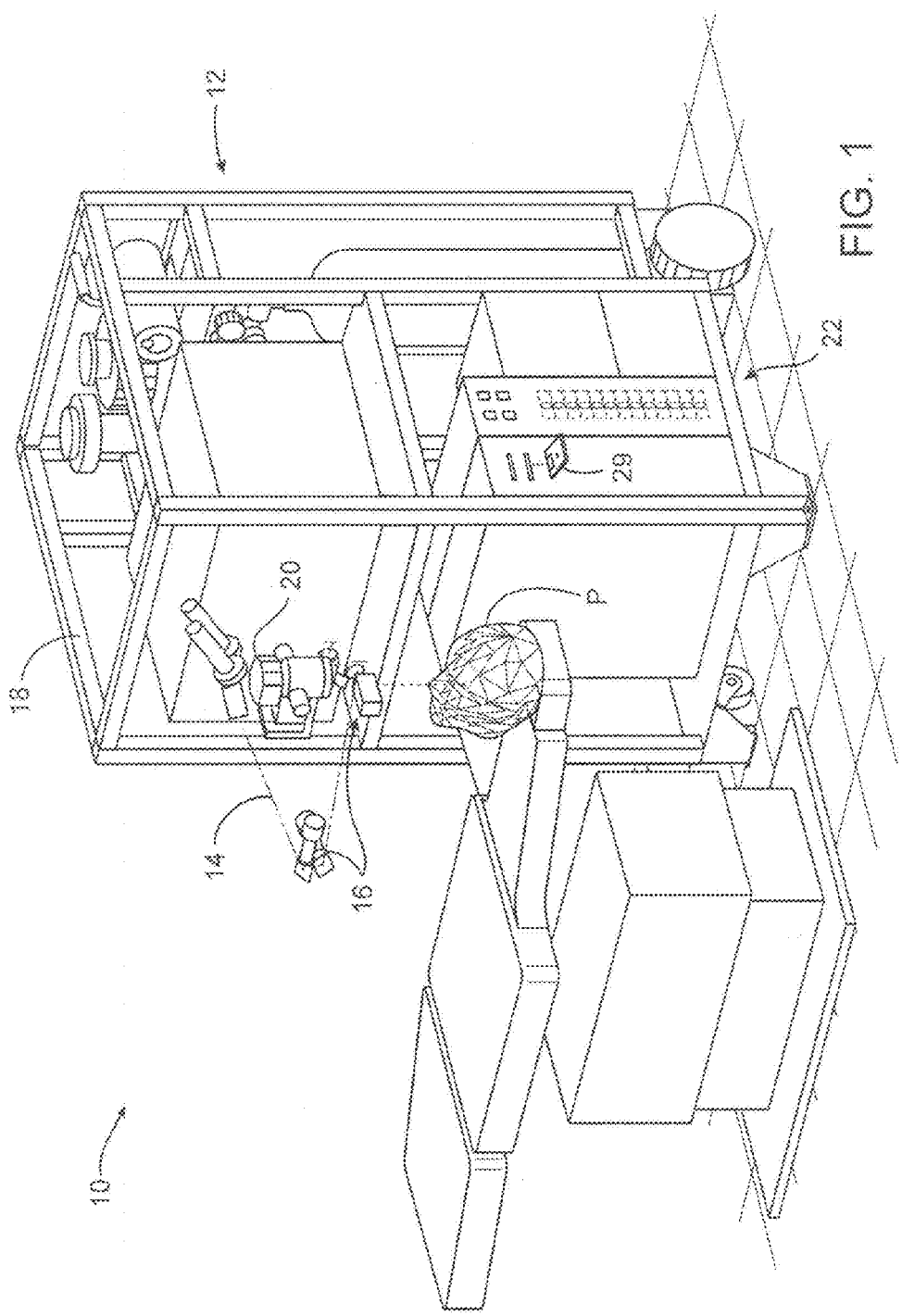
FIG. 1 illustrates a laser ablation system according to an embodiment of the present invention.

Referring now to FIG. 1, a laser eye surgery system 10 of the present invention includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of the eye.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via laser delivery optics 16. The present invention may also be useful with alternative sources of ultraviolet or infrared radiation, particularly those adapted to controllably ablate the corneal tissue without causing significant damage to adjacent and/or underlying tissues of the eye. In alternate embodiments, the laser beam source employs a solid state laser source having a wavelength between 193 and 215 nm as described in U.S. Pat. Nos. 5,520,679, and 5,144,630 to Lin and 5,742,626 to Mead, the full disclosures of which are incorporated herein by reference. In another embodiment, the laser source is an infrared laser as described in U.S. Pat. Nos. 5,782,822 and 6,090,102 to Telfair, the full disclosures of which are incorporated herein by reference. Hence, although an excimer laser is the illustrative source of an ablating beam, other lasers may be used in the present invention.

Laser 12 and laser delivery optics 16 will generally direct laser beam 14 to the eye of patient P under the direction of a computer system 22. Computer system 22 will often selectively adjust laser beam 14 to expose portions of the cornea to the pulses of laser energy so as to effect a predetermined sculpting of the cornea and alter the refractive characteristics of the eye. In many embodiments, both laser 12 and the laser delivery optical system 16 will be under control of computer system 22 to effect the desired laser sculpting process, with the computer system effecting (and optionally modifying) the pattern of laser pulses. The pattern of pulses may be summarized in machine readable data of tangible media 29 in the form of a treatment table, and the treatment table may be adjusted according to feedback input into computer system 22 from an automated image analysis system (or manually input into the processor by a system operator) in response to real-time feedback data provided from an ablation monitoring system feedback system. The laser treatment system 10, and computer system 22 may continue and/or terminate a sculpting treatment in response to the feedback, and may optionally also modify the planned sculpting based at least in part on the feedback.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like.

Figure 2:
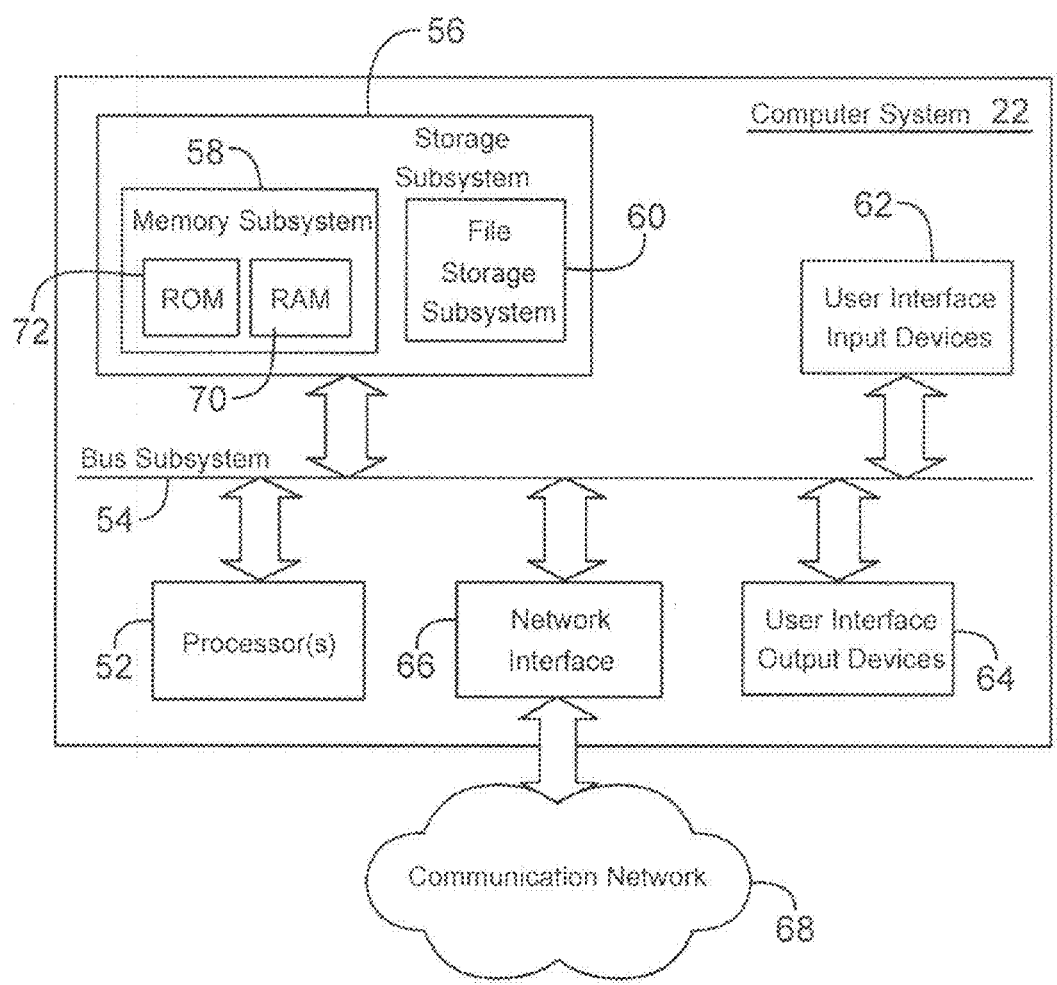
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 stores the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
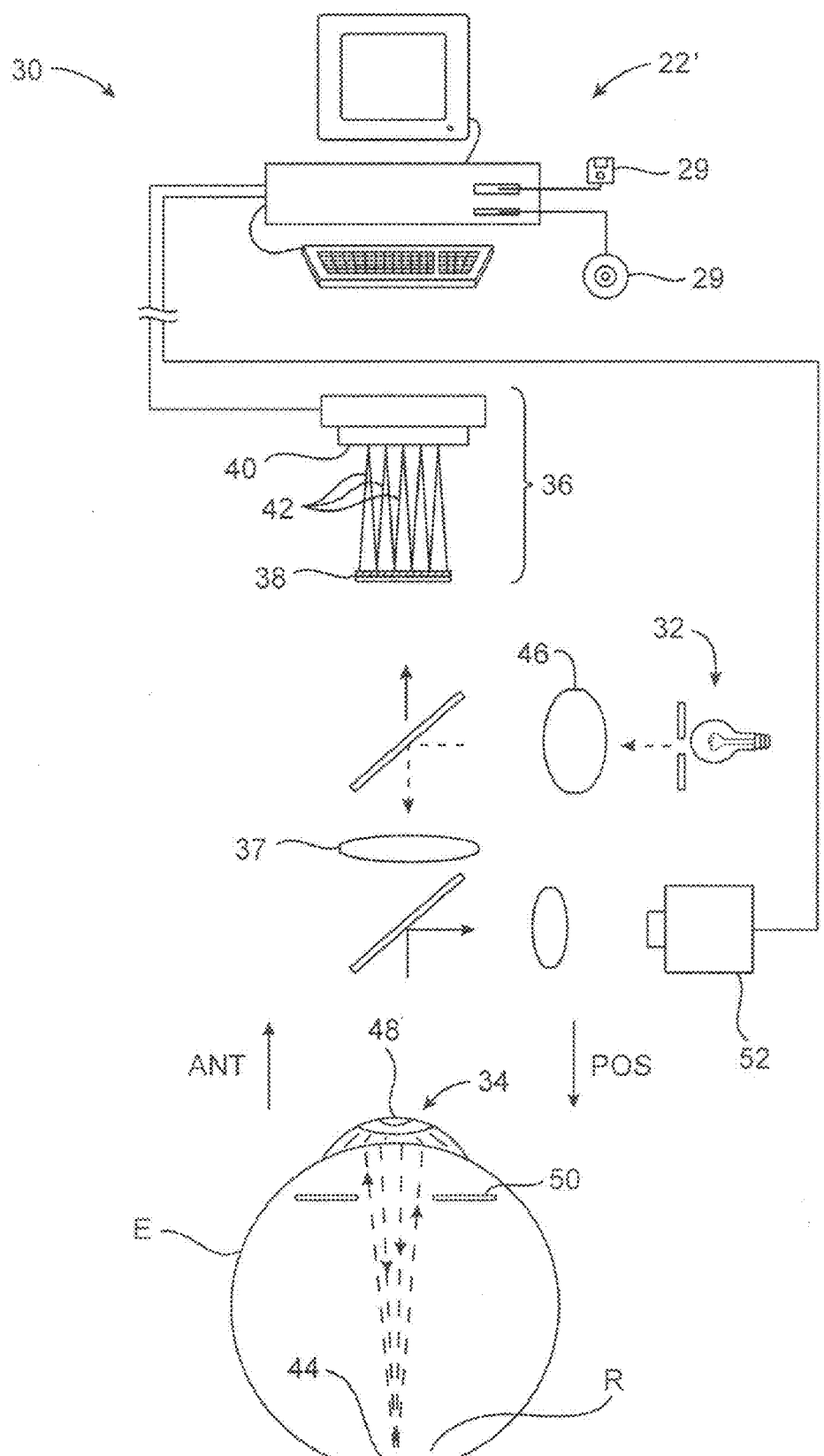
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
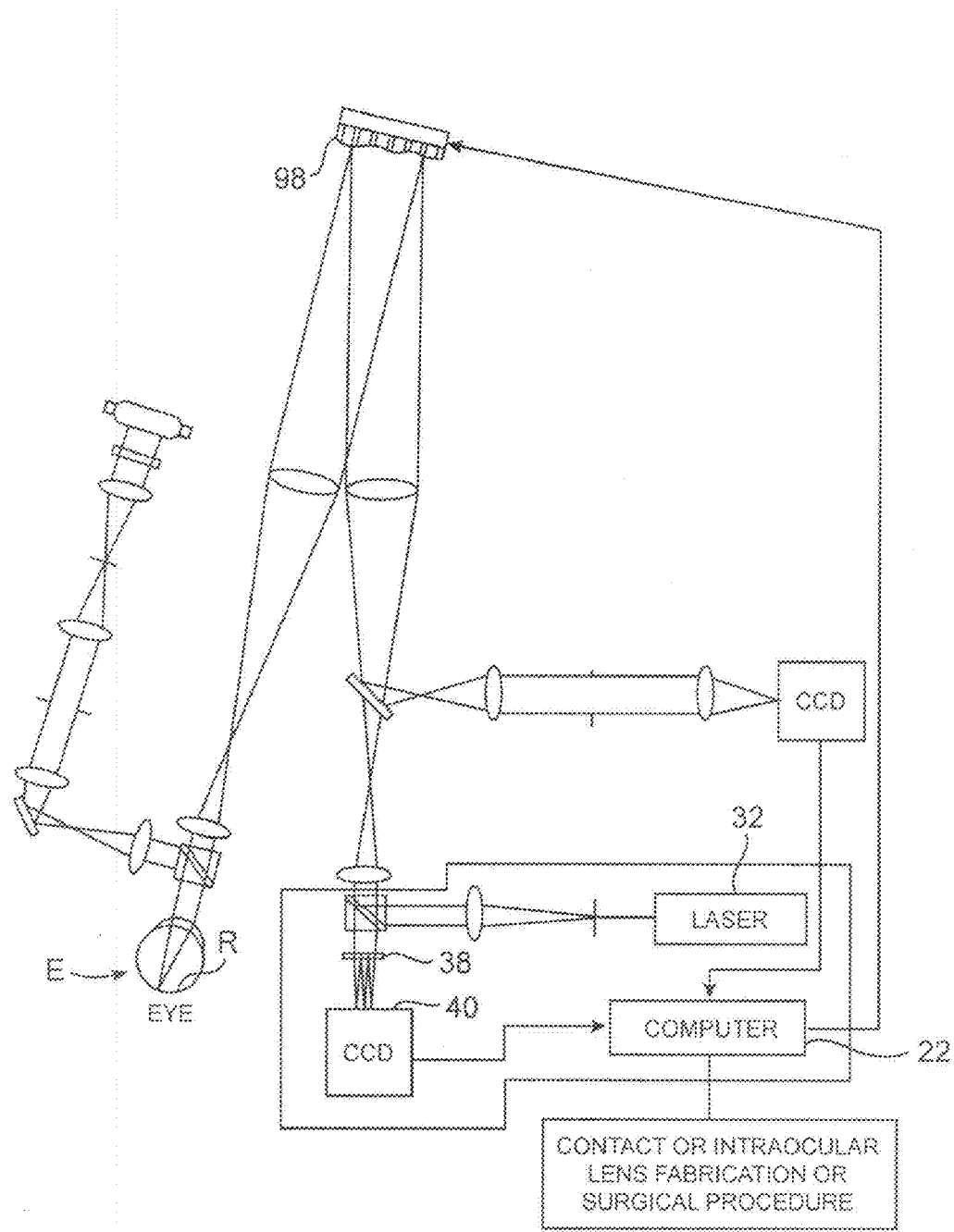
FIG. 3A illustrates another wavefront measurement system according to another embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations comprise elements of a VISX WaveScan®, available from VISX, INCORPORATED of Santa Clara, Calif. One embodiment includes a WaveScan® with a deformable mirror as described above. An alternate embodiment of a wavefront measuring system is described in U.S. Pat. No. 6,271,915, the full disclosure of which is incorporated herein by reference.

The use of modal reconstruction with Zernike polynomials, as well as a comparison of modal and zonal reconstructions, has been discussed in detail by W. H. Southwell, "Wave-front estimation from wave-front slope measurements," J. Opt. Soc. Am. 70:998-1006 (1980). Relatedly, G. Dai, "Modal wave-front reconstruction with Zernike polynomials and Karhunen-Loeve functions," J. Opt. Soc. Am. 13:1218-1225 (1996) provides a detailed analysis of various wavefront reconstruction errors with modal reconstruction with Zernike polynomials. Zernike polynomials have been employed to model the optical surface, as proposed by Liang et al., in "Objective Measurement of Wave Aberrations of the Human Eye with the Use of a Harman-Shack Wave-front Sensor," J. Opt. Soc. Am. 11(7):1949-1957 (1994). The entire contents of each of these references are hereby incorporated by reference.

The Zernike function method of surface reconstruction and its accuracy for normal eyes have been studied extensively for regular corneal shapes in Schweigerling, J. et al., "Using corneal height maps and polynomial decomposition to determine corneal aberrations," Opt. Vis. Sci., Vol. 74, No. 11 (1997) and Guirao, A. et al. "Corneal wave aberration from videokeratography: Accuracy and limitations of the procedure," J. Opt. Soc. Am., Vol. 17, No. 6 (2000). D. R. Ishkander et al., "An Alternative Polynomial Representation of the Wavefront Error Function," IEEE Transactions on Biomedical Engineering, Vol. 49, No. 4, (2002) report that the 6th order Zernike polynomial reconstruction method provides an inferior fit when compared to a method of Bhatia-Wolf polynomials. The entire contents of each of these references are hereby incorporated by reference.

Modal wavefront reconstruction typically involves expanding the wavefront into a set of basis functions. Use of Zernike polynomials as a set of wavefront expansion basis functions has been accepted in the wavefront technology field due to the fact that Zernike polynomials are a set of complete and orthogonal functions over a circular pupil. In addition, some lower order Zernike modes, such as defocus, astigmatism, coma and spherical aberrations, represent classical aberrations. Unfortunately, there may be drawbacks to the use of Zernike polynomials. Because the Zernike basis function has a rapid fluctuation near the periphery of the aperture, especially for higher orders, a slight change in the Zernike coefficients can greatly affect the wavefront surface. Further, due to the aberration balancing between low and high order Zernike modes, truncation of Zernike series often causes inconsistent Zernike coefficients.

In order to solve some of the above-mentioned problems with Zernike reconstruction, other basis functions were considered. Fourier series appear to be an advantageous basis function set due to its robust fast Fourier transform (FFT) algorithm. Also, the derivatives of Fourier series are still a set of Fourier series. For un-bounded functions (i.e. with no boundary conditions), Fourier reconstruction can be used to directly estimate the function from a set of gradient data. It may be difficult, however, to apply this technique directly to wavefront technology because wavefront reconstruction typically relates to a bounded function, or a function with a pupil aperture.

Iterative Fourier reconstruction techniques can apply to bounded functions with unlimited aperture functions. This is to say, the aperture of the function can be circular, annular, oval, square, rectangular, or any other shape. Such an approach is discussed in Roddier et al., "Wavefront reconstruction using iterative Fourier transforms," Appl. Opt. 30, 1325-1327 (1991), the entire contents of which are hereby incorporated by reference. Such approaches, however, are significantly improved by accounting for missing data points due to corneal reflection, bad CCD pixels, and the like.

I. Determining an Optical Surface Model for an Optical Tissue System of an Eye

The present invention provides systems, software, and methods that can use high speed and accurate iterative Fourier transformation algorithms to mathematically determine an optical surface model for an optical tissue system of an eye.

A. Inputting Optical Data from the Optical Tissue System of the Eye

There are a variety of devices and methods for generating optical data from optical tissue systems. The category of aberroscopes or aberrometers includes classical phoropter and wavefront approaches. Topography based measuring devices and methods can also be used to generate optical data. Wavefront devices are often used to measure both low order and high order aberrations of an optical tissue system. Particularly, wavefront analysis typically involves transmitting an image through the optical system of the eye, and determining a set of surface gradients for the optical tissue system based on the transmitted image. The surface gradients can be used to determine the optical data.

Figure 4:
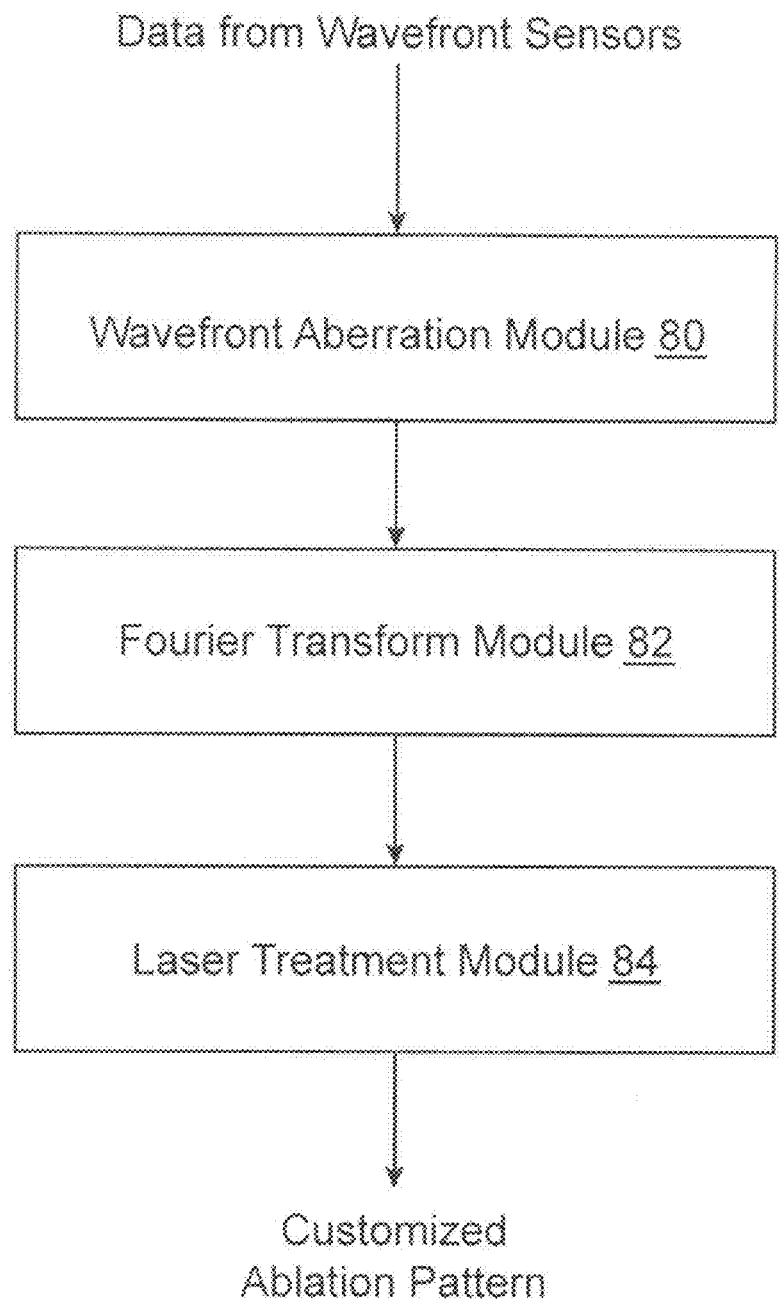
FIG. 4 schematically illustrates a simplified set of modules that carry out one method of the present invention.

B. Determining the Optical Surface Model by Applying an Iterative Fourier Transform to the Optical Data FIG. 4 schematically illustrates a simplified set of modules for carrying out a method according to one embodiment of the present invention. The modules may be software modules on a computer readable medium that is processed by processor 52 (FIG. 2), hardware modules, or a combination thereof. A wavefront aberration module 80 typically receives data from the wavefront sensors and measures the aberrations and other optical characteristics of the entire optical tissue system imaged. The data from the wavefront sensors are typically generated by transmitting an image (such as a small spot or point of light) through the optical tissues, as described above. Wavefront aberration module 80 produces an array of optical gradients or a gradient map. The optical gradient data from wavefront aberration module 80 may be transmitted to a Fourier transform module 82, where an optical surface or a model thereof, or a wavefront elevation surface map, can be mathematically reconstructed from the optical gradient data.

It should be understood that the optical surface or model thereof need not precisely match an actual tissue surface, as the gradient data will show the effects of aberrations which are actually located throughout the ocular tissue system. Nonetheless, corrections imposed on an optical tissue surface so as to correct the aberrations derived from the gradients should correct the optical tissue system. As used herein terms such as "an optical tissue surface" or "an optical surface model" may encompass a theoretical tissue surface (derived, for example, from wavefront sensor data), an actual tissue surface, and/or a tissue surface formed for purposes of treatment (for example, by incising corneal tissues so as to allow a flap of the corneal epithelium and stroma to be displaced and expose the underlying stroma during a LASIK procedure).

Once the wavefront elevation surface map is generated by Fourier transform module 82, the wavefront gradient map may be transmitted to a laser treatment module 84 for generation of a laser ablation treatment to treat or ameliorate optical errors in the optical tissues.

Figure 5:
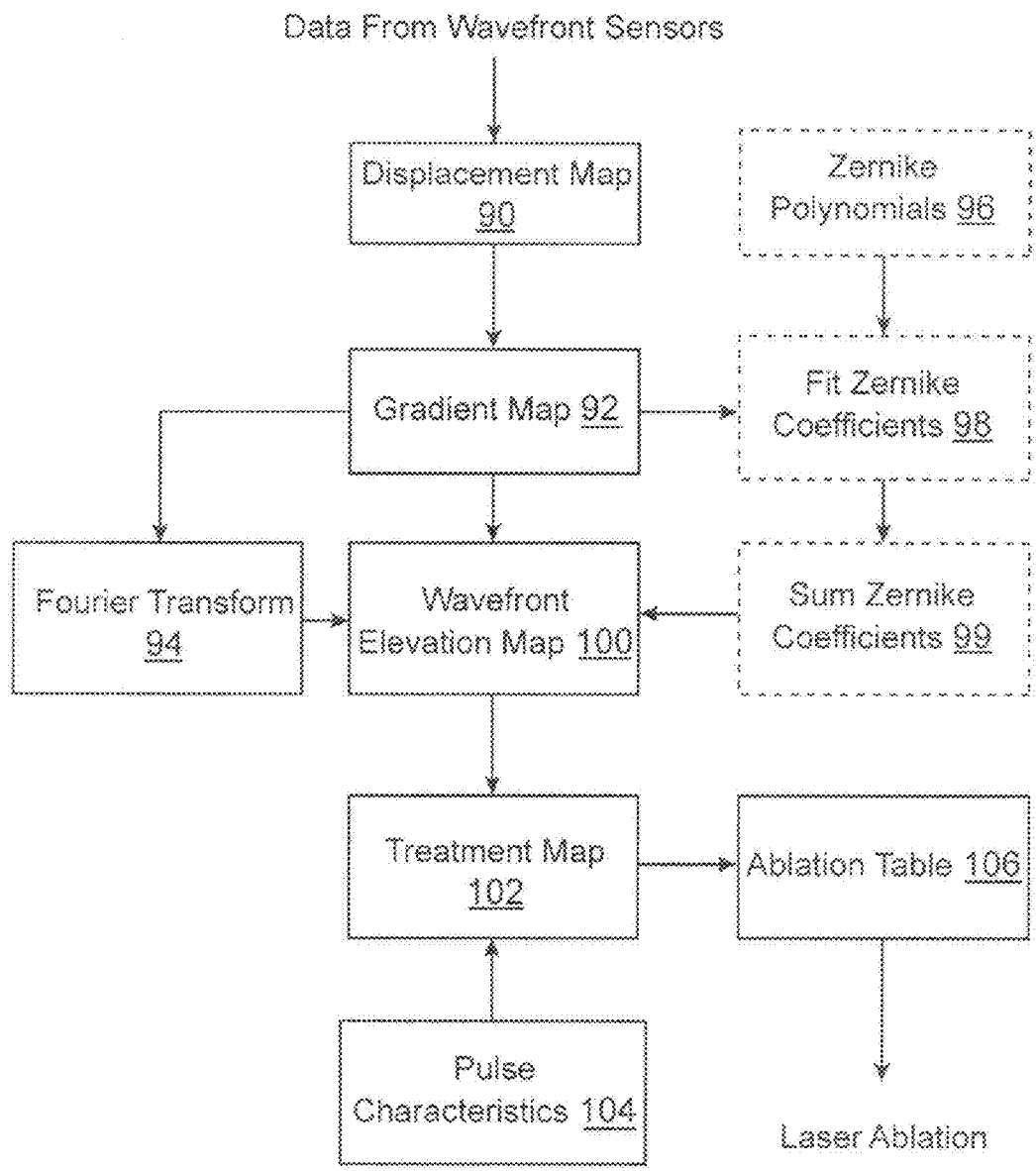
FIG. 5 is a flow chart that schematically illustrates a method of using a Fourier transform algorithm to determine a corneal ablation treatment program according to one embodiment of the present invention.

FIG. 5 is a detailed flow chart which illustrates a data flow and method steps of one Fourier based method of generating a laser ablation treatment. The illustrated method is typically carried out by a system that includes a processor and a memory coupled to the processor. The memory may be configured to store a plurality of modules which have the instructions and algorithms for carrying out the steps of the method.

As can be appreciated, the present invention should not be limited to the order of steps, or the specific steps illustrated, and various modifications to the method, such as having more or less steps, may be made without departing from the scope of the present invention. For comparison purposes, a series expansion method of generating a wavefront elevation map is shown in dotted lines, and are optional steps.

A wavefront measurement system that includes a wavefront sensor (such as a Hartmann-Shack sensor) may be used to obtain one or more displacement maps 90 (e.g., Hartmann-Shack displacement maps) of the optical tissues of the eye. The displacement map may be obtained by transmitting an image through the optical tissues of the eye and sensing the exiting wavefront surface.

From the displacement map 90, it is possible to calculate a surface gradient or gradient map 92 (e.g., Hartmann-Shack gradient map) across the optical tissues of the eye. Gradient map 92 may comprise an array of the localized gradients as calculated from each location for each lenslet of the Hartmann-Shack sensor.

A Fourier transform may be applied to the gradient map to mathematically reconstruct the optical tissues or to determine an optical surface model. The Fourier transform will typically output the reconstructed optical tissue or the optical surface model in the form of a wavefront elevation map. For the purposes of the instant invention, the term Fourier transform also encompasses iterative Fourier transforms.

It has been found that a Fourier transform reconstruction method, such as a fast Fourier transformation (FFT), is many times faster than currently used 6th order Zernike or polynomial reconstruction methods and yields a more accurate reconstruction of the actual wavefront. Advantageously, the Fourier reconstruction limits the spatial frequencies used in reconstruction to the Nyquist limit for the data density available and gives better resolution without aliasing. If it is desired, for some a priori reason, to limit the spatial frequencies used, this can be done by truncating the transforms of the gradient in Fourier transformation space midway through the calculation. If it is desired to sample a small portion of the available wavefront or decenter it, this may be done with a simple mask operation on the gradient data before the Fourier transformation operation. Unlike Zernike reconstruction methods in which the pupil size and centralization of the pupil is required, such concerns do not effect the fast Fourier transformation.

Moreover, since the wavefront sensors measure x- and y-components of the gradient map on a regularly spaced grid, the data is band-limited and the data contains no spatial frequencies larger than the Nyquist rate that corresponds to the spacing of the lenslets in the instrument (typically, the lenslets will be spaced no more than about 0.8 mm and about 0.1 mm, and typically about 0.4 mm). Because the data is on a regularly spaced Cartesian grid, non-radial reconstruction methods, such as a Fourier transform, are well suited for the band-limited data.

In contrast to the Fourier transform, when a series expansion technique is used to generate a wavefront elevation map 100 from the gradient map 92, the gradient map 92 and selected expansion series 96 are used to derive appropriate expansion series coefficients 98. A particularly beneficial form of a mathematical series expansion for modeling the tissue surface are Zernike polynomials. Typical Zernike polynomial sets including terms 0 through 6th order or 0 through 10th order are used. The coefficients $a_n$ for each Zernike polynomial $Z_n$ may, for example, be determined using a standard least squares fit technique. The number of Zernike polynomial coefficients $a_n$ may be limited (for example, to about 28 coefficients).

While generally considered convenient for modeling of the optical surface so as to generate an elevation map, Zernike polynomials (and perhaps all series expansions) can introduce errors. Nonetheless, combining the Zernike polynomials with their coefficients and summing the Zernike coefficients 99 allows a wavefront elevation map 100 to be calculated, and in some cases, may very accurately reconstruct a wavefront elevation map 100.

It has been found that in some instances, especially where the error in the optical tissues of the eye is spherical, the Zernike reconstruction may be more accurate than the Fourier transform reconstruction. Thus, in some embodiments, the modules of the present invention may include both a Fourier transform module 94 and Zernike modules 96, 98, 99. In such embodiments, the reconstructed surfaces obtained by the two modules may be compared by a comparison module (not shown) to determine which of the two modules provides a more accurate wavefront elevation map. The more accurate wavefront elevation map may then be used by 100, 102 to calculate the treatment map and ablation table, respectively.

In one embodiment, the wavefront elevation map module 100 may calculate the wavefront elevation maps from each of the modules and a gradient field may be calculated from each of the wavefront elevation maps. In one configuration, the comparison module may apply a merit function to determine the difference between each of the gradient maps and an originally measured gradient map. One example of a merit function is the root mean square gradient error, $RMS_{grad}$, found from the following equation:

$$RMS_{grad} = \sqrt{\frac{\sum_{alldatapoints}\{(\partial W(x,y)/\partial x - Dx(x,y)^2) + (\partial W(x,y)/\partial y - Dy(x,y)^2)\}}{N}}$$

where:
N is the number of locations sampled
(x,y) is the sample location
$\partial W(x,y)/\partial x$ is the x component of the reconstructed wavefront gradient
$\partial W(x,y)/\partial y$ is the y component of the reconstructed wavefront gradient
Dx(x,y) is the x component of the gradient data
Dy(x,y) is the y component of the gradient data If the gradient map from the Zernike reconstruction is more accurate, the Zernike reconstruction is used. If the Fourier reconstruction is more accurate, the Fourier reconstruction is used.

After the wavefront elevation map is calculated, treatment map 102 may thereafter be calculated from the wavefront elevation map 100 so as to remove the regular (spherical and/or cylindrical) and irregular errors of the optical tissues. By combining the treatment map 102 with a laser ablation pulse characteristics 104 of a particular laser system, an ablation table 106 of ablation pulse locations, sizes, shapes, and/or numbers can be developed.

A laser treatment ablation table 106 may include horizontal and vertical position of the laser beam on the eye for each laser beam pulse in a series of pulses. The diameter of the beam may be varied during the treatment from about 0.65 mm to 6.5 mm. The treatment ablation table 106 typically includes between several hundred pulses to five thousand or more pulses, and the number of laser beam pulses varies with the amount of material removed and laser beam diameters employed by the laser treatment table. Ablation table 106 may optionally be optimized by sorting of the individual pulses so as to avoid localized heating, minimize irregular ablations if the treatment program is interrupted, and the like. The eye can thereafter be ablated according to the treatment table 106 by laser ablation.

In one embodiment, laser ablation table 106 may adjust laser beam 14 to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379 and 6,203,539, and as also described in U.S. application Ser. No. 09/274,999 filed Mar. 22, 1999, the full disclosures of which are incorporated herein by reference.

Still further alternatives are possible, including scanning of the laser beam over a surface of the eye and controlling the number of pulses and/or dwell time at each location, as described, for example, by U.S. Pat. No. 4,665,913 (the full disclosure of which is incorporated herein by reference); using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like.

One exemplary method and system for preparing such an ablation table is described in U.S. Pat. No. 6,673,062, the full disclosure of which is incorporated herein by reference.

The mathematical development for the surface reconstruction from surface gradient data using a Fourier transform algorithm according to one embodiment of the present invention will now be described. Such mathematical algorithms will typically be incorporated by Fourier transform module 82 (FIG. 4), Fourier transform step 94 (FIG. 5), or other comparable software or hardware modules to reconstruct the wavefront surface. As can be appreciated, the Fourier transform algorithm described below is merely an example, and the present invention should not be limited to this specific implementation.

First, let there be a surface that may be represented by the function s(x,y) and let there be data giving the gradients of this surface, $$\frac{\partial s(x,y)}{\partial x} \text{ and } \frac{\partial s(x,y)}{\partial y}.$$

The goal is to find the surface s(x,y) from the gradient data.

Let the surface be locally integratable over all space so that it may be represented by a Fourier transform. The Fourier transform of the surface is then given by $$F(s(x,y)) = \frac{1}{2\pi}\int_{-\infty}^{\infty}\int_{-\infty}^{\infty} s(x,y)e^{-i(ux+vy)}dxdy \quad (1)$$
$$= S(u,v)$$

The surface may then be reconstructed from the transform coefficients, S(u,v), using $$s(x,y) = \frac{1}{2\pi}\int_{-\infty}^{\infty}\int_{-\infty}^{\infty} S(u,v)e^{i(ux+vy)}dudv \quad (2)$$

Equation (2) may now be used to give a representation of the x component of the gradient, $$\frac{\partial s(x,y)}{\partial x}$$

in terms of the Fourier coefficients for the surface:

$$\frac{\partial s(x,y)}{\partial x} = \frac{\partial\left(\frac{1}{2\pi}\int_{-\infty}^{\infty}\int_{-\infty}^{\infty} S(u,v)e^{i(ux+vy)}dudv\right)}{\partial x}$$

Differentiation under the integral then gives:

$$\frac{\partial s(x,y)}{\partial x} = \frac{1}{2\pi}\int_{-\infty}^{\infty}\int_{-\infty}^{\infty} iuS(u,v)e^{i(ux+vy)}\,du\,dv \quad (3)$$

A similar equation to (3) gives a representation of the y component of the gradient in terms of the Fourier coefficients:

$$\frac{\partial s(x,y)}{\partial y} = \frac{1}{2\pi}\int_{-\infty}^{\infty}\int_{-\infty}^{\infty} ivS(u,v)e^{i(ux+vy)}\,du\,dv \quad (4)$$

The x component of the gradient is a function of x and y so it may also be represented by the coefficients resulting from a Fourier transformation. Let the $$dx(x,y) = \frac{\partial s(x,y)}{\partial x}$$

so that, following the logic that led to (2)

$$dx(x,y) = \frac{1}{2\pi}\int_{-\infty}^{\infty}\int_{-\infty}^{\infty} Dx(u,v)e^{i(ux+vy)}\,du\,dv \quad (5)$$
$$= \frac{\partial s(x,y)}{\partial x}$$

where $$F(dx(x,y)) = \int_{-\infty}^{\infty}\int_{-\infty}^{\infty} dx(x,y)e^{-i(ux+vy)}\,dx\,dy \quad (6)$$
$$= Dx(u,v)$$

Equation (3) must equal (5) and by inspecting similar terms it may be seen that in general this can only be true if $$Dx(u,v) = iuS(u,v) \quad (7)$$

or $$S(u,v) = \frac{-iDx(u,v)}{u}$$

A similar development for the y gradient component using (4) leads to $$S(u,v) = \frac{-iDy(u,v)}{v} \quad (8)$$

Note that (7) and (8) indicate that Dx(u,v) and Dy(u,v) are functionally dependent with the relationship $$vDx(u,v) = uDy(u,v)$$

The surface may now be reconstructed from the gradient data by first performing a discrete Fourier decomposition of the two gradient fields, dx and dy to generate the discrete Fourier gradient coefficients Dx(u,v) and Dy(u,v). From these components (7) and (8) are used to find the Fourier coefficients of the surface S(u,v). These in turn are used with an inverse discrete Fourier transform to reconstruct the surface s(x,y).

The above treatment makes a non-symmetrical use of the discrete Fourier gradient coefficients in that one or the other is used to find the Fourier coefficients of the surface. The method makes use of the Laplacian, a polynomial, second order differential operator, given by $$L \equiv \frac{\partial^2}{\partial^2 x} + \frac{\partial^2}{\partial^2 y} \text{ or } L \equiv \frac{\partial}{\partial x}\left(\frac{\partial}{\partial x}\right) + \frac{\partial}{\partial y}\left(\frac{\partial}{\partial y}\right)$$

So when the Laplacian acts on the surface function, s(x,y), the result is $$Ls(x,y) = \frac{\partial^2 s(x,y)}{\partial^2 x} + \frac{\partial^2 s(x,y)}{\partial^2 y}$$

or $$Ls(x,y) = \frac{\partial}{\partial x}\left(\frac{\partial s(x,y)}{\partial x}\right) + \frac{\partial}{\partial y}\left(\frac{\partial s(x,y)}{\partial y}\right)$$

Using the second form given above and substituting (3) for $$\frac{\partial s(x,y)}{\partial x}$$

in the first integral of the sum and (4) for $$\frac{\partial s(x,y)}{\partial y}$$

in the second term, the Laplacian of the surface is found to be $$Ls(x,y) = \frac{\partial}{\partial x}\left(\frac{1}{2\pi}\int_{-\infty}^{\infty}\int_{-\infty}^{\infty} iuS(u,v)e^{i(ux+vy)}\,du\,dv\right) + \quad (9)$$
$$\frac{\partial}{\partial y}\left(\frac{1}{2\pi}\int_{-\infty}^{\infty}\int_{-\infty}^{\infty} ivS(u,v)e^{i(ux+vy)}\,du\,dv\right)$$

$$Ls(x,y) = \frac{1}{2\pi}\int_{-\infty}^{\infty}\int_{-\infty}^{\infty} -u^2 S(u,v)e^{i(ux+vy)}\,du\,dv +$$
$$\frac{1}{2\pi}\int_{-\infty}^{\infty}\int_{-\infty}^{\infty} -v^2 S(u,v)e^{i(ux+vy)}\,du\,dv$$

$$Ls(x,y) = \frac{1}{2\pi}\int_{-\infty}^{\infty}\int_{-\infty}^{\infty} -(u^2+v^2)S(u,v)e^{i(ux+vy)}\,du\,dv$$

Equation (9) shows that the Fourier coefficients of the Laplacian of a two dimensional function are equal to $-(u^2+v^2)$ times the Fourier coefficients of the function itself so that $$S(u,v) = \frac{-F(Ls(x,y))}{(u^2+v^2)}$$

Now let the Laplacian be expressed in terms of dx(x,y) and dy(x,y) as defined above so that $$Ls(x,y) = \frac{\partial}{\partial x}(dx(x,y)) + \frac{\partial}{\partial y}(dy(x,y))$$

and through the use of (5) and the similar expression for dy(x,y)

$$Ls(x, y) = \frac{\partial}{\partial x}\left(\frac{1}{2\pi}\int_{-\infty}^{\infty}\int_{-\infty}^{\infty}Dx(u, v)e^{i(ux+vy)}dudv\right) + \qquad (10)$$
$$\frac{\partial}{\partial y}\left(\frac{1}{2\pi}\int_{-\infty}^{\infty}\int_{-\infty}^{\infty}Dy(u, v)e^{i(ux+vy)}dudv\right)$$

$$Ls(x, y) = \frac{1}{2\pi}\int_{-\infty}^{\infty}\int_{-\infty}^{\infty}iuDx(u, v)e^{i(ux+vy)}dudv +$$
$$\frac{1}{2\pi}\int_{-\infty}^{\infty}\int_{-\infty}^{\infty}ivDy(u, v)e^{i(ux+vy)}dudv$$

$$Ls(x, y) = \frac{1}{2\pi}\int_{-\infty}^{\infty}\int_{-\infty}^{\infty}i(uDx(u, v) + vDy(u, v))e^{i(ux+vy)}dudv$$

(9) and (10) must be equal and comparing them, it is seen that this requires that:

$$-(u^2 + v^2)S(u, v) = i(uDx(u, v) + vD(u, v)) \qquad (11)$$

or $$S(u, v) = \frac{-i(uDx(u, v) + vDy(u, v))}{u^2 + v^2}$$

As before, Dx(u,v) and Dy(u,v) are found by taking the Fourier transforms of the measured gradient field components. They are then used in (11) to find the Fourier coefficients of the surface itself, which in turn is reconstructed from them. This method has the effect of using all available information in the reconstruction, whereas the Zernike polynomial method fails to use all of the available information.

It should be noted, s(x,y) may be expressed as the sum of a new function s(x,y)' and a tilted plane surface passing through the origin. This sum is given by the equation $$s(x,y)=s(x,y)'+ax+by$$

Then the first partial derivatives of f(x,y) with respect to x and y are given by $$\frac{\partial s(x, y)}{\partial x} = \frac{\partial s(x, y)'}{\partial x} + a$$
$$\frac{\partial s(x, y)}{\partial y} = \frac{\partial s(x, y)'}{\partial y} + b$$

Now following the same procedure that lead to (6), the Fourier transform of these partial derivatives, Dx(u,v) and Dy(u,v), are found to be $$Dx(u, v) = \frac{1}{2\pi}\int_{-\infty}^{\infty}\int_{-\infty}^{\infty}\frac{\partial s(x, y)}{\partial x}e^{-i(ux+vy)}dxdy = \qquad (12)$$
$$\frac{1}{2\pi}\int_{-\infty}^{\infty}\int_{-\infty}^{\infty}\frac{\partial s(x, y)'}{\partial x}e^{-i(ux+vy)}dxdy +$$
$$\frac{a}{2\pi}\int_{-\infty}^{\infty}\int_{-\infty}^{\infty}e^{-i(ux+vy)}dxdy$$
$$Dx(u, v) = Dx(u, v)' + a\delta(u, v))$$

-continued $$Dy(u, v) = \frac{1}{2\pi}\int_{-\infty}^{\infty}\int_{-\infty}^{\infty}\frac{\partial s(x, y)}{\partial y}e^{-i(ux+vy)}dxdy = \qquad (13)$$
$$\frac{1}{2\pi}\int_{-\infty}^{\infty}\int_{-\infty}^{\infty}\frac{\partial s(x, y)'}{\partial y}e^{-i(ux+vy)}dxdy +$$
$$\frac{b}{2\pi}\int_{-\infty}^{\infty}\int_{-\infty}^{\infty}e^{-i(ux+vy)}dxdy$$
$$Dy(u, v) = Dy(u, v)' + b\delta(u, v))$$

In (12) and (13), δ(u,v), is the Dirac delta function that takes the value 1 if u=v=0 and takes the value 0 otherwise. Using (12) and (13) in (11), the expression of the Fourier transform of the surface may be written as $$S(u, v) = \frac{-i(uDx(u, v)' + vDy(u, v)' + (ua + vb)\delta(u, v))}{u^2 + v^2}$$

But it will be realized that the term in the above equation can have no effect whatsoever on the value of S(u,v) because if u and v are not both zero, the delta function is zero so the term vanishes. However in the only other case, u and v are both zero and this also causes the term to vanish. This means that the surface reconstructed will not be unique but will be a member of a family of surfaces, each member having a different tilted plane (or linear) part. Therefore to reconstruct the unique surface represented by a given gradient field, the correct tilt must be restored. The tilt correction can be done in several ways.

Since the components of the gradient of the tilt plane, a and b, are the same at every point on the surface, if the correct values can be found at one point, they can be applied everywhere at once by adding to the initially reconstructed surface, s(x,y)', the surface (ax+by). This may be done by finding the gradient of s(x,y)' at one point and subtracting the components from the given components. The differences are the constant gradient values a and b. However when using real data there is always noise and so it is best to use an average to find a and b. One useful way to do this is to find the average gradient components of the given gradient field and use these averages as a and b.

$$\langle\partial s/\partial x\rangle = a \quad \langle\partial s/\partial y\rangle = b$$

The reconstructed surface is then given by $$s(x,y)=s(x,y)'+\langle\partial s/\partial x\rangle x+\langle\partial s/\partial y\rangle y \qquad (14)$$

where s(x,y)' is found using the Fourier reconstruction method developed above.

Attention is now turned to implementation of this method using discrete fast Fourier transform methods. The algorithm employed for the discrete fast Fourier transform in two dimensions is given by the equation $$F(k, l) = \sum_{m=1}^{M}\sum_{n=1}^{N}f(n, m)e^{-i2\pi\left(\frac{(k-1)(n-1)}{N}+\frac{(l-1)(m-1)}{M}\right)} \qquad (1A)$$

with the inverse transform given by $$f(n, m) = \frac{1}{MN}\sum_{k=1}^{M}\sum_{l=1}^{N}F(k, l)e^{i2\pi\left(\frac{(k-1)(n-1)}{N}+\frac{(l-1)(m-1)}{M}\right)} \qquad (2A)$$

When these equations are implemented N and M are usually chosen so to be equal. For speed of computation, they are usually taken to be powers of 2. (1A) and (2A) assume that the function is sampled at locations separated by intervals dx and dy. For reasons of algorithmic simplification, as shown below, dx and dy are usually set equal.

In equation (1A) let n be the index of the x data in array f(n,m) and let k be the index of the variable u in the transform array, F(k,l).

Let us begin by supposing that in the discrete case the x values are spaced by a distance dx, so when equation (1A) is used, each time n is incremented, x is changed by an amount dx. So by choosing the coordinate system properly it is possible to represent the position of the pupil data x by:

$$x=(n-1)dx$$

so that:

$$(n-1)=x/dx$$

Likewise, (m−1) may be set equal to y/dy. Using these relationships, (1A) may be written as:

$$F(k, l) = \sum_{m=1}^{M}\sum_{n=1}^{N} f(n, m) e^{-i2\pi\left(\frac{(k-1)x}{Ndx} + \frac{(l-1)y}{Mdy}\right)}$$

Comparing the exponential terms in this discrete equation with those in its integral form (1), it is seen that $$u = \frac{2\pi(k-1)}{Ndx}$$

and $$v = \frac{2\pi(l-1)}{Mdy}$$

In these equations notice that Ndx is the x width of the sampled area and Mdy is the y width of the sampled area. Letting (1C) Ndx=X, the total x width
    Mdy=Y, the total y width
The above equations become $$u(k) = \frac{2\pi(k-1)}{X} \tag{15}$$

and $$v(l) = \frac{2\pi(l-1)}{Y}$$

Equations (15) allow the Fourier coefficients, Dx(k,l) and Dy(k,l), found from the discrete fast Fourier transform of the gradient components, dx(n,m) and dy(n,m), to be converted into the discrete Fourier coefficients of the surface, S(k,l) as follows.

$$S(k, l) = \frac{-i\frac{2\pi(k-1)}{X}Dx(k,l) - i\frac{2\pi(l-1)}{Y}Dy(k,l)}{\left(\frac{2\pi(k-1)}{X}\right)^2 + \left(\frac{2\pi(l-1)}{Y}\right)^2}$$

This equation is simplified considerably if the above mentioned N is chosen equal to M and dx is chosen to dy, so that X=Y. It then becomes $$S(k, l) = \left(\frac{-iX}{2\pi}\right)\frac{(k-1)Dx(k,l) + (l-1)Dy(k,l)}{(k-1)^2 + (l-1)^2} \tag{16}$$

Let us now consider the values u(k) and v(l) take in (1B) as k varies from 1 to N and l varies from 1 to M. When k=l=1, u=v=0 and the exponential takes the value 1. As u and v are incremented by 1 so that k=l=2, u and v are incremented by unit increments, du and dv, so $$u(2) = \frac{2\pi}{X} = du$$

and $$v(2) = \frac{2\pi}{Y} = dv$$

Each increment of k or l increments u or v by amounts du and dv respectively so that for any value of k or l, u(k) and v(l) may be written as $$u(k)=(k-1)du, v(l)=(l-1)dv$$

This process may be continued until k=N and l=M at which time $$u(N) = \frac{2\pi(N-1)}{X} = \frac{2\pi(N)}{X} - \frac{2\pi}{X} = \frac{2\pi(N)}{X} - du$$

$$v(M) = \frac{2\pi(M-1)}{X} = \frac{2\pi(M)}{X} - \frac{2\pi}{X} = \frac{2\pi(M)}{X} - dv$$

But now consider the value the exponential in (1B) takes when these conditions hold. In the following, the exponential is expressed as a product $$e^{\frac{i2\pi(N-1)(n-1)}{N}} e^{\frac{i2\pi(M-1)(m-1)}{M}} = e^{\left(i2\pi(n-1c) - \frac{i2\pi(n-1)}{N}\right)} e^{\left(i2\pi(m-1c) - \frac{i2\pi(m-1)}{M}\right)}$$

$$= e^{\frac{-i2\pi(n-1)}{N}} e^{\frac{-i2\pi(m-1)}{M}}$$

Using the same logic as was used to obtain equations (15), the values of u(N) and v(M) are $$u(N)=-du \text{ and } v(M)=-dv$$

Using this fact, the following correlation may now be made between u(k+1) and u(N−k) and between v(l+1) and v(M−1) for k>1 and l>1

$$u(k)=-u(N-k+2)v(l)=-v(M-l+2)$$

In light of equations (15)

$$u(N - k + 2) = \frac{-2\pi(k-1)}{X} \tag{17}$$

and $$v(M - l + 2) = \frac{-2\pi(l-1)}{Y}$$

To implement (15), first note that Dx(k,l) and Dy(k,l) are formed as matrix arrays and so it is best to form the coefficients (k-1) and (l-1) as matrix arrays so that matrix multiplication method may be employed to form S(k,l) as a matrix array.

Assuming the Dx and Dy are square arrays of N×N elements, let the (k-1) array, K(k,l) be formed as a N×N array whose rows are all the same consisting of integers starting at 0 (k=1) and progressing with integer interval of 1 to the value ceil(N/2)-1. The "ceil" operator rounds the value N/2 to the next higher integer and is used to account for cases where N is an odd number. Then, in light of the relationships given in (17), the value of the next row element is given the value -floor(N/2). The "floor" operator rounds the value N/2 to the next lower integer, used again for cases where N is odd. The row element following the one with value -floor(N/2) is incremented by 1 and this proceeds until the last element is reached (k=N) and takes the value -1. In this way, when matrix |Dx| is multiplied term by term times matrix |K|, each term of |Dx| with the same value of k is multiplied by the correct integer and hence by the correct u value.

Likewise, let matrix |L(k,l)| be formed as an N×N array whose columns are all the same consisting of integers starting at 0 (l=1) and progressing with integer interval of 1 to the value ceil(N/2)-1. Then, in light of the relationships given in (17), the value of the next column element is given the value -floor(N/2). The column element following the one with value -floor(N/2) is incremented by 1 and this proceeds until the last element is reached (l=N) and takes the value -1. In this way, when matrix |Dy| is multiplied term by term times matrix |L|, each term of |Dy| with the same value of l is multiplied by the correct integer and hence by the correct v value.

The denominator of (15) by creating a matrix |D| from the sum of matrices formed by multiplying, term-by-term, |K| times itself and |L| times itself. The (1,1) element of |D| is always zero and to avoid divide by zero problems, it is set equal to 1 after |D| is initially formed. Since the (1,1) elements of |K| and |L| are also zero at this time, this has the effect of setting the (1,1) element of |S| equal to zero. This is turn means that the average elevation of the reconstructed surface is zero as may be appreciated by considering that the value of (1A) when k=l=1 is the sum of all values of the function f(x,y). If this sum is zero, the average value of the function is zero.

Let the term-by-term multiplication of two matrices |A| and |B| be symbolized by |A|.*|B| and the term-by-term division of |A| by |B| by |A|./|B|. Then in matrix form, (16) may be written as:

$$|S| = \left(\frac{-iX}{2\pi}\right)(|K|.*|Dx| + |L|.*Dy(k, l))./(|K|.*|K| + |L|.*|L|) \quad (18)$$

The common factor $$\left(\frac{-iX}{2\pi}\right)$$

is neither a function of position nor "frequency" (the variables of the Fourier transform space). It is therefore a global scaling factor.

As a practical matter when coding (18), it is simpler to form K and L if the transform matrices Dx and Dy are first "shifted" using the standard discrete Fourier transform quadrant shift technique that places u=v=0 element at location (floor(N/2)+1,floor(N/2)+1). The rows of K and the columns of L may then be formed from $$row = [1, 2, 3, \ldots N-2, N-1, N] - (floor(N/2) + 1)$$

$$column = row^T$$

After the matrix |S| found with (18) using the shifted matrices, |S| is then inverse shifted before the values of s(x,y) are found using the inverse discrete inverse Fourier transform (13).

The final step is to find the mean values of the gradient fields dx(n,m) and dy(n,m). These mean values are multiplied by the respective x and y values for each surface point evaluated and added to the value of s(x,y) found in the step above to give the fully reconstructed surface.

II. Experimental Results

A detailed description of some test methods to compare the surface reconstructions of the expansion series (e.g., Zernike polynomial) reconstruction methods, direct integration reconstruction methods, and Fourier transform reconstruction methods will now be described.

While not described in detail herein, it should be appreciated that the present invention also encompasses the use of direct integration algorithms and modules for reconstructing the wavefront elevation map. The use of Fourier transform modules, direct integration modules, and Zernike modules are not contradictory or mutually exclusive, and may be combined, if desired. For example, the modules of FIG. 5 may also include direct integration modules in addition to or alternative to the modules illustrated. A more complete description of the direct integration modules and methods are described in co-pending U.S. patent application Ser. No. 10/006,992, filed Dec. 6, 2001 and PCT Application No. PCT/US01/46573, filed Nov. 6, 2001, both entitled "Direct Wavefront-Based Corneal Ablation Treatment Program," the complete disclosures of which are incorporated herein by reference.

To compare the various methods, a surface was ablated onto plastic, and the various reconstruction methods were compared to a direct surface measurement to determine the accuracy of the methods. Three different test surfaces were created for the tests, as follows:

(1) +2 ablation on a 6 mm pupil, wherein the ablation center was offset by approximately 1 mm with respect to the pupil center;

(2) Presbyopia Shape I which has a 2.5 mm diameter "bump," 1.5 μm high, decentered by 1.0 mm.

(3) Presbyopia Shape II which has a 2.0 mm diameter "bump," 1.0 μm high, decentered by 0.5 mm.

The ablated surfaces were imaged by a wavefront sensor system 30 (see FIGS. 3 and 3A), and the Hartmann-Shack spot diagrams were processed to obtain the wavefront gradients. The ablated surfaces were also scanned by a surface mapping interferometer Micro XCAM, manufactured by Phase Shift Technologies, so as to generate a high precision surface elevation map. The elevation map directly measured by the Micro XCAM was compared to the elevation map reconstructed by each of the different algorithms. The algorithm with the lowest root mean square (RMS) error was considered to be the most effective in reconstructing the surface.

In both the direct measurement and mathematical reconstruction, there may be a systematic "tilt" that needs correction. For the direct measurement, the tilt in the surface (that was introduced by a tilt in a sample stage holding the sample) was removed from the data by subtracting a plane that would fit to the surface.

For the mathematical reconstructions, the angular and spatial positions of the surface relative to the lenslet array in the wavefront measurement system introduced a tilt and offset of center in the reconstruction surfaces. Correcting the "off-center" alignment was done by identifying dominant features, such as a top of a crest, and translating the entire surface data to match the position of this feature in the reconstruction.

To remove the tilt, in one embodiment a line profile of the reconstructed surface along an x-axis and y-axis were compared with corresponding profiles of the measured surface. The slopes of the reconstructed surface relative to the measured surface were estimated. Also the difference of the height of the same dominant feature (e.g., crest) that was used for alignment of the center was determined. A plane defined by those slopes and height differences was subtracted from the reconstructed surface. In another embodiment, it has been determined that the tilt in the Fourier transform algorithm may come from a DC component of the Fourier transform of the x and y gradients that get set to zero in the reconstruction process. Consequently, the net gradient of the entire wavefront is lost. Adding in a mean gradient field "untips" the reconstructed surface. As may be appreciated, such methods may be incorporated into modules of the present invention to remove the tilt from the reconstructions.

Figure 6:
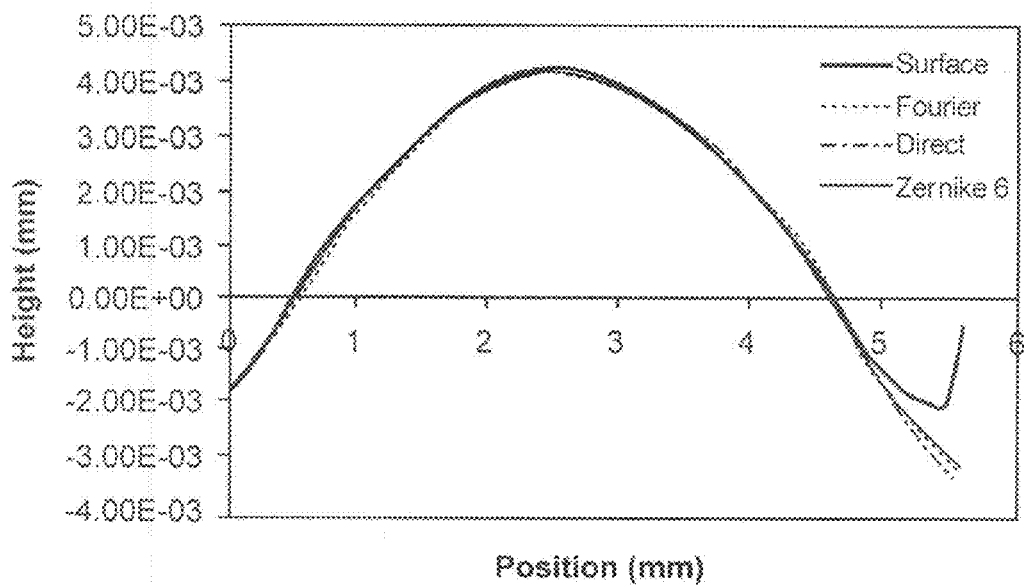
FIG. 6 schematically illustrates a comparison of a direct integration reconstruction, a 6th order Zernike polynomial reconstruction, a 10th order Zernike polynomial reconstruction, and a Fourier transform reconstruction for a surface having a +2 ablation on a 6 mm pupil according to one embodiment of the present invention.

A comparison of reconstructed surfaces and a directly measured surface for a decentered +2 lens is illustrated in FIG. 6. As illustrated in FIG. 6, all of the reconstruction methods matched the surface well. The RMS error for the reconstructions are as follows:

| | |
|---|---|
| Fourier | 0.2113e−3 |
| Direct Integration | 0.2912e−3 |
| Zernike (6th order) | 0.2264e−3 |

Figure 7:
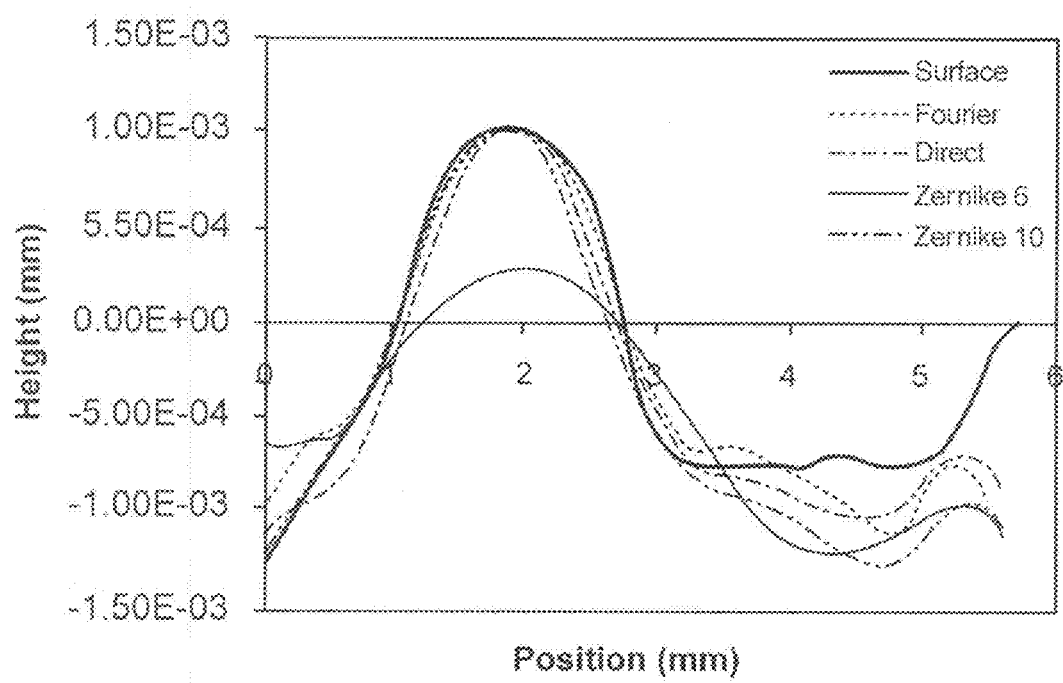
FIG. 7 schematically illustrates a comparison of a direct integration reconstruction, a 6th order Zernike polynomial reconstruction, a 10th order Zernike polynomial reconstruction, and a Fourier transform reconstruction for a presbyopia surface according to one embodiment of the present invention.

FIG. 7 shows a cross section of the Presbyopia Shape I reconstruction. As can be seen, the Zernike 6th order reconstruction excessively widens the bump feature. The other reconstructions provide a better match to the surface. The RMS error for the four reconstruction methods are as follows:

| | |
|---|---|
| Fourier | 0.1921e−3 |
| Direct Integration | 0.1849e−3 |
| Zernike (6th order) | 0.3566e−3 |
| Zernike (10th order) | 0.3046e−3 |

Figure 8:
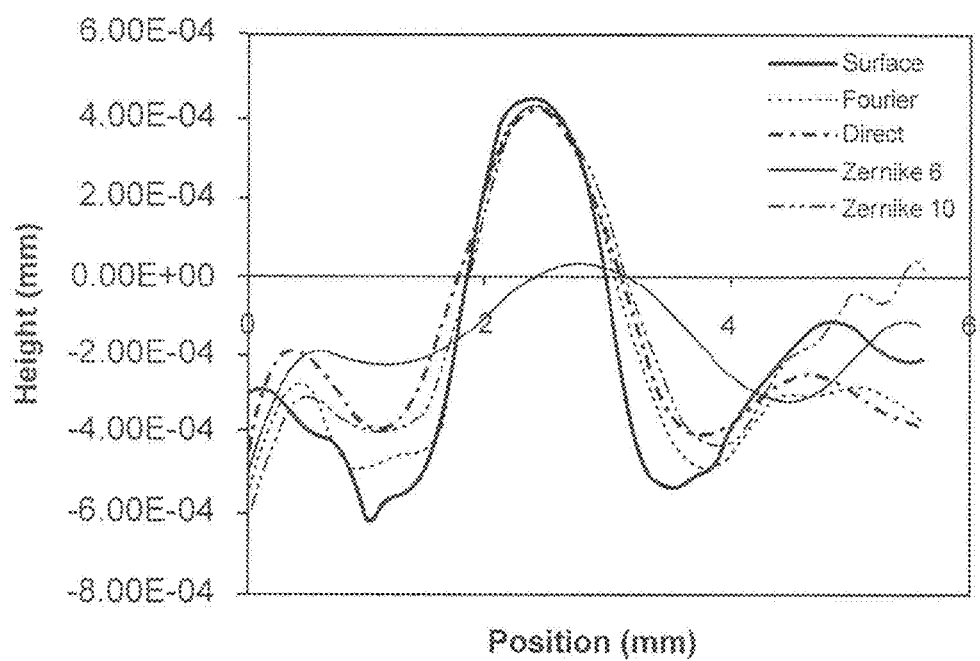
FIG. 8 schematically illustrates a comparison of a direct integration reconstruction, a 6th order Zernike polynomial reconstruction, a 10th order Zernike polynomial reconstruction, and a Fourier transform reconstruction for another presbyopia surface according to one embodiment of the present invention.

FIG. 8 shows a cross section of Presbyopia Shape II reconstruction. The data is qualitatively similar to that of FIG. 7. The RMS error for the four reconstruction methods are as follows:

| | |
|---|---|
| Fourier | 0.1079e−3 |
| Direct Integration | 0.1428e−3 |
| Zernike (6th order) | 0.1836e−3 |
| Zernike (10th order) | 0.1413e−3 |

From the above results, it appears that the 6th order Zernike reconstructions is sufficient for smooth surfaces with features that are larger than approximately 1-2 millimeters. For sharper features, however, such as the bump in the presbyopia shapes, the 6th order Zernike reconstruction gives a poorer match with the actual surface when compared to the other reconstruction methods.

Sharper features or locally rapid changes in the curvature of the corneal surface may exist in some pathological eyes and surgically treated eyes. Additionally, treatments with small and sharp features may be applied to presbyopic and some highly aberrated eyes.

Applicants believe that part of the reason the Fourier transformation provides better results is that, unlike the Zernike reconstruction algorithms (which are defined over a circle and approximates the pupil to be a circle), the Fourier transformation algorithm (as well as the direct integration algorithms) makes full use of the available data and allows for computations based on the actual shape of the pupil (which is typically a slight ellipse). The bandwidth of the discrete Fourier analysis is half of the sampling frequency of the wavefront measuring instrument. Therefore, the Fourier method may use all gradient field data points. Moreover, since Fourier transform algorithms inherently have a frequency cutoff, the Fourier algorithms filter out (i.e., set to zero) all frequencies higher than those that can be represented by the data sample spacing and so as to prevent artifacts from being introduced into the reconstruction such as aliasing. Finally, because many wavefront measurement systems sample the wavefront surface on a square grid and the Fourier method is performed on a square grid, the Fourier method is well suited for the input data from the wavefront instrument.

In contrast, the Zernike methods use radial and angular terms (e.g., polar), thus the Zernike methods weigh the central points and the peripheral points unequally. When higher order polynomials are used to reproduce small details in the wavefront, the oscillations in amplitude as a function of radius are not uniform. In addition, for any given polynomial, the meridional term for meridional index value other than zero is a sinusoidal function. The peaks and valleys introduced by this Zernike term are greater the farther one moves away from the center of the pupil. Moreover, it also introduces non-uniform spatial frequency sampling of the wavefront. Thus, the same polynomial term may accommodate much smaller variations in the wavefront at the center of the pupil than it can at the periphery. In order to get a good sample of the local variations at the pupil edge, a greater number of Zernike terms must be used. Unfortunately, the greater number of Zernike terms may cause over-sampling at the pupil center and introduction of artifacts, such as aliasing. Because Fourier methods provide uniform spatial sampling, the introduction of such artifacts may be avoided.

Figure 9:
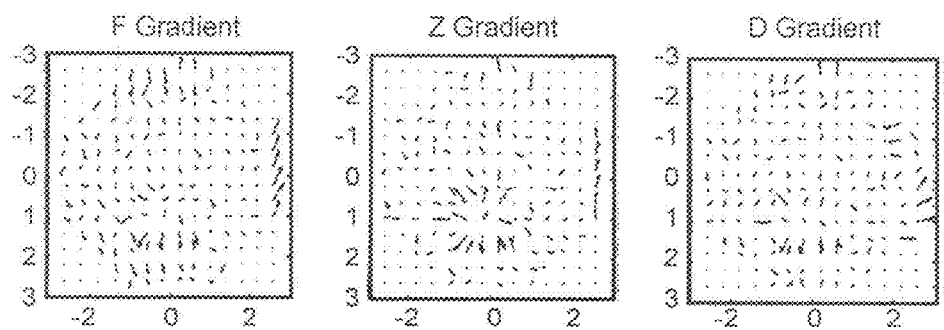
FIG. 9 illustrates a difference in a gradient field calculated from a reconstructed wavefront from a Fourier transform reconstruction algorithm (F Gradient), Zernike polynomial reconstruction algorithm (Z Gradient), a direct integration reconstruction algorithm (D Gradient) and a directly measured wavefront according to one embodiment of the present invention.
Figure 10:
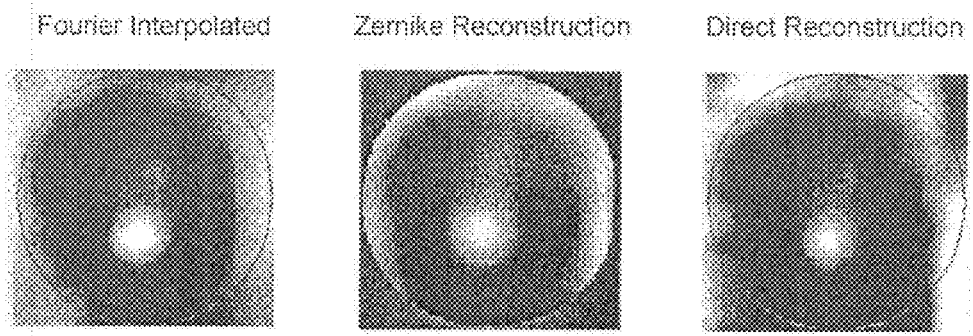
FIG. 10 illustrates intensity plots of reconstructed wavefronts for Fourier, 10th Order Zernike and Direct Integration reconstructions according to one embodiment of the present invention.
Figure 11:
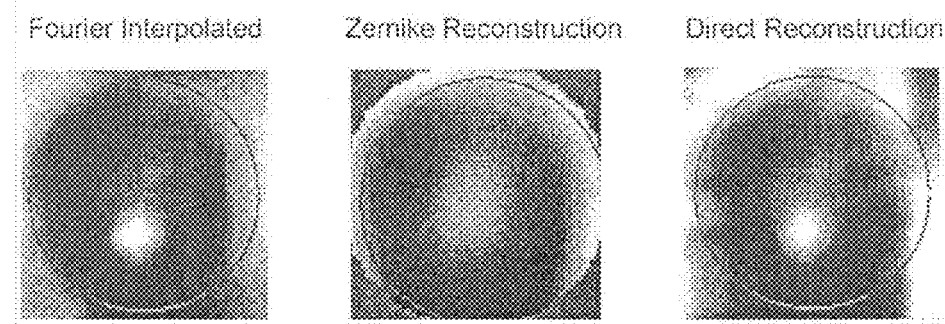
FIG. 11 illustrates intensity plots of reconstructed wavefronts for Fourier, 6th Order Zernike and Direct Integration reconstructions according to one embodiment of the present invention.

Additional test results on clinical data are illustrated in FIGS. 9 to 11. A Fourier method of reconstructing the wavefront was compared with 6th order Zernike methods and a direct integration method to reconstruct the wavefront from the clinical data. The reconstructed wavefronts were then differentiated to calculate the gradient field. The root mean square (RMS) difference between the calculated and the measured gradient field was used as a measure of the quality of reconstruction.

The test methods of the reconstruction were as follow: A wavefront corresponding to an eye with a large amount of aberration was reconstructed using the three algorithms (e.g., Zernike, Fourier, and direct integration). The pupil size used in the calculations was a 3 mm radius. The gradient field of the reconstructed wavefronts were compared against the measured gradient field. The x and y components of the gradient at each sampling point were squared and summed together. The square root of the summation provides information about the curvature of the surface. Such a number is equivalent to the average magnitude of the gradient multiplied by the total number of sampling points. For example, a quantity of 0 corresponds to a flat or planar wavefront. The ratio of the RMS deviation of the gradient field with the quantity gives a measure of the quality of reconstruction. For example, the smaller the ratio, the closer the reconstructed wavefront is to the directly measured wavefront. The ratio of the RMS deviations (described supra) with the quantity of the different reconstructions are as follows:

| | |
|---|---|
| Zernike (6th order) | 1.09 |
| Zernike (10th order) | 0.82 |
| Direct integration | 0.74 |
| Fourier | 0.67 |

FIG. 9 illustrates a vector plot of the difference between the calculated and measured gradient field. The Zernike plot (noted by "Z field") is for a reconstruction using terms up to the 10th order. FIG. 11 illustrates that the Zernike reconstruction algorithm using terms up to 6th order is unable to correctly reproduce small and sharp features on the wavefront. As shown in FIG. 10, Zernike algorithm up to the 10th order term is better able to reproduce the small and sharp features. As seen by the results, the RMS deviation with the measured gradient is minimum for the Fourier method.

The mathematical development for the determination of an optical surface model using an iterative Fourier transform algorithm according to one embodiment of the present invention will now be described.

In wavefront technology, an optical path difference (OPD) of an optical system such as a human eye can be measured. There are different techniques in wavefront sensing, and Hartmann-Shack wavefront sensing has become a popular technique for the measurement of ocular aberrations. A Hartmann-Shack device usually divides an aperture such as a pupil into a set of sub-apertures; each corresponds to one area projected from the lenslet array. Because a Hartmann-Shack device measures local slopes (or gradients) of each sub-aperture, it may be desirable to use the local slope data for wavefront reconstruction.

Assuming that $W(x,y)$ is the wavefront to be reconstructed, the local slope of $W(x,y)$ in x-axis will be $$\frac{\partial W(x,y)}{\partial x}$$

and in y-axis will $$\frac{\partial W(x,y)}{\partial y}.$$

Assuming further that $c(u,v)$ is the Fourier transform of $W(x,y)$, then $W(x,y)$ will be the inverse Fourier transform of $c(u,v)$. Therefore, we have $$W(x,y) = \iint c(u,v) \exp[i2\pi(ux+vy)] du dv, \quad (19)$$

where $c(u,v)$ is the expansion coefficient. Taking a partial derivative of x and y, respectively in Equation (19), we have $$\begin{cases} \frac{\partial W(x,y)}{\partial x} = i2\pi \iint uc(u,v) \exp[i2\pi(ux+vy)] du dv \\ \frac{\partial W(x,y)}{\partial y} = i2\pi \iint vc(u,v) \exp[i2\pi(ux+vy)] du dv \end{cases} \quad (20)$$

Denoting $c_u$ to be the Fourier transform of the x-derivative of $W(x,y)$ and $c_v$ to be the Fourier transform of the y-derivative of $W(x,y)$. From the definition of Fourier transform, we have $$\begin{cases} c_u(u,v) = \iint \frac{\partial W(x,y)}{\partial x} \exp[-i2\pi(ux+vy)] dx dy \\ c_v(u,v) = \iint \frac{\partial W(x,y)}{\partial y} \exp[-i2\pi(ux+vy)] dx dy \end{cases} \quad (21)$$

Equation (21) can also be written in the inverse Fourier transform format as $$\begin{cases} \frac{\partial W(x,y)}{\partial x} = \iint c_u(u,v) \exp[i2\pi(ux+vy)] du dv \\ \frac{\partial W(x,y)}{\partial y} = \iint c_v(u,v) \exp[i2\pi(ux+vy)] du dv \end{cases} \quad (22)$$

Comparing Equations (20) and (22), we obtain $$c_u(u,v) = i2\pi u c(u,v) \quad (23)$$

$$c_v(u,v) = i2\pi v c(u,v) \quad (24)$$

If we multiple u in both sides of Equation (23) and v in both sides of Equation (24) and sum them together, we get $$uc_u(u,v) + vc_v(u,v) = i2\pi(u^2+v^2) c(u,v) \quad (25)$$

From Equation (25), we obtain the Fourier expansion coefficients as $$c(u,v) = -i \frac{uc_u(u,v) + vc_v(u,v)}{2\pi(u^2+v^2)} \quad (26)$$

Therefore, the Fourier transform of the wavefront can be obtained as $$c(u,v) = -\frac{i}{2\pi(u^2+v^2)} \left[ u \iint \frac{\partial W(x,y)}{\partial x} \exp[-i2\pi(ux+vy)] + v \iint \frac{\partial W(x,y)}{\partial y} \exp[-i2\pi(ux+vy)] \right] \quad (27)$$

Hence, taking an inverse Fourier transform of Equation (27), we obtained the wavefront as $$W(x,y) = \iint c(u,v) \exp[i2\pi(ux+vy)] du dv. \quad (28)$$

Equation (28) is the final solution for wavefront reconstruction. That is to say, if we know the wavefront slope data, we can calculate the coefficients of Fourier series using Equation (27). With Equation (28), the unknown wavefront can then be reconstructed. In the Hartmann-Shack approach, a set of local wavefront slopes is measured and, therefore, this approach lends itself to the application of Equation (27).

In some cases, however, the preceding wavefront reconstruction approach may be limited to unbounded functions. To obtain a wavefront estimate with boundary conditions (e.g. aperture bound), applicants have discovered that an iterative reconstruction approach is useful. First, the above approach can be followed to provide an initial solution, which gives function values to a square grid larger than the function boundary. This is akin to setting the data points to a small non-zero value as further discussed below. The local slopes of the estimated wavefront of the entire square grid can then be calculated. In the next step, all known local slope data, i.e., the measured gradients from a Hartmann-Shack device, can overwrite the calculated slopes. Based on the updated slopes, the above approach can be applied again and a new estimate of the wavefront can be obtained. This procedure is repeated until either a pre-defined number of iterations is reached or a predefined criterion is satisfied.

Three major algorithms have been used in implementing Fourier reconstruction in WaveScan® software. These algorithms are the basis for implementing the entire iterative Fourier reconstruction. The first algorithm is the iterative Fourier reconstruction itself. The second algorithm is for the calculation of refraction to display in a WaveScan® device. And the third algorithm is for reporting the root-mean-square (RMS) errors.

A. Wavefront Surface Reconstruction

Figure 12:
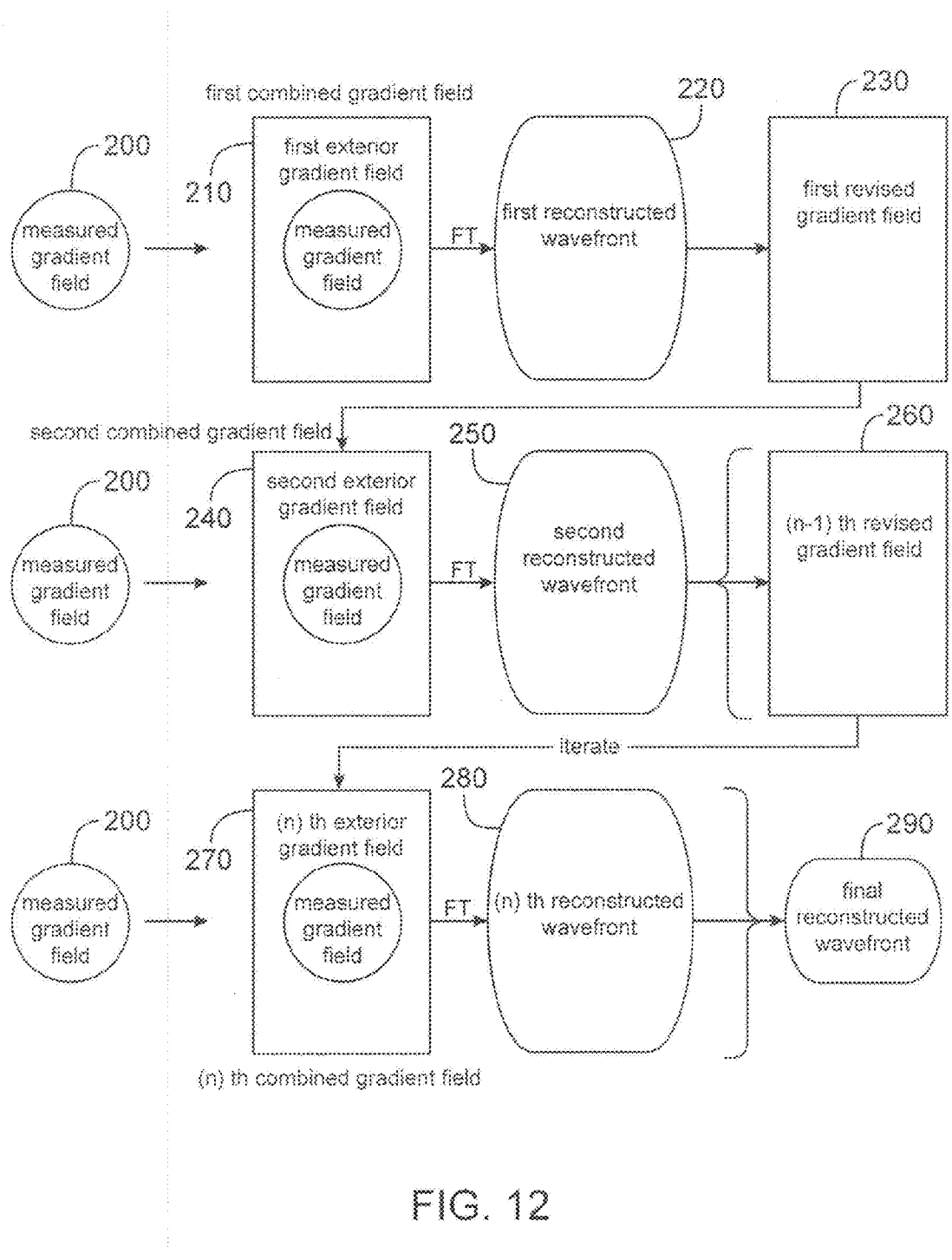
FIG. 12 illustrates an algorithm flow chart according to one embodiment of the present invention.

An exemplary iterative approach is illustrated in FIG. 12. The approach begins with inputting optical data from the optical tissue system of an eye. Often, the optical data will be wavefront data generated by a wavefront measurement device, and will be input as a measured gradient field 200, where the measured gradient field corresponds to a set of local gradients within an aperture. The iterative Fourier transform will then be applied to the optical data to determine the optical surface model. This approach establishes a first combined gradient field 210, which includes the measured gradient field 200 disposed interior to a first exterior gradient field. The first exterior gradient field can correspond to a plane wave, or an unbounded function, that has a constant value W(x,y) across the plane and can be used in conjunction with any aperture.

In some cases, the measured gradient field 200 may contain missing, erroneous, or otherwise insufficient data. In these cases, it is possible to disregard such data points, and only use those values of the measured gradient field 200 that are believed to be good when establishing the combined gradient field 210. The points in the measured gradient field 200 that are to be disregarded are assigned values corresponding to the first exterior gradient field. By applying a Fourier transform, the first combined gradient field 210 is used to derive a first reconstructed wavefront 220, which is then used to provide a first revised gradient field 230.

A second combined gradient field 240 is established, which includes the measured gradient field 200 disposed interior to the first revised gradient field 230. Essentially, the second exterior gradient field is that portion of the first revised gradient field 230 that is not replaced with the measured gradient field 200. In a manner similar to that described above, it is possible to use only those values of the measured gradient field 200 that are believed to be valid when establishing the second combined gradient field 240. By applying a Fourier transform, the second combined gradient field 240 is used to derived a second reconstructed wavefront 250. The second reconstructed wavefront 250, or at least a portion thereof, can be used to provide a final reconstructed wavefront 290. The optical surface model can then be determined based on the final reconstructed wavefront 290.

Optionally, the second combined gradient field can be further iterated. For example, the second reconstructed wavefront 250 can be used to provide an $(n-1)^{th}$ gradient field 260. Then, an $(n)^{th}$ combined gradient field 270 can be established, which includes the measured gradient field 200 disposed interior to the $(n-1)^{th}$ revised gradient field 260. Essentially, the $(n)^{th}$ exterior gradient field is that portion of the $(n-1)^{th}$ revised gradient field 260 that is not replaced with the measured gradient field 200. By applying a Fourier transform, the $(n)^{th}$ combined gradient field 270 is used to derived an $(n)^{th}$ reconstructed wavefront 280. The $(n)^{th}$ reconstructed wavefront 280, or at least a portion thereof, can be used to provide a final reconstructed wavefront 290. The optical surface model can then be determined based on the final reconstructed wavefront 290. In practice, each iteration can bring each successive reconstructed wavefront closer to reality, particularly for the boundary or periphery of the pupil or aperture.

Suppose the Hartmann-Shack device measures the local wavefront slopes that are represented as dZx and dZy, where dZx stands for the wavefront slopes in x direction and dZy stands for the wavefront slopes in y direction. In calculating the wavefront estimates, it is helpful to use two temporary arrays cx and cy to store the local slopes of the estimated wavefront w. It is also helpful to implement the standard functions, such as FFT, iFFT, FFTShift and iFFTShift.

An exemplary algorithm is described below:
1. Set a very small, but non-zero value to data points where there is no data representation in the measurement (from Hartmann-Shack device) (mark=1.2735916e–99)
2. Iterative reconstruction starts for 10 iterations
   a. for the original data points where gradient fields not equal to mark, copy the gradient fields dZx and dZy to the gradient field array cx, and cy
   b. calculate fast Fourier transform (FFT) of cx and cy, respectively
   c. quadrant swapping (FFTShift) of the array obtained in step b
   d. calculate c(u,v) according to Equation (26)
   e. quadrant swapping (iFFTShift) of the array obtained in step d
   f. inverse Fourier transform (iFFT) of the array obtained in step e
   g. calculate updated surface estimate w (real part of the array from step e)
   h. calculate updated gradients from w (derivative of w to x and y)
   i. when the number of iterations equals to 10, finish
3. Calculate average gradients using the estimates from Step 2.h
4. Subtract the average gradients from gradient fields obtained from Step 2.h to take off tip/tilt component
5. Apply Step 2.b-g to obtain the final estimate of wavefront B. Wavefront Refraction Calculation When the wavefront is constructed, calculation of wavefront refraction may be more difficult than when Zernike reconstruction is used. The reason is that once the Zernike coefficients are obtained with Zernike reconstruction, wavefront refraction can be calculated directly with the following formulae:

$$C = -\frac{4\sqrt{6}\sqrt{(c_2^{-2})^2 + (c_2^2)^2}}{R^2}, \quad (29)$$

$$S = -\frac{4\sqrt{3}\,c_2^0}{R^2} - 0.5C, \quad (30)$$

$$\theta = \frac{1}{2}\tan^{-1}\left[\frac{c_2^2}{c_2^{-2}}\right]. \quad (31)$$

where $c_2^{-2}$, $c_2^0$ and $c_2^2$ stand for the three Zernike coefficients in the second order, S stands for sphere, C stands for cylinder and $\theta$ for cylinder axis. However, with Fourier reconstruction, none of the Fourier coefficients are related to classical aberrations. Hence, a Zernike decomposition is required to obtain the Zernike coefficients in order to calculate the refractions using Equations (29)-(31).

Zernike decomposition tries to fit a surface with a set of Zernike polynomial functions with a least squares sense, i.e., the root mean square (RMS) error after the fit will be minimized. In order to achieve the least squares criterion, singular value decomposition (SVD) can be used, as it is an iterative algorithm based on the least squares criterion.

Suppose the wavefront is expressed as a Zernike expansion as $$W(r, \theta) = \sum_{i=0}^{N} c_i Z_i(r, \theta), \quad (32)$$

or in matrix form when digitized as $$W = Z \cdot c, \quad (33)$$

where W is the 2-D M×M matrix of the wavefront map, Z is the M×M×N tensor with N layers of matrix, each represents one surface of a particular Zernike mode with unit coefficient, and c is a column vector containing the set of Zernike coefficients.

Given the known W to solve for c, it is straightforward if we obtain the so-called generalized inverse matrix of Z as $$c = Z^+ \cdot W. \quad (34)$$

A singular value decomposition (SVD) algorithm can calculate the generalized inverse of any matrix in a least squares sense. Therefore, if we have $$Z = U \cdot w \cdot V^T, \quad (35)$$

then the final solution of the set of coefficients will be $$c = V \cdot w^{-1} \cdot U^T \cdot W. \quad (36)$$

One consideration in SVD is the determination of the cutoff eigen value. In the above equation, w is a diagonal matrix with the elements in the diagonal being the eigen values, arranged from maximum to minimum. However, in many cases, the minimum eigen value is so close to zero that the inverse of that value can be too large, and thus it can amplify the noise in the input surface matrix. In order to prevent the problem of the matrix inversion, it may be desirable to define a condition number, r, to be the ratio of the maximum eigen value to the cutoff eigen value. Any eigen values smaller than the cutoff eigen value will not be used in the inversion, or simply put zero as the inverse. In one embodiment, a condition number of 100 to 1000 may be used. In another embodiment, a condition number of 200 may be used.

Once the Zernike decomposition is implemented, calculation of sphere, cylinder as well as cylinder axis can be obtained using Equations (29)-(31). However, the refraction usually is given at a vertex distance, which is different from the measurement plane. Assuming d stands for the vertex distance, it is possible to use the following formula to calculate the new refraction (the cylinder axis will not change):

$$S' = \frac{S}{1 + dS} \quad (37)$$

$$C' = \frac{S + C}{1 + d(S + C)} - S'.$$

The algorithm can be described as the following:
1. Add pre-compensation of sphere and cylinder to the wavefront estimated by iterative Fourier reconstruction algorithm
2. Decomposition of surface from Step 1 to obtain the first five Zernike coefficients
3. Apply Equations (29)-(31) to calculate the refractions
4. Readjust the refraction to a vertex distance using Equation (37)
5. Display the refraction according to cylinder notation C. Wavefront Root-Mean-Square (RMS) Calculation Finally, the wavefront root-mean-square (RMS) error can be calculated. Again, with the use of Zernike reconstruction, calculation of RMS error is straightforward. However, with iterative Fourier reconstruction, it may be more difficult, as discussed earlier. In this case, the Zernike decomposition may be required to calculate the wavefront refraction and thus is available for use in calculating the RMS error.

For RMS errors, three different categories can be used: low order RMS, high order RMS as well as total RMS. For low order RMS, it is possible to use the following formula:

$$lo.r.m.s. = \sqrt{c_3^2 + c_4^2 + c_5^2} \quad (38)$$

where $c_3$, $c_4$ and $c_5$ are the Zernike coefficients of astigmatism, defocus, and astigmatism, respectively. For the high order RMS, it is possible to use the entire wavefront with the formula $$ho.r.m.s. = \sqrt{\frac{\sum_n (v_i - \bar{v})^2}{n}} \quad (39)$$

where $v_i$ stands for the wavefront surface value at the ith location, and $\bar{v}$ stands for the average wavefront surface value within the pupil and n stands for the total number of locations within the pupil. To calculate the total RMS, the following formula may be used.

$$r.m.s. = \sqrt{lo.r.m.s.^2 + ho.r.m.s.^2} \quad (40)$$

The algorithm is
1. For low order RMS, use Equation (38)
2. For high order RMS, use Equation (39)
3. For total RMS, use Equation (40)

D. Convergence

Convergence can be used to evaluate the number of iterations needed in an iterative Fourier transform algorithm. As noted earlier, an iterative Fourier reconstruction algorithm works for unbounded functions. However, in the embodiment described above, Equations (27) and (28) may not provide an appropriate solution because a pupil function was used as a boundary. Yet with an iterative algorithm according to the present invention, it is possible to obtain a fair solution of the bounded function. Table 1 shows the root mean square (RMS) values after reconstruction for some Zernike modes, each having one micron RMS input.

TABLE 1

RMS value obtained from reconstructed wavefront. Real is for a wavefront with combined Zernike modes with total of 1 micron error.

| #iteration | Z3 | Z4 | Z5 | Z6 | Z7 | Z10 | Z12 | Z17 | Z24 | Real |
|---|---|---|---|---|---|---|---|---|---|---|
| 1 | 0.211 | 0.986 | 0.284 | 0.247 | 1.772 | 0.236 | 0.969 | 1.995 | 0.938 | 0.828 |
| 2 | 0.490 | 0.986 | 0.595 | 0.538 | 1.353 | 0.518 | 0.969 | 1.522 | 0.938 | 0.891 |
| 5 | 0.876 | 0.986 | 0.911 | 0.877 | 1.030 | 0.861 | 0.969 | 1.069 | 0.938 | 0.966 |
| 10 | 0.967 | 0.986 | 0.956 | 0.943 | 0.987 | 0.935 | 0.969 | 0.982 | 0.938 | 0.979 |
| 20 | 0.981 | 0.986 | 0.962 | 0.955 | 0.982 | 0.951 | 0.969 | 0.968 | 0.938 | 0.981 |
| 50 | 0.987 | 0.986 | 0.966 | 0.963 | 0.980 | 0.960 | 0.969 | 0.963 | 0.938 | 0.981 |

As an example, FIG. 13 shows the surface plots of wavefront reconstruction of an astigmatism term (Z3) with the iterative Fourier technique with one, two, five, and ten iterations, respectively. For a more realistic case, FIG. 14 shows surface plots of wavefront reconstruction of a real eye with the iterative Fourier technique with one, two, five, and ten iterations, respectively, demonstrating that it converges faster than single asymmetric Zernike terms. Quite clearly 10 iterations appear to achieve greater than 90% recovery of the input RMS errors with Zernike input, however, 5 iterations may be sufficient unless pure cylinder is present in an eye.

E. Extrapolation

Iterative Fourier transform methods and systems can account for missing, erroneous, or otherwise insufficient data points. For example, in some cases, the measured gradient field 200 may contain deficient data. Is these cases, it is possible to disregard such data points when establishing the combined gradient field 210, and only use those values of the measured gradient field 200 that are believed to be good.

A research software program called WaveTool was developed for use in the study. The software was written in C++ with implementation of the iterative Fourier reconstruction carefully tested and results compared to those obtained with Matlab code. During testing, the top row, the bottom row, or both the top and bottom rows were assumed to be missing data so that Fourier reconstruction had to estimate the gradient fields during the course of wavefront reconstruction. In another case, one of the middle patterns was assumed missing, simulating data missing due to corneal reflection. Reconstructed wavefronts with and without pre-compensation are plotted to show the change. At the same time, root mean square (RMS) errors as well as refractions are compared. Each wavefront was reconstructed with 10 iterations.

Only one eye was used in the computation. The original H-S pattern consists of a 15×15 array of gradient fields with a maximum of a 6 mm pupil computable. When data are missing, extrapolation is useful to compute the wavefront for a 6 mm pupil when there are missing data. Table 2 shows the change in refraction, total RMS error as well as surface RMS error (as compared to the one with no missing data) for a few missing-data cases.

The measured gradient field can have missing edges in the vertical direction, because CCD cameras typically are rectangular in shape. Often, all data in the horizontal direction is captured, but there may be missing data in the vertical direction. In such cases, the measured gradient field may have missing top rows, bottom rows, or both.

TABLE 2

Comparison of refraction and RMS for reconstructed wavefront with missing data.

| Case | Rx | Total RMS | RMS Error |
|---|---|---|---|
| No missing data | −2.33DS/−1.02DCx170°@12.5 | 3.77 µm | — |
| Missing top row | −2.33DS/−1.03DCx170°@12.5 | 3.78 µm | 0.0271 µm |
| Missing bottom row | −2.37DS/−0.97DCx169°@12.5 | 3.75 µm | 0.0797 µm |
| Missing top and bottom | −2.37DS/−0.99DCx170°@12.5 | 3.76 µm | 0.0874 µm |
| Missing one point | −2.33DS/−1.02DCx170°@12.5 | 3.77 µm | 0.0027 µm |
| Missing four points | −2.32DS/−1.03DCx170°@12.5 | 3.76 µm | 0.0074 µm |

Figure 15:
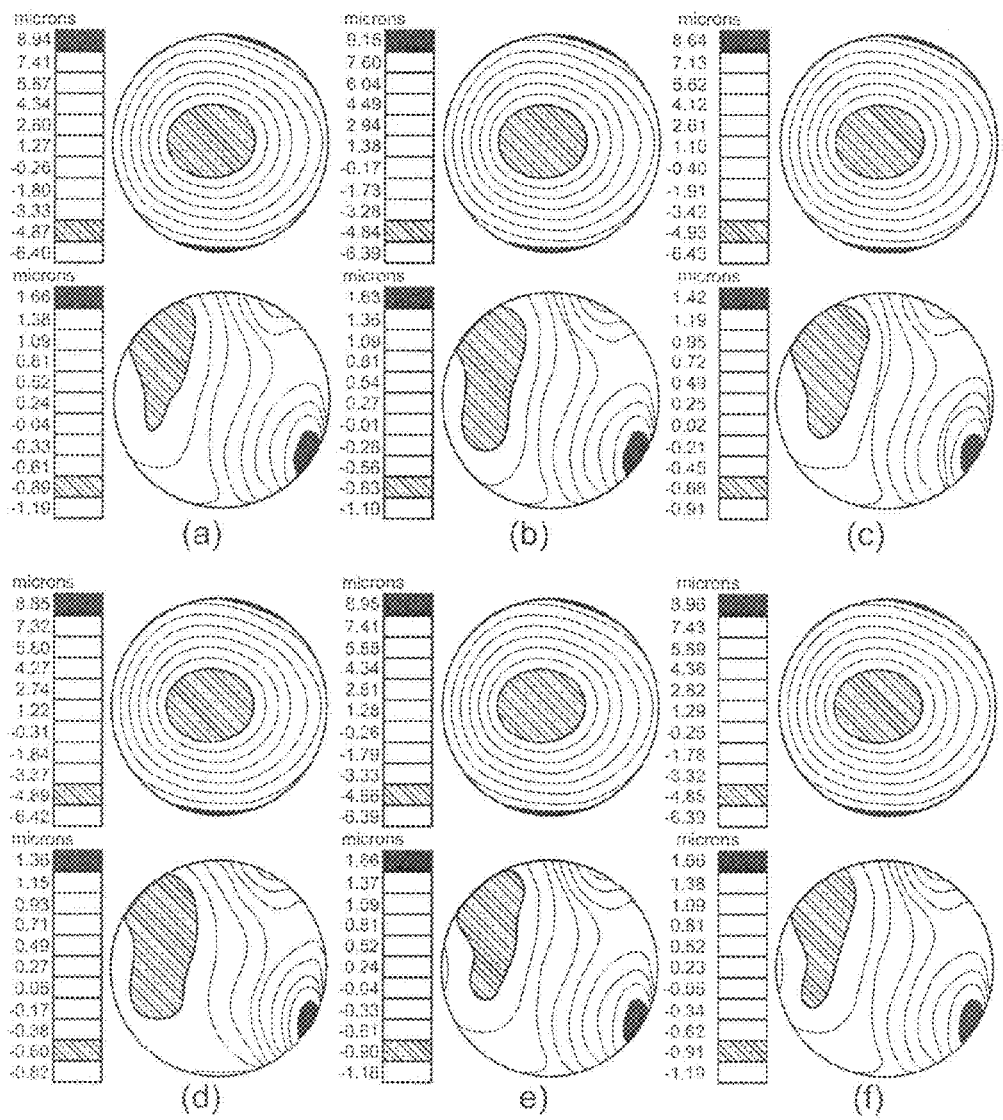
FIG. 15 illustrates a comparison of wavefront maps with or without missing data according to one embodiment of the present invention.

FIG. 15 shows the reconstructed wavefronts with and without pre-compensation for different cases of missing data. The top row shows wavefront with pre-compensation and the bottom row shows wavefront without pre-compensation. The following cases are illustrated: (a) No missing data; (b) missing top row; (c) missing bottom row; (d) missing both top and bottom rows; (e) missing a middle point; (f) missing four points. The results appear to support that missing a small amount of data is of no real concern and that the algorithm is able to reconstruct a reasonably accurate wavefront.

With 10 iterations, the iterative Fourier reconstruction can provide greater than 90% accuracy compared to input data. This approach also can benefit in the event of missing measurement data either inside the pupil due to corneal reflection or outside of the CCD detector.

III. Calculating Estimated Basis Function Coefficients

As noted above, singular value decomposition (SVD) algorithms may be used to calculate estimated Zernike polynomial coefficients based on Zernike polynomial surfaces. Zernike decomposition can be used to calculate Zernike coefficients from a two dimensional discrete set of elevation values. Relatedly, Zernike reconstruction can be used to calculate Zernike coefficients from a two dimensional discrete set of X and Y gradients, where the gradients are the first order derivatives of the elevation values. Both Zernike reconstruction and Zernike decomposition can use the singular value decomposition (SVD) algorithm. SVD algorithms may also be used to calculate estimated coefficients from a variety of surfaces. The present invention also provides additional approaches for calculating estimated Zernike polynomial coefficients, and other estimated basis function coefficients, from a broad range of basis function surfaces.

Wavefront aberrations can be represented with different sets of basis functions, including a wide variety of orthogonal and non-orthogonal basis functions. The present invention is well suited for the calculation of coefficients from orthogonal and non-orthogonal basis function sets alike. Examples of complete and orthogonal basis function sets include, but are not limited to, Zernike polynomials, Fourier series, Chebyshev polynomials, Hermite polynomials, Generalized Laguerre polynomials, and Legendre polynomials. Examples of complete and non-orthogonal basis function sets include, but are not limited to, Taylor monomials, and Seidel and higher-order power series. If there is sufficient relationship between the coefficients of such non-orthogonal basis function sets and Zernike coefficients, the conversion can include calculating Zernike coefficients from Fourier coefficients and then converting the Zernike coefficients to the coefficients of the non-orthogonal basis functions. In an exemplary embodiment, the present invention provides for conversions of expansion coefficients between various sets of basis functions, including the conversion of coefficients between Zernike polynomials and Fourier series.

As described previously, ocular aberrations can be accurately and quickly estimated from wavefront derivative measurements using iterative Fourier reconstruction and other approaches. Such techniques often involve the calculation of Zernike coefficients due to the link between low order Zernike terms and classical aberrations, such as for the calculation of Sphere, Cylinder, and spherical aberrations. Yet Zernike reconstruction can sometimes be less than optimal. Among other things, the present invention provides an FFT-based, fast algorithm for calculating a Zernike coefficient of any term directly from the Fourier transform of an unknown wavefront during an iterative Fourier reconstruction process. Such algorithms can eliminate Zernike reconstruction in current or future WaveScan platforms and any other current or future aberrometers.

Wavefront technology has been successfully applied in objective estimation of ocular aberrations with wavefront derivative measurements, as reported by Jiang et al. in previously incorporated "Objective measurement of the wave aberrations of the human eye with the use of a Hartmann-Shack wave-front sensor," J. Opt. Soc. Am. A 11, 1949-1957 (1994). However, due to the orthogonal nature of Zernike polynomials over a circular aperture, many of the Zernike terms may have very sharp edges along the periphery of the aperture. This can present issues in laser vision correction, because in normal cases ocular aberrations would not have sharp edges on the pupil periphery. As previously discussed here, improved wavefront reconstruction algorithms for laser vision correction have been developed.

As reported by M. Born and E. Wolf in *Principles of optics*, 5$^{th}$ ed. (Pergamon, New York, 1965), in many situations, calculation of the spherocylindrical terms as well as some high order aberrations, such as coma, trefoil, and spherical aberration, can require a Zernike representation due to the link between Zernike polynomials and some low order classical aberrations. Thus, Zernike reconstruction is currently applied for displaying the wavefront map and for reporting the refractions. The present invention provides for improvements over such known techniques. In particular, the present invention provides an approach that allows direct calculation between a Fourier transform of an unknown wavefront and Zernike coefficients. For example, during an iterative Fourier reconstruction from wavefront derivative measurements, a Fourier transform of the wavefront can be calculated. This Fourier transform, together with a conjugate Fourier transform of a Zernike polynomial, can be used to calculate any Zernike coefficient up to the theoretical limit in the data sampling.

A. Wavefront Representation

In doing the theoretical derivation, it is helpful to discuss the representation of wavefront maps in a pure mathematical means, which can facilitate mathematical treatment and the ability to relate wavefront expansion coefficients between two different sets of basis functions.

Let's consider a wavefront $W(Rr,\theta)$ in polar coordinates. It can be shown that the wavefront can be infinitely accurately represented with $$W(Rr, \theta) = \sum_{i=0}^{\infty} a_i G_i(r, \theta), \tag{41}$$

when the set of basis functions $\{G_i(r,\theta)\}$ is complete. The completeness of a set of basis functions means that for any two sets of complete basis functions, the conversion of coefficients of the two sets exists. In Eq. (41), R denotes the radius of the aperture.

If the set of basis function $\{G_i(r,\theta)\}$ is orthogonal, we have $$\iint P(r,\theta)G_i(r,\theta)G_{i'}(r,\theta)d^2r=\delta_{ii'}, \tag{42}$$

where $P(r,\theta)$ denotes the pupil function, and $\delta_{ii'}$ stands for the Kronecker symbol, which equals to 1 only if when i=i'. Multiplying $P(r,\theta)$ $G_i(r,\theta)$ in both sides of Eq. (41), making integrations to the whole space, and with the use of Eq. (42), the expansion coefficient can be written as $$a_i=\iint P(r,\theta)W(Rr,\theta)G_i(r,\theta)d^2r. \tag{43}$$

For other sets of basis functions that are neither complete nor orthogonal, expansion of wavefront may not be accurate. However, even with complete and orthogonal set of basis functions, practical application may not allow wavefront expansion to infinite number, as there can be truncation error. The merit with orthogonal set of basis functions is that the truncation is optimal in the sense of a least squares fit.

B. Zernike Polynomials

Figure 16:
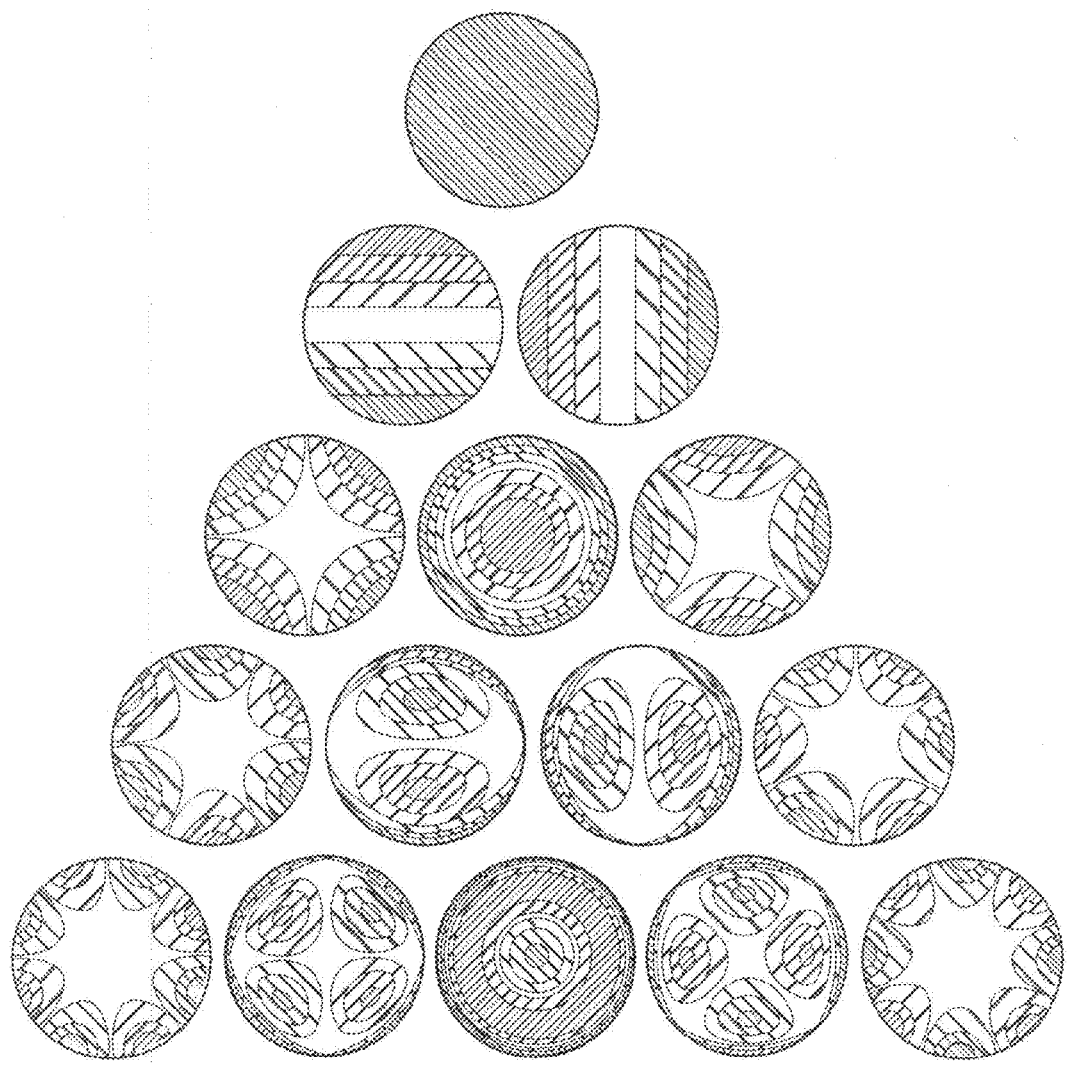
FIG. 16 illustrates a Zernike pyramid that displays the first four orders of Zernike polynomials according to one embodiment of the present invention.

As discussed by R. J. Noll in "Zernike polynomials and atmospheric turbulence," J. Opt. Soc. Am. 66, 207-211 (1976), Zernike polynomials have long been used as wavefront expansion basis functions mainly because they are complete and orthogonal over circular apertures, and they related to classical aberrations. FIG. 16 shows the Zernike pyramid that displays the first four orders of Zernike polynomials. It is possible to define Zernike polynomials as the multiplication of their radial polynomials and triangular functions as $$Z_i(r,\theta)=R_n^m(r)\Phi^m(\theta), \tag{44}$$

where the radial polynomials are defined as $$R_n^m(r) = \sum_{s=0}^{(n-|m|)/2} \frac{(-1)^s \sqrt{n+1}\ (n-s)!}{s![(n+m)/2-s]![(n-m)/2-s]!} r^{n-2s}, \tag{45}$$

and the triangular functions as $$\Phi^m(\theta) = \begin{cases} \sqrt{2}\ \cos|m|\theta & (m > 0) \\ 1 & (m = 0) \\ \sqrt{2}\ \sin|m|\theta & (m < 0). \end{cases} \tag{46}$$

Using both the single-index i and the double-index n and m, the conversion between the two can be written as $$\begin{cases} n = \text{int}(\sqrt{2i+1}) - 1, \\ m = 2i - n(n+2), \\ i = \dfrac{n^2 + 2n + m}{2}. \end{cases} \quad (47)$$

Applying Zernike polynomials to Eq. (43), Zernike coefficient as a function of wavefront can be obtained as $$a_i = \frac{1}{\pi} \int_0^\infty \int_0^{2\pi} P(r) W(Rr, \theta) Z_i(r, \theta) r\, dr\, d\theta. \quad (48)$$

where P(r) is the pupil function defining the circular aperture.

The Fourier transform of Zernike polynomials, can be written as $$U_i(\kappa, \phi) = \frac{(-1)^{n/2}}{\kappa} \sqrt{n+1}\, J_{n+1}(2\pi\kappa) \Theta^m(\phi), \quad (49)$$

and the conjugate Fourier transform of Zernike polynomials can be written as $$V_i(\kappa, \phi) = \frac{(-1)^{n/2+m}}{\kappa} \sqrt{n+1}\, J_{n+1}(2\pi\kappa) \Theta^m(\phi), \quad (49A)$$

where $J_n$ is the nth order Bessel function of the first kind. Another way of calculating the Fourier transform of Zernike polynomials is to use the fast Fourier transform (FFT) algorithm to perform a 2-D discrete Fourier transform, which in some cases can be faster than Eq. (49)

In a related embodiment, wavefront expansion can be calculated as follows. Consider a wavefront defined by a circular area with radius R in polar coordinates, denoted as $W(Rr,\theta)$. Both polar coordinates and Cartesian coordinates can be used to represent 2-D surfaces. If the wavefront is expanded into Zernike polynomials as $$W(Rr, \theta) = \sum_{i=0}^{\infty} c_i Z_i(r, \theta), \quad (Z1)$$

the expansion coefficient $c_i$ can be calculated from the orthogonality of Zernike polynomials as $$c_i = \frac{1}{\pi} \int\!\!\int P(r, \theta) W(Rr, \theta) Z_i(r, \theta) d^2 r, \quad (Z2)$$

where $d^2 r = r\, dr\, d\theta$ and P(r) is the pupil function. The integration in Eq. (Z2) and elsewhere herein can cover the whole space. Zernike polynomials can be defined as $$Z_i(r,\theta) = R_n^m(r) \Phi^m(\theta), \quad (Z3)$$

where n and m denote the radial degree and the azimuthal frequency, respectively, the radial polynomials are defined as $$R_n^m(r) = \sum_{s=0}^{(n-|m|)/2} \frac{(-1)^s \sqrt{n+1}\,(n-s)!}{s!\,[(n+m)/2 - s]!\,[(n-m)/2 - s]!} r^{n-2s} \quad (Z4)$$

and the triangular functions as $$\Theta^m(\theta) = \begin{cases} \sqrt{2} \cos|m|\theta & (m > 0) \\ 1 & (m = 0) \\ \sqrt{2} \sin|m|\theta & (m < 0) \end{cases} \quad (Z5)$$

Often, the radial degree n and the azimuthal frequency m must satisfy that n−m is even. In addition, m goes from −n to n with a step of 2. If $U_i(k,\phi)$ and $V_i(k,\phi)$ are denoted as Fourier transform and conjugate Fourier transform of Zernike polynomials, respectively, as $$U_i(k,\theta) = \int_{-\infty}^{\infty}\int_{-\infty}^{\infty} P(r) Z_i(r,\theta) \exp(-j2\pi k \cdot r) d^2 r, \quad (Z6)$$

$$V_i(k,\phi) = \int_{-\infty}^{\infty}\int_{-\infty}^{\infty} P(r) Z_i(r,\theta) \exp(j2\pi k \cdot r) d^2 r, \quad (Z7)$$

where $j^2 = -1$, r and k stand for the position vectors in polar coordinates in spatial and frequency domains, respectively, it can be shown that $$U_i(\kappa, \phi) = \frac{(-1)^{n/2+|m|}}{\kappa} \sqrt{n+1}\, J_{n+1}(2\pi\kappa) \Theta^m(\phi), \quad (Z8)$$

$$V_i(\kappa, \phi) = \frac{(-1)^{n/2}}{\kappa} \sqrt{n+1}\, J_{n+1}(2\pi\kappa) \Theta^m(\phi). \quad (Z9)$$

A conjugate Fourier transform of Zernike polynomials can also be represented in discrete form, as $$V_i(k, \phi) = N \sum_{i=0}^{N^2-1} P(r) Z_i(r, \theta) \exp\left[j \frac{2\pi}{N} k \cdot r\right] \quad (Z7A)$$

In Eqs. (Z8) and (Z9), $J_n$ stands for the nth order Bessel function of the first kind. Note that the indexing of functions U and V is the same as that of Zernike polynomials. In deriving these equations, the following identities $$\cos(z\cos\theta) = J_0(z) + 2 \sum_{i=1}^{\infty} (-1)^i J_{2i}(z) \cos(2i\theta), \quad (Z10)$$

$$\sin(z\cos\theta) = 2 \sum_{i=0}^{\infty} (-1)^i J_{2i+1}(z) \cos[(2i+1)\theta], \quad (Z11)$$

and the integration of Zernike radial polynomials $$\int_0^1 R_n^m(r) J_{|m|}(kr) r\, dr = (-1)^{(n-|m|)/2} \sqrt{n+1}\, \frac{J_{n+1}(k)}{k}, \quad (Z12)$$

were used. With the use of the orthogonality of Bessel functions, $$\int_0^\infty J_{\nu+2n+1}(t)J_{\nu+2m+1}(t)t^{-1}dt = \frac{\delta_{mn}}{2(\nu+2n+1)}, \quad (Z13)$$

it can be shown that $U_i(k,\phi)$ and $V_i(k, \phi)$ are orthogonal over the entire space as $$\frac{1}{\pi}\int\int U_i(k, \phi)V_{i'}(k, \phi)kdkd\phi = \delta_{ii'}. \quad (Z14)$$

Similarly, the wavefront can also be expanded into sinusoidal functions. Denote $\{F_i(r,\theta)\}$ as the set of Fourier series. The wave-front $W(Rr,\theta)$ can be expressed as $$W(Rr, \theta) = \sum_{i=1}^{N^2} a_i F_i(r, \theta) \quad (Z15)$$

$$= \sum_{i=1}^{N^2} a_i(k, \phi)\exp\left(j\frac{2\pi}{N}k \cdot r\right),$$

where $a_i$ is the ith coefficient of $F_i(r,\theta)$. Note that the ith coefficient $a_i$ is just one value in the matrix of coefficients $a_i(k,\phi)$. Furthermore, $a_i$ is a complex number, as opposed to a real number in the case of a Zernike coefficient. When N approaches infinity, Eq. (Z15) can be written as $$W(Rr,\theta) = \iint a(k,\phi)\exp(j2\pi k \cdot r)d^2k, \quad (Z16)$$

where $d^2k = kdkd\phi$. The orthogonality of the Fourier series can be written as $$\iint F_i(r,\theta)F_{i'}{}^*(r,\theta)d^2r = \delta_{ii'}, \quad (Z17)$$

where $F^*{}_i(r,\theta)$ is the conjugate of $F_i(r,\theta)$. With the use of Eqs. (16) and (17), the matrix of expansion coefficients $a(k,\phi)$ can be written as $$a(k,\theta) = \iint W(Rr,\theta)\exp(-j2\pi k \cdot r)d^2r. \quad (Z18)$$

C. Fourier Series

Taking the wavefront in Cartesian coordinates in square apertures, represented as $W(x,y)$, we can express the wavefront as a linear combination of sinusoidal functions as $$W(x, y) = \sum_{i=0}^{N^2} c_i F_i(x, y) \quad (50)$$

$$= \sum_{u=0}^{N-1}\sum_{v=0}^{N-1} c(u, v)\exp\left[j\frac{2\pi}{N}(ux + vy)\right]$$

$$= N \times IFT[c(u, v)]$$

where $j^2 = -1$, IFT stands for inverse Fourier transform, and $F_i(x,y)$ stands for the Fourier series. It should be noted that Fourier series are complete and orthogonal over rectangular apertures. Representation of Fourier series can be done with either single-index or double-index. Conversion between the single-index i and the double-index u and v can be performed with $$u = \begin{cases} i - n^2 & (i - n^2 < n) \\ n & (i - n^2 \geq n), \end{cases} \quad (51)$$

$$v = \begin{cases} n & (i - n^2 < n) \\ n^2 + 2n - i & (i - n^2 \geq n). \end{cases}$$

where the order n can be calculated with $$n = \begin{cases} \text{int}(\sqrt{i}) \\ \max(u, v) \end{cases} \quad (52)$$

Figure 17:
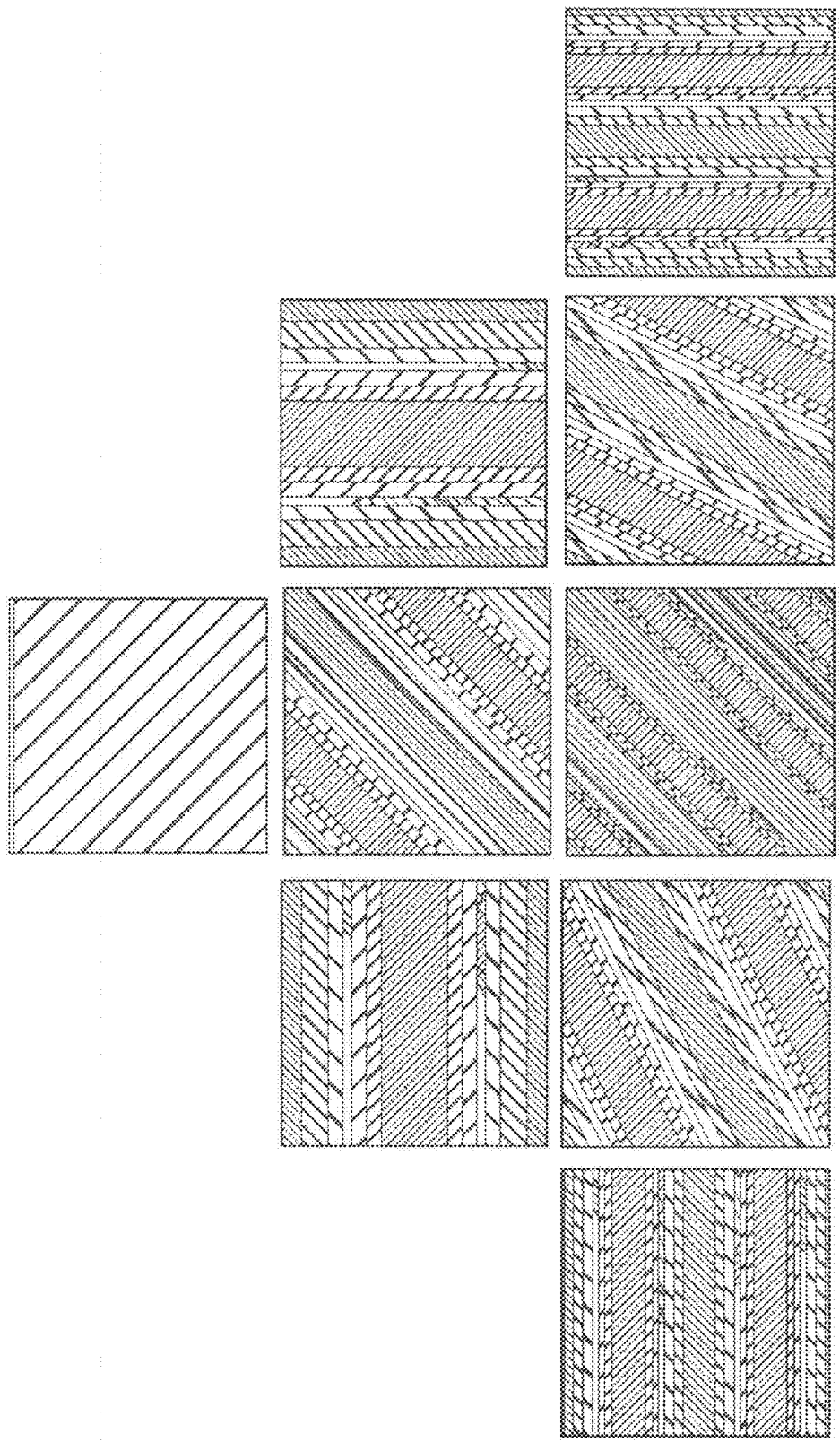
FIG. 17 illustrates a Fourier pyramid corresponding to the first two orders of Fourier series according to one embodiment of the present invention.

From Eq. (50), the coefficients $c(u,v)$ can be written as $$c(u, v) = \sum_{x=0}^{N-1}\sum_{y=0}^{N-1} W(x, y)\exp\left[-j\frac{2\pi}{N}(ux + vy)\right] \quad (53)$$

$$= \frac{1}{N} \times FT[W(x, y)].$$

where FT stands for Fourier transform. FIG. 17 shows a Fourier pyramid corresponding to the first two orders of Fourier series.

D. Taylor Monomials

Figure 18:
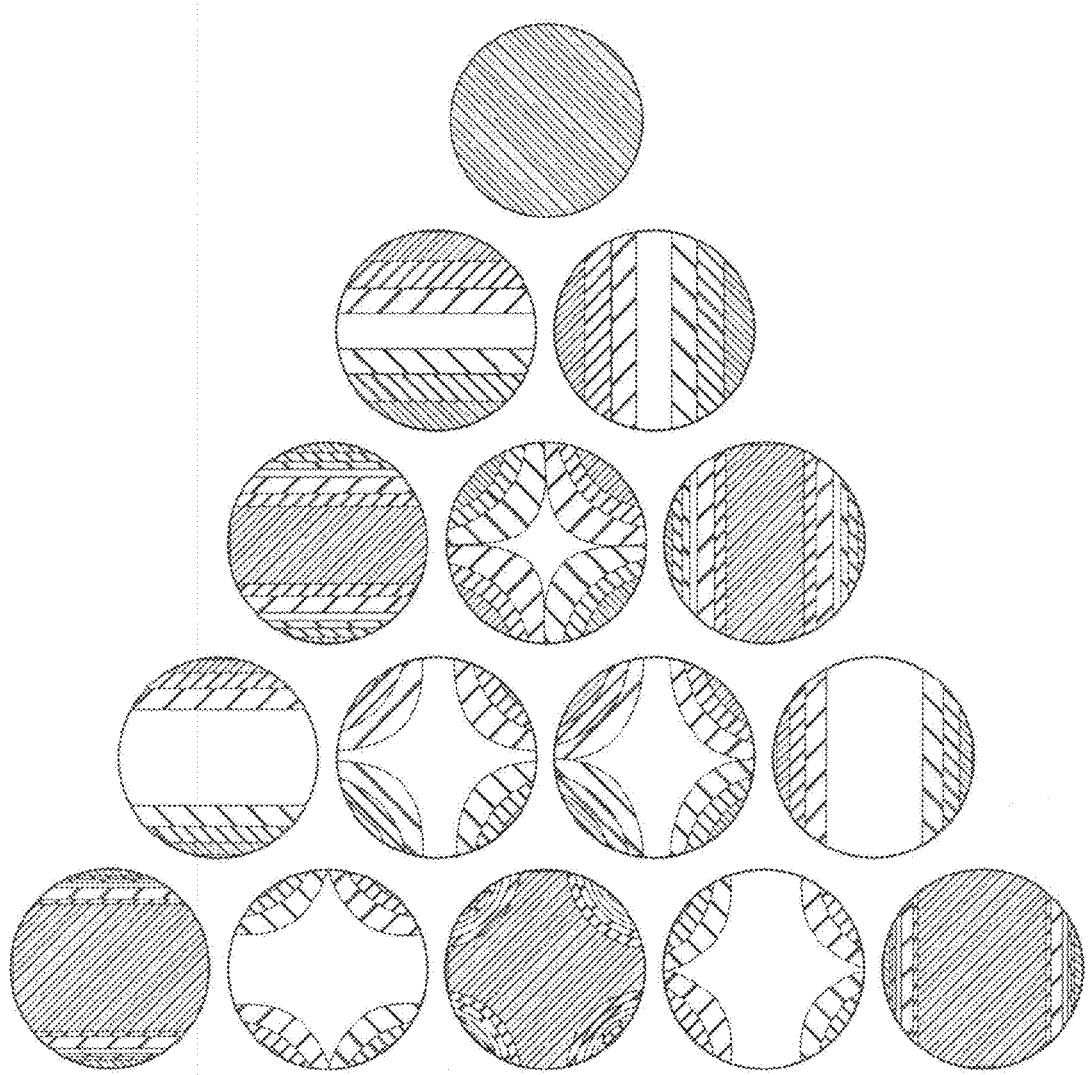
FIG. 18 illustrates a Taylor pyramid that contains the first four orders of Taylor monomials according to one embodiment of the present invention.

Taylor monomials are discussed by H. C. Howland and B. Howland in "A subjective method for the measurement of monochromatic aberrations of the eye," J. Opt. Soc. Am. 67, 1508-1518 (1977). Taylor monomials can be useful because they are complete. But typically they are not orthogonal. Taylor monomials can be defined as $$T_i(r,\theta) = T_p{}^q(r,\theta) = r^p \cos^q\theta \sin^{p-q}\theta, \quad (54)$$

where p and q are the radial degree and azimuthal frequency, respectively. FIG. 18 shows the Taylor pyramid that contains the first four orders of Taylor monomials. The present invention contemplates the use of Taylor monomials, for example, in laser vision correction.

E. Conversion Between Fourier Coefficients and Zernike Coefficients

The conversion of the coefficients between two complete sets of basis functions is discussed above. This subsection derives the conversion between Zernike coefficients and Fourier coefficients.

Starting from Eq. (48), if we re-write the wavefront in Cartesian coordinates, represented as $W(x,y)$ to account for circular aperture boundary, we have $$a_i = \frac{1}{\pi}\int_{-\infty}^{\infty}\int_{-\infty}^{\infty} P(x, y)W(x, y)Z_i(x, y)dxdy. \quad (55)$$

In Eq. (50), if we set N approach infinity, we get $$W(x,y) = \int_{-\infty}^{\infty}\int_{-\infty}^{\infty} c(x,y)\exp[j2\pi(ux+vy)]dudv. \quad (56)$$

With the use of Eq. (56), Eq. (54) can be written as $$a_i = \frac{1}{\pi}\int_{-\infty}^{\infty}\int_{-\infty}^{\infty} P(x, y)W(x, y)Z_i(x, y)dxdy \quad (57)$$

$$= \frac{1}{\pi}\int_{-\infty}^{\infty}\int_{-\infty}^{\infty} P(x, y)$$

-continued $$\int_{-\infty}^{\infty}\int_{-\infty}^{\infty} c(u,v)\exp[j2\pi(ux+vy)]dudv Z_i(x,y)dxdy$$

$$= \frac{1}{\pi}\int_{-\infty}^{\infty}\int_{-\infty}^{\infty} P(x,y)Z_i(x,y)\exp[j2\pi(ux+vy)]dxdy \quad 5$$

$$\int_{-\infty}^{\infty}\int_{-\infty}^{\infty} c(u,v)dudv.$$

Now, since Zernike polynomials are typically applied to circular aperture, we know $$P(x,y)Z_i(x,y)=Z_i(x,y). \quad (58)$$

So we have the first part in Eq. (57) as the conjugate Fourier transform of Zernike polynomials $$V_i(u,v)=\int_{-\infty}^{\infty}\int_{-\infty}^{\infty} P^2(x,y)\exp[j2\pi(ux+vy)]dxdy. \quad (59)$$

Hence, Eq. (57) can finally be written in an analytical format as $$a_i = \frac{1}{\pi}\int_{-\infty}^{\infty}\int_{-\infty}^{\infty} c(u,v)V_i(u,v)dudv. \quad (60)$$

Eq. (60) can be written in discrete numerical format as $$a_i = \frac{1}{\pi}\sum_{u=0}^{N-1}\sum_{v=0}^{N-1} c(u,v)V_i(u,v). \quad (61)$$

Equation (61) can be used to calculate the Zernike coefficients directly from the Fourier transform of wavefront maps, i.e., it is the sum, pixel by pixel, in the Fourier domain, the multiplication of the Fourier transform of the wavefront and the conjugate Fourier transform of Zernike polynomials, divided by $\pi$. Of course, both $c(u,v)$ and $V_i(u,v)$ are complex matrices. Here, $c(u,v)$ can represent a Fourier transform of an original unknown surface, and $V_i(u,v)$ can represent a conjugate Fourier transform of Zernike polynomials, which may be calculated analytically or numerically.

In another embodiment, conversion between Fourier coefficients and Zernike coefficients can be calculated as follows. To relate Zernike coefficients and Fourier coefficients, using Eq. (Z16) and (Z17) results in $$c_i = \frac{1}{\pi}\int\int P(r)W(Rr,\theta)Z_i(r,\theta)dr \quad (Z19)$$

$$= \frac{1}{\pi}\int\int a(k,\phi)d^2k \int\int P(r)Z_i(r,\theta)\exp(j2\pi k\cdot r)d^2r$$

$$= \frac{1}{\pi}\int\int a(k,\phi)V_i(k,\phi)d^2k.$$

Equation (Z19) gives the formula to convert Fourier coefficients to Zernike coefficients. In a discrete form, Eq. (Z19) can be expressed as $$c_i = \frac{1}{\pi}\sum_{l=0}^{N^2-1} a_l(k,\phi)V_l(k,\phi). \quad (Z20)$$

Because Zernike polynomials are typically supported within the unit circle, $Z_i(r,\theta)=P(r)Z_i(r,\theta)$. Taking this into account, inserting Eq. (Z1) into Eq. (Z18) results in $$a(k,\phi) = \int\int \sum_{i=0}^{\infty} c_i Z_i(r,\theta)\exp(-j2\pi k\cdot r)d^2r \quad (Z21)$$

$$= \sum_{i=0}^{\infty} c_i \int\int P(r)Z_i(r,\theta)\exp(-j2\pi k\cdot r)d^2r$$

$$= \sum_{i=0}^{\infty} c_i U_i(k,\phi).$$

Equation (Z21) gives the formula to convert Zernike coefficients to Fourier coefficients. It applies when the wavefront under consideration is bound by a circular aperture. With this restriction, Eq. (Z21) can also be derived by taking a Fourier transform on both sides of Eq. (Z1). This boundary restriction has implications in iterative Fourier reconstruction of the wavefront.

F. Conversion Between Zernike Coefficients and Taylor Coefficients

From Eq. (41) using Zernike polynomials, we have $$a_i = \frac{1}{\pi}\int\int P(r)W(Rr,\theta)Z_i(r,\theta)d^2r. \quad (62)$$

Using Eq. (54) and some arithmatics, Eq. (62) becomes $$a_i = \frac{1}{\pi}\int\int P(r)\sum_{j=0}^{\infty} b_j r^p \cos^q\theta\sin^{p-q}\theta Z_i(r,\theta)d^2r \quad (63)$$

$$= \frac{1}{\pi}\sum_{j=0}^{\infty} b_j \int_0^1 R_n^m(r)r^p r dr \int_0^{2\pi}\Theta^m(\theta)\cos^q\theta\sin^{p-q}\theta d\theta$$

$$= \frac{1}{\pi}\sum_{j=0}^{\infty} b_j \sum_{s=0}^{(n-|m|)/2} \frac{(-1)^s\sqrt{n+1}\,(n-s)!}{s![(n+m)/2-s]![(n-m)/2-s]!}$$

$$\int_0^1 r^{n+p-2s+1}dr \times$$

$$\int_0^{2\pi}\Theta^m(\theta)\cos^q\theta\sin^{p-q}\theta d\theta$$

$$= \frac{1}{\pi}\sum_{j=0}^{\infty} b_j \sum_{s=0}^{(n-|m|)/2}$$

$$\frac{(-1)^s\sqrt{n+1}\,(n-s)!}{s!(n+p-2s+2)[(n+m)/2-s]![(n-m)/2-s]!} \times$$

$$\int_0^{2\pi}\Theta^m(\theta)\cos^q\theta\sin^{p-q}\theta d\theta$$

Using the following identity $$\cos^q\theta = \frac{1}{2^q}\sum_{t=0}^{t}\frac{q!}{t!(q-t)!}\cos(q-2t)\theta, \quad (64)$$

the integration term in Eq. (63) can be calculated as $$\int_0^{2\pi} \Theta^m(\theta)\cos^q\theta\sin^{p-q}\theta d\theta = \qquad (65)$$

$$\frac{\pi(p-q)!q!}{2^p}\sum_{t=0}^{q}\frac{1}{t!(q-t)!}\sum_{t'=0}^{p-q}\frac{g(p,q,m,t,t')}{(t')!(p-q-t')!},$$

where the function g(p,q,m,t,t') can be written as $$g(p,q,m,t,t') = \qquad (66)$$

$$\begin{cases} \sqrt{2}\,(-1)^{(p-q)/2+t'}[\delta_{(p-2t-2t')m} + \delta_{(p-2q+2t-2t')m}] & (m>0) \\ (-1)^{(p-q)/2+t'}[\delta_{(p-2t-2t')0} + \delta_{(p-2q+2t-2t')0}] & (m=0) \\ \sqrt{2}\,(-1)^{(p-q-1)/2+t'}[\delta_{(p-2q+2t-2t')|m|} + \delta_{(2q-p-2t+2t')|m|}] & (m<0), \end{cases}$$

where $\delta$ is the Kronecker symbol and p–q is even when m>=0 and odd otherwise. Therefore the conversion matrix from Taylor monomials to Zernike polynomials can be written as $$d_n^m = \qquad (67)$$

$$\sum_{j=0}^{\infty} b_j \sum_{s=0}^{(n-|m|)/2} \frac{(-1)^s\sqrt{n+1}\,(n-s)!}{s!(n+p-2s+2)[(n+m)/2-s]![(n-m)/2-s]!} \times$$

$$\frac{(p-q)!q!}{2^p}\sum_{t=0}^{q}\frac{1}{t!(q-t)!}\sum_{t'=0}^{p-q}\frac{g(p,q,m,t,t')}{(t')!(p-q-t')!}.$$

Starting from Zernike polynomials with the case m>=0, we have $$Z_i(r,\theta) = \sum_{s=0}^{(n-|m|)/2}\frac{(-1)^s\sqrt{(2-\delta_{m0})(n+1)}\,(n-s)!}{s![(n+m)/2-s]![(n-m)/2-s]!}r^{n-2s}\cos m\theta. \qquad (68)$$

Using the following identities $$\cos m\theta = \sum_{t=0}^{t_0}\frac{(-1)^t m!}{(2t)!(m-2t)!}\cos^{m-2t}\theta\sin^{2t}\theta, \qquad (69)$$

$$\sin m\theta = \sum_{t=0}^{t_0}\frac{(-1)^t m!}{(2t+1)!(m-2t-1)!}\cos^{m-2t-1}\theta\sin^{2t+1}\theta.$$

where $$t_0 = \begin{cases} \text{int}[(|m|)/2] & (m \geq 0) \\ \text{int}[(|m|-1)/2] & (m < 0) \end{cases} \qquad (70)$$

and $$1 = (\sin^2\theta + \cos^2\theta)^{(p-|m|)/2} \qquad (71)$$

$$= \sum_{t'=0}^{(p-|m|)/2}\frac{[(p-|m|)/2]!}{(t')![(p-|m|)/2-t']!}\cos^{2t'}\theta\sin^{(p-|m|)/2-t'}$$

we finally obtain the following conversion formula as $$b_i = \sum_{j=0}^{\infty} a_j \frac{(-1)^{(n-p)/2}\sqrt{n+1}\,[(n+p)/2]!|m|!}{[(p+|m|)/2]![(n-p)/2]!} \times \qquad (72)$$

$$\sum_{t=0}^{t_0}\sum_{t'=0}^{(p-|m|)/2}\frac{(-1)^t\sqrt{2-\delta_{m0}}\,f(m,t)}{(2t)!(t')![(p-|m|)/2-t']!}$$

where the function f(m,t) can be expressed as $$f(m,t) = \begin{cases} \dfrac{1}{(|m|-2t)!} & t+t' = (p-q)/2; m \geq 0 \\ \dfrac{1}{(|m|-2t-1)!} & t+t' = (p-q-1)/2; m < 0 \\ 0 & \text{otherwise} \end{cases} \qquad (73)$$

In arriving at Eq. (72), n>=p, and both n–p and p–|m| are even. As a special case, when m=0, we have $$b_p^q = \sum_{n=0}^{\infty} a_n^0 \frac{(-1)^{(n-p)/2}\sqrt{n+1}\,[(n+p)/2]!}{[(n-p)/2]![(p-q)/2]!(p/2)!(q/2)!}. \qquad (74)$$

The conversion of Zernike coefficients to and from Taylor coefficients can be used to simulate random wavefronts. Calculation of Taylor coefficients from Fourier coefficients can involve calculation of Zernike coefficients from Fourier coefficients, and conversion of Zernike coefficients to Taylor coefficients. Such an approach can be faster than using SVD to calculate Taylor coefficients. In a manner similar to Zernike decomposition, it is also possible to use SVD to do Taylor decomposition.

IV. Wavefront Estimation from Slope Measurements

Wavefront reconstruction from wavefront slope measurements has been discussed extensively in the literature. As noted previously, this can be accomplished by zonal and modal approaches. In the zonal approach, the wavefront is estimated directly from a set of discrete phase-slope measurements; whereas in the modal approach, the wavefront is expanded into a set of orthogonal basis functions and the coefficients of the set of basis functions are estimated from the discrete phase-slope measurements. Here, modal reconstruction with Zernike polynomials and Fourier series is discussed.

A. Zernike Reconstruction

Substituting the Zernike polynomials in Eq. (44) into Eq. (41), we obtain $$W(Rr,\theta) = \sum_{i=1}^{N} a_i Z_i(r,\theta). \qquad (75)$$

Taking derivatives of both sides of Eq. (75) to x, and to y, respectively, we get $$\frac{\partial W(Rr, \theta)}{\partial x} = \sum_{i=1}^{N} a_i \frac{\partial Z_i(r, \theta)}{\partial x} \tag{76}$$

$$\frac{\partial W(Rr, \theta)}{\partial y} = \sum_{i=1}^{N} a_i \frac{\partial Z_i(r, \theta)}{\partial y}$$

Suppose we have k measurement points in terms of the slopes in x and y direction of the wavefront, Eq. (76) can be written as a matrix form as $$\begin{bmatrix} \frac{\partial W_1(x, y)}{\partial x} \\ \frac{\partial W_1(x, y)}{\partial y} \\ \frac{\partial W_2(x, y)}{\partial x} \\ \frac{\partial W_2(x, y)}{\partial y} \\ \vdots \\ \frac{\partial W_k(x, y)}{\partial x} \\ \frac{\partial W_k(x, y)}{\partial y} \end{bmatrix} = \begin{bmatrix} \left(\frac{\partial Z_1(x, y)}{\partial x}\right)_1 & \left(\frac{\partial Z_2(x, y)}{\partial x}\right)_1 & \cdots & \left(\frac{\partial Z_N(x, y)}{\partial x}\right)_1 \\ \left(\frac{\partial Z_1(x, y)}{\partial y}\right)_1 & \left(\frac{\partial Z_2(x, y)}{\partial y}\right)_1 & \cdots & \left(\frac{\partial Z_N(x, y)}{\partial y}\right)_1 \\ \left(\frac{\partial Z_1(x, y)}{\partial x}\right)_2 & \left(\frac{\partial Z_2(x, y)}{\partial x}\right)_2 & \cdots & \left(\frac{\partial Z_N(x, y)}{\partial x}\right)_2 \\ \left(\frac{\partial Z_1(x, y)}{\partial y}\right)_2 & \left(\frac{\partial Z_2(x, y)}{\partial y}\right)_2 & \cdots & \left(\frac{\partial Z_N(x, y)}{\partial y}\right)_2 \\ \vdots & \vdots & \ddots & \vdots \\ \left(\frac{\partial Z_1(x, y)}{\partial x}\right)_k & \left(\frac{\partial Z_2(x, y)}{\partial x}\right)_k & \cdots & \left(\frac{\partial Z_N(x, y)}{\partial x}\right)_k \\ \left(\frac{\partial Z_1(x, y)}{\partial y}\right)_k & \left(\frac{\partial Z_2(x, y)}{\partial y}\right)_k & \cdots & \left(\frac{\partial Z_N(x, y)}{\partial y}\right)_k \end{bmatrix} \begin{bmatrix} a_1 \\ a_2 \\ \vdots \\ a_N \end{bmatrix} \tag{77}$$

Equation (77) can also be written as another form as $$S = ZA, \tag{78}$$

where S stands for the wavefront slope measurements, Z stands for the Zernike polynomials derivatives, and A stands for the unknown array of Zernike coefficients.

Solution of Eq. (78) is in general non-trivial. Standard method includes a singular value decomposition (SVD), which in some cases can be slow and memory intensive.

B. Iterative Fourier Reconstruction

Let's start from Eq. (50) in analytical form $$W_s(x,y) = \iint c(u,v)\exp[j2\pi(ux+vy)]dudv, \tag{79}$$

where c(u,v) is the matrix of expansion coefficients. Taking partial derivative to x and y, respectively, in Equation (79), we have $$\begin{cases} \frac{\partial W(x, y)}{\partial x} = j2\pi \iint uc(u, v)\exp[j2\pi(ux + vy)]dudv \\ \frac{\partial W(x, y)}{\partial y} = j2\pi \iint vc(u, v)\exp[j2\pi(ux + vy)]dudv \end{cases} \tag{80}$$

Denote $c_u$ to be the Fourier transform of x-derivative of $W_s(x,y)$ and $c_v$ to be the Fourier transform of y-derivative of $W_s(x,y)$. From the definition of Fourier transform, we have $$\begin{cases} c_u(u, v) = \iint \frac{\partial W_s(x, y)}{\partial x}\exp[-j2\pi(ux + vy)]dxdy \\ c_v(u, v) = \iint \frac{\partial W_s(x, y)}{\partial y}\exp[-j2\pi(ux + vy)]dxdy \end{cases} \tag{81}$$

Equation (81) can also be written in the inverse Fourier transform format as $$\begin{cases} \frac{\partial W_s(x,y)}{\partial x} = \iint c_u(u, v)\exp[j2\pi(ux + vy)]dudv \\ \frac{\partial W_s(x,y)}{\partial y} = \iint c_v(u, v)\exp[j2\pi(ux + vy)]dudv \end{cases} \tag{82}$$

Comparing Equations (80) and (82), we obtain $$c_u(u,v) = j2\pi u c(u,v) \tag{83}$$

$$c_v(u,v) = j2\pi v c(u,v) \tag{84}$$

If we multiple u in both sides of Equation (83) and v in both sides of Equation (84) and sum them together, we get $$uc_u(u,v) + vc_v(u,v) = j2\pi(u^2+v^2)c(u,v). \tag{85}$$

From Equation (72), we obtain the Fourier expansion coefficients as $$c(u, v) = -j\frac{uc_u(u, v) + vc_v(u, v)}{2\pi(u^2 + v^2)} \tag{86}$$

Therefore, the Fourier transform of wavefront can be obtained as $$c(u, v) = -\frac{j}{2\pi(u^2 + v^2)}\left[u \iint \frac{\partial W_s(x, y)}{\partial x}\exp[-j2\pi(ux + vy)] + v \iint \frac{\partial W_s(x, y)}{\partial y}\exp[-j2\pi(ux + vy)]\right] \tag{87}$$

Hence, taking an inverse Fourier transform of Equation (87), we obtained the wavefront as $$W(x,y) = \iint c(u,v)\exp[j2\pi(ux+vy)]dudv. \tag{88}$$

Equation (86) applies to a square wavefront W(x,y), which covers the square area including the circular aperture defined by R. To estimate the circular wavefront W(Rr,θ) with wavefront derivative measurements existing within the circular aperture, the boundary condition of the wavefront can be applied, which leads to an iterative Fourier transform for the reconstruction of the wavefront. Equation (88) is the final solution for wavefront reconstruction. That is to say, if we know the wavefront slope data, we can calculate the coefficients of Fourier series using Equation (87). With Equation (88), the unknown wavefront can then be reconstructed. Equation (87) can be applied in a Hartmann-Shack approach, as a Hartmann-Shack wavefront sensor measures a set of local wavefront slopes. This approach of wavefront reconstruction applies to unbounded functions. Iterative reconstruction approaches can be used to obtain an estimate of wavefront with boundary conditions (circular aperture bound). First, the above approach can provide an initial solution, which gives function values to a square grid larger than the function boundary. The local slopes of the estimated wavefront of the entire square grid can then be calculated. In the next step, all known local slope data, i.e., the measured gradients from Hartmann-Shack device, can overwrite the calculated slopes. Based on the updated slopes, the above approach can be applied again and a new estimate of wavefront can be obtained. This procedure is done until either a pre-defined number of iterations is reached or a predefined criterion is satisfied.

C. Zernike Decomposition

In some cases, a Zernike polynomials fit to a wavefront may be used to evaluate the low order aberrations in the wavefront. Starting from Eq. (75), if we re-write it as matrix format, it becomes $$W = ZA, \quad (89)$$

where W stands for the wavefront, Z stands for Zernike polynomials, and A stands for the Zernike coefficients. Solution of A from Eq. (89) can be done with a standard singular value decomposition (SVD) routine. However, it can also be done with Fourier decomposition. Substituting Eq. (53) into Eq. (60), the Zernike coefficients can be solved as $$a_i = \frac{1}{N\pi} \sum_{u=0}^{N-1} \sum_{v=0}^{N-1} FT[W(x, y)] Z_i(u, v). \quad (90)$$

In Eq. (90), any of the Zernike coefficients can be calculated individually by multiplying the Fourier transform of the wavefront with the inverse Fourier transform of the particular Zernike polynomials and sum up all the pixel values, divided by $N\pi$. With FFT algorithm, realization of Eq. (90) is extremely fast, and in many cases faster than the SVD algorithm.

IV. Simulation and Discussion of Results

A. Examples

The first example is to prove Eq. (61) with a wavefront only containing Z6

$$W(Rr, \theta) = a_3^{-1} \sqrt{8}(3r^3 - 2r) \sin \theta. \quad (91)$$

The Fourier transform of the wavefront $W(Rr, \theta)$ can be calculated as $$c(k, \phi) = j\sqrt{8} \sin\phi \frac{J_4(2\pi k)}{k}. \quad (92)$$

Therefore, the right hand side of Eq. (61) can be expressed as $$\frac{1}{\pi} \int \int c(k, \phi) V_3^{-1}(k, \phi) d^2 k = \quad (93)$$

$$\frac{8 a_3^{-1}}{\pi} \int_0^\infty \left[\frac{J_4(2\pi k)}{k}\right]^2 k \, dk \int_0^{2\pi} \sin^2\phi \, d\phi = a_3^{-1}$$

which equals to the left hand side of Eq. (61), hence proving Eq. (61).

Figure 19:
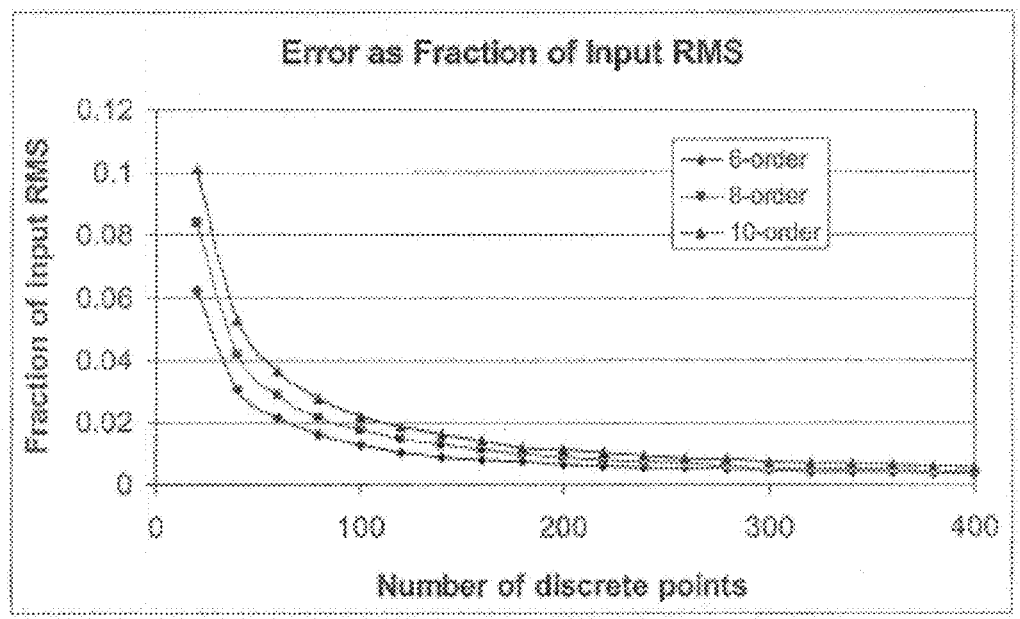
FIG. 19 shows the reconstruction error as a fraction of the root mean square (RMS) of the input Zernike coefficients for the $6^{th}$, $8^{th}$ and $10^{th}$ Zernike orders, respectively, with 100 random samples for each order for each discrete-point configuration.

The second example started with generation of normally distributed random numbers with zero mean and standard deviation of 1/n where n is the radial order of Zernike polynomials. The Fourier transforms of the wave-fronts were calculated with Eq. (53) and the estimated Zernike coefficients were calculated with Eq. (61). FIG. 19 shows the reconstruction error as a fraction of the root mean square (RMS) of the input Zernike coefficients for the $6^{th}$, $8^{th}$ and $10^{th}$ Zernike orders, respectively, with 100 random samples for each order for each discrete-point configuration. FIG. 19 indicates that the reconstruction error decreases with increasing number of discrete points and decreasing Zernike orders. As a special case, Table 3 shows an example of the input and calculated output $6^{th}$ order Zernike coefficients using 2000 discrete points in the reconstruction with Fourier transform. In this particular case, 99.9% of the wavefront was reconstructed.

TABLE 3

| Term | n | m | Zernike | Fourier |
|------|---|----|---------|---------|
| z1 | 1 | −1 | −0.69825 | −0.69805 |
| z2 | 1 | 1 | 0.3958 | 0.39554 |
| z3 | 2 | −2 | −0.12163 | −0.12168 |
| z4 | 2 | 0 | 0.36001 | 0.35978 |
| z5 | 2 | 2 | 0.35366 | 0.35345 |
| z6 | 3 | −3 | 0.062375 | 0.062296 |
| z7 | 3 | −1 | −0.0023 | −0.00201 |
| z8 | 3 | 1 | 0.26651 | 0.26616 |
| z9 | 3 | 3 | 0.21442 | 0.21411 |
| z10 | 4 | −4 | 0.072455 | 0.072314 |
| z11 | 4 | −2 | 0.15899 | 0.15892 |
| z12 | 4 | 0 | 0.080114 | 0.079814 |
| z13 | 4 | 2 | −0.07902 | −0.07928 |
| z14 | 4 | 4 | −0.10514 | −0.10511 |
| z15 | 5 | −5 | −0.06352 | −0.06343 |
| z16 | 5 | −3 | 0.013632 | 0.013534 |
| z17 | 5 | −1 | 0.090845 | 0.091203 |
| z18 | 5 | 1 | −0.07628 | −0.07672 |
| z19 | 5 | 3 | 0.1354 | 0.13502 |
| z20 | 5 | 5 | 0.027229 | 0.027169 |
| z21 | 6 | −6 | −0.0432 | −0.04315 |
| z22 | 6 | −4 | 0.06758 | 0.067413 |
| z23 | 6 | −2 | 0.015524 | 0.015445 |
| z24 | 6 | 0 | −0.01837 | −0.01873 |
| z25 | 6 | 2 | 0.064856 | 0.064546 |
| z26 | 6 | 4 | 0.040437 | 0.040467 |
| z27 | 6 | 6 | 0.098274 | 0.098141 |

Figure 20:
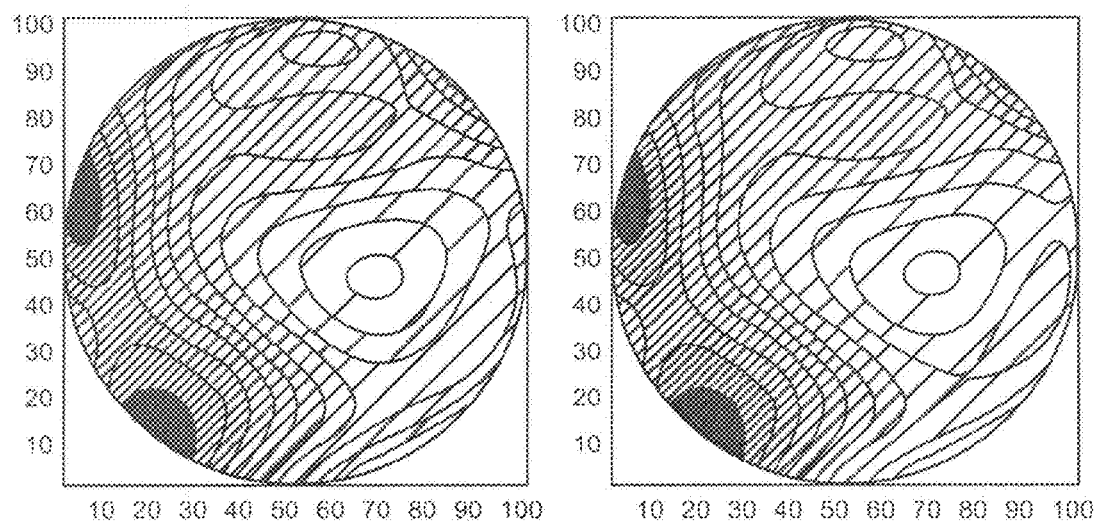
FIG. 20 illustrates a comparison between an input wavefront contour map and the calculated or wave-front Zernike coefficients from a random wavefront sample according to one embodiment of the present invention.

In a third example, random wavefronts with 100 discrete points were generated the same way as the second example, and the x- and y-derivatives of the wavefront were calculated. The Fourier coefficients were calculated with an iterative Fourier transform as described in previously incorporated U.S. patent application Ser. No. 10/872,107, and the Zernike coefficients were calculated with Eq. (61). FIG. 20 shows the comparison between the input wave-front contour map (left panel; before) and the calculated or wavefront Zernike coefficients from one of the random wave-front samples (right panel; after reconstruction). For this particular case, the input wave-front has RMS of 1.2195 µm, and the reconstructed wavefront has RMS of 1.1798 µm, hence, 97% of RMS (wavefront) was reconstructed, which can be manifested from FIG. 20. FIG. 21 shows the same Zernike coefficients from Table 3, in a comparison of the Zernike coefficients from Zernike and Fourier reconstruction.

B. Speed Consideration

Improved speed can be a reason for using the Fourier approach. This can be seen by comparing calculation times from a Zernike decomposition and from a Fourier transform. FIG. 22 shows the speed comparison between Zernike reconstruction using singular value decomposition (SVD) algorithm and Zernike coefficients calculated with Eq. (61), which also includes the iterative Fourier reconstruction with 10 iterations.

Whether it is for different orders of Zernike polynomials or for different number of discrete points, the Fourier approach can be 50 times faster than the Zernike approach. In some cases, i.e., larger number of discrete points, the Fourier approach can be more than 100 times faster, as FFT algorithm is an NlnN process, whereas SVD is an $N^2$ process.

C. Choice of dk

Figure 23:
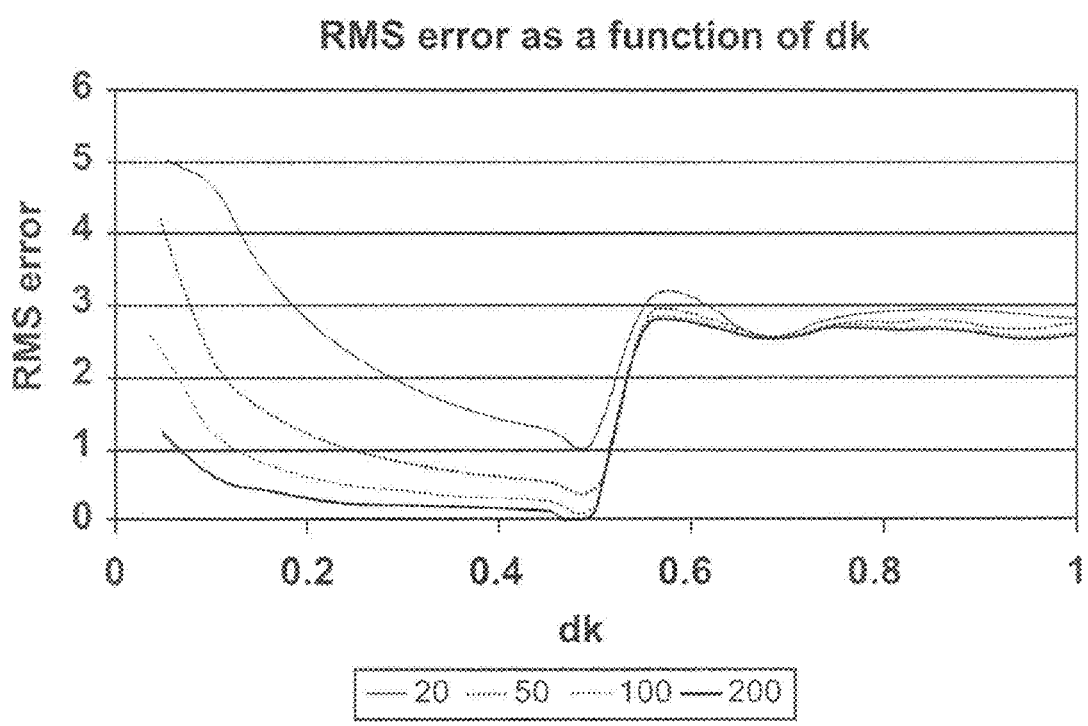
FIG. 23 illustrates an RMS reconstruction error as a function of dk according to one embodiment of the present invention.

One thing to consider when using Eq. (49) is the choice of dk when the discrete points are used to replace the infinite space. dk can represent the distance between two neighboring discrete points. If there are N discrete points, the integration from 0 to infinity (k value) will be replaced in the discrete case from 0 to Ndk. In some cases, dk represents a y-axis separation distance between each neighboring grid point of a set of N×N discrete grid points. Similarly, dk can represent an x-axis separation distance between each neighboring grid point of a set of N×N discrete grid points. FIG. 23 shows the RMS reconstruction error as a function of dk, which runs from 0 to 1, as well as the number of discrete points. As shown here, using an N×N grid, a dk value of about 0.5 provides a low RMS error. The k value ranges from 0 to N/2.

Figure 24:
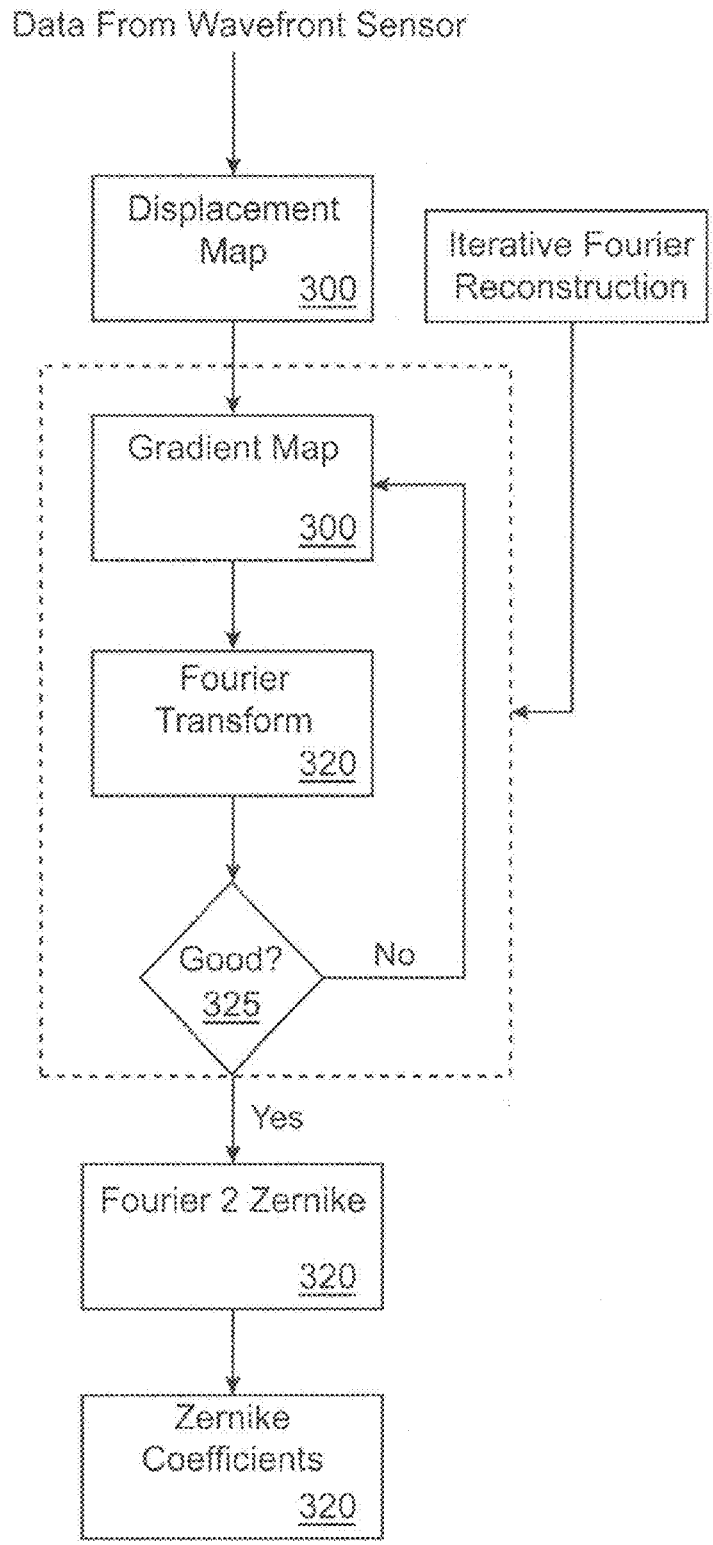
FIG. 24 illustrates an exemplary Fourier to Zernike Process for wavefront reconstruction using an iterative Fourier approach according to one embodiment of the present invention.

FIG. 24 illustrates an exemplary Fourier to Zernike Process for wavefront reconstruction using an iterative Fourier approach. A displacement map 300 is obtained from a wavefront measurement device, and a gradient map 310 is calculated. In some cases, this may involve creating a Hartmann-Shack map based on raw wavefront data. After a Fourier transform of wavefront 320 is calculated, it is checked in step 325 to determine if the result is good enough. This test can be based on convergence methods as previously discussed. If the result is not good enough, another iteration is performed. If the result is good enough, it is processed in step 330 and finally Zernike coefficient 340 is obtained.

Step 330 of FIG. 24 can be further illustrated with reference to FIG. 25, which depicts an exemplary Fourier to Zernike subprocess. For any unknown 2D surface 400, a Fourier transform 410 can be calculated (Eq. Z18). In some cases, surface 400 can be in a discrete format, represented by an N×N grid (Eq. 53). In other cases, surface may be in a nondiscrete, theoretical format (Eq. 91). Relatedly, Fourier transform 410 can be either numerical or analytical, depending on the 2D surface (Eq. 53). In an analytical embodiment, Fourier transform 410 can be represented by a grid having $N^2$ pixel points (Eq. 53). To calculate the estimated Zernike coefficients 450 that fit the unknown 2D surface, for the ith term, Zernike surface 420 can be calculated using Eq. (49), and the corresponding conjugate Fourier transform 430 can be calculated using Eq. (49A). Conjugate Fourier transform 430 can be represented by a N×N grid having $N^2$ pixel points (Eq. Z7A).

Advantageously, Zernike surface 420 is often fixed (Eq. Z3). For each $i^{th}$ Zernike term, the conjugate Fourier transform 430 can be precalculated or preloaded. In this sense, conjugate Fourier transform is usually independent of unknown 2D surface 400. The ith Zernike term can be the 1st term, the 2nd term, the 5th term, or any Zernike term. Using the results of steps 410 and 430 in a discrete format, a pixel by pixel product 440 can be calculated (Eq. 20), and the sum of all pixel values (Eq. 20), which should be a real number, can provide an estimated final ith Zernike coefficient 450. In some cases, the estimated $i^{th}$ Zernike term will reflect a Sphere term, a Cylinder term, or a high order aberration such as coma or spherical aberrations, although the present invention contemplates the use of any subjective or objective lower order aberration or high order aberration term. In some cases, these can be calculated directly from the Fourier transform during the last step of the iterative Fourier reconstruction.

Figure 25:
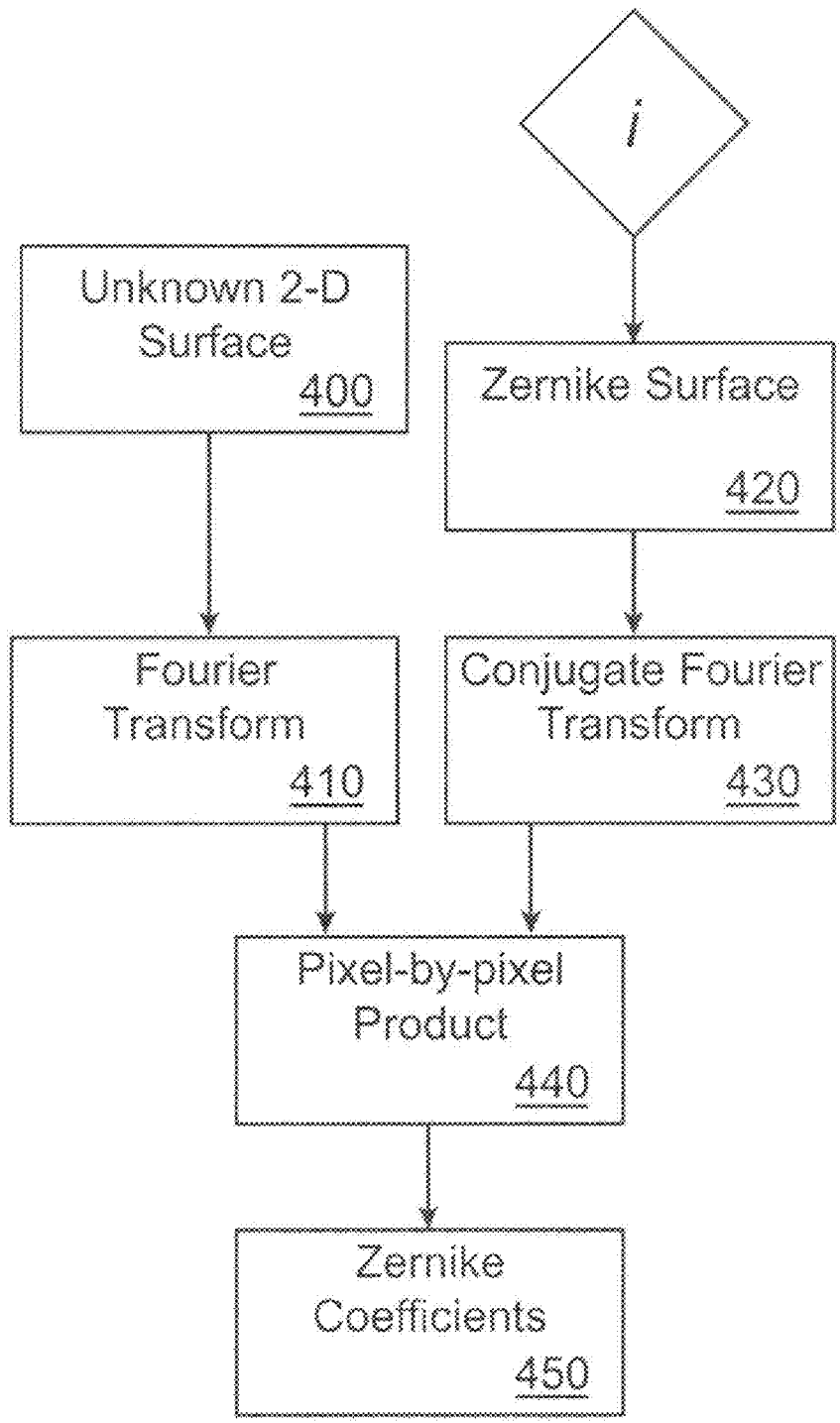
FIG. 25 illustrates an exemplary Fourier to Zernike sub-process according to one embodiment of the present invention.

It is appreciated that although the process disclosed in FIG. 25 is shown as a Fourier to Zernike method, the present invention also provides a more general approach that can use basis function surfaces other than Zernike polynomial surfaces. Moreover, these Fourier to basis function coefficient techniques can be applied in virtually any scientific field, and are in no way limited to the laser vision treatments discussed herein. For example, the present invention contemplates the conversion of Fourier transform to Zernike coefficients in the scientific fields of mathematics, physics, astronomy, biology, and the like. In addition to the laser ablation techniques described here, the conversions of the present invention can be broadly applied to the field of general optics and areas such as adaptive optics.

With continuing reference to FIG. 25, the present invention provides a method of calculating an estimated basis function coefficient 450 for a two-dimensional surface 400. As noted above, basis function coefficient 450 can be, for example, a wide variety of orthogonal and non-orthogonal basis functions. As noted previously, the present invention is well suited for the calculation of coefficients from orthogonal and non-orthogonal basis function sets alike. Examples of complete and orthogonal basis function sets include, but are not limited to, Zernike polynomials, Fourier series, Chebyshev polynomials, Hermite polynomials, Generalized Laguerre polynomials, and Legendre polynomials. Examples of complete and non-orthogonal basis function sets include, but are not limited to, Taylor monomials, and Seidel and higher-order power series. The conversion can include calculating Zernike coefficients from Fourier coefficients and then converting the Zernike coefficients to the coefficients of the non-orthogonal basis functions, based on estimated basis function coefficient 450. In an exemplary embodiment, the present invention provides for conversions of expansion coefficients between various sets of basis functions, including the conversion of coefficients between Zernike polynomials and Fourier series.

The two dimensional surface 400 is often represented by a set of N×N discrete grid points. The method can include inputting a Fourier transform 410 of the two dimensional surface 400. The method can also include inputting a conjugate Fourier transform 430 of a basis function surface 420. In some cases, Fourier transform 410 and conjugate Fourier transform 430 are in a numerical format. In other cases, Fourier transform 410 and conjugate Fourier transform 430 are in an analytical format, and in such instances, a y-axis separation distance between each neighboring grid point can be 0.5, and an x-axis separation distance between each neighboring grid point can be 0.5. In the case of Zernike polynomials, exemplary equations include equations (49) and (49A).

Figure 26:
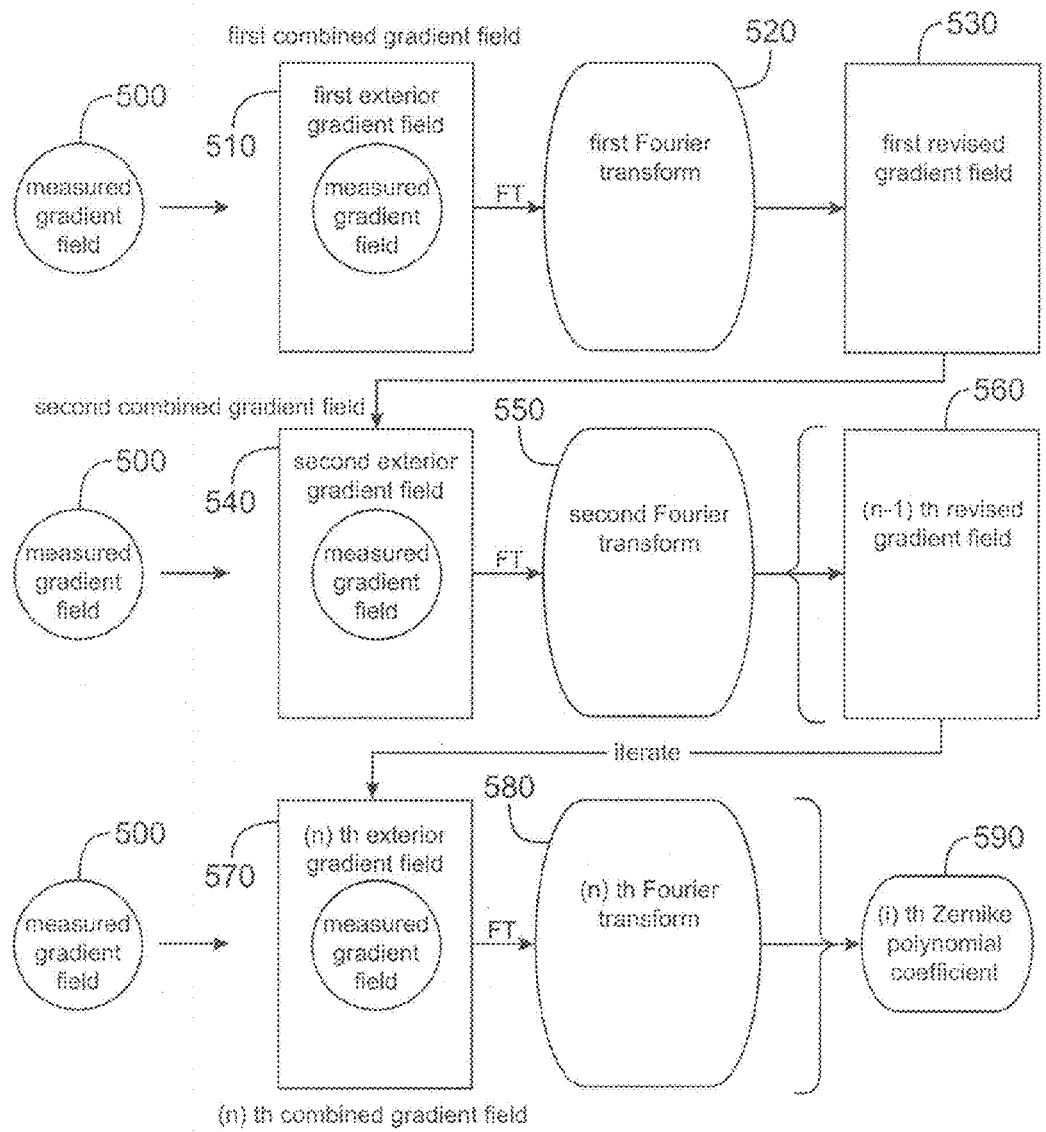
FIG. 26 illustrates an exemplary iterative approach for determining an $i^{th}$ Zernike polynomial according to one embodiment of the present invention.

An exemplary iterative approach for determining an $i^{th}$ Zernike polynomial is illustrated in FIG. 26. The approach begins with inputting optical data from the optical tissue system of an eye. Often, the optical data will be wavefront data generated by a wavefront measurement device, and will be input as a measured gradient field 500, where the measured gradient field corresponds to a set of local gradients within an aperture. The iterative Fourier transform will then be applied to the optical data to determine the optical surface model. This approach establishes a first combined gradient field 210, which includes the measured gradient field 500 disposed interior to a first exterior gradient field. The first exterior gradient field can correspond to a plane wave, or an unbounded function, that has a constant value W(x,y) across the plane and can be used in conjunction with any aperture.

In some cases, the measured gradient field 500 may contain missing, erroneous, or otherwise insufficient data. In these cases, it is possible to disregard such data points, and only use those values of the measured gradient field 500 that are believed to be good when establishing the combined gradient field 510. The points in the measured gradient field 500 that are to be disregarded are assigned values corresponding to the first exterior gradient field. By applying a Fourier transform, the first combined gradient field 510 is used to derive a first Fourier transform 520, which is then used to provide a first revised gradient field 530.

A second combined gradient field 540 is established, which includes the measured gradient field 200 disposed interior to the first revised gradient field 530. Essentially, the second exterior gradient field is that portion of the first revised gradient field 530 that is not replaced with the measured gradient field 500. In a manner similar to that described above, it is possible to use only those values of the measured gradient field 500 that are believed to be valid when establishing the second combined gradient field 540. By applying a Fourier transform, the second combined gradient field 540 is used to derived a second Fourier transform 550. The second Fourier transform 550, or at least a portion thereof, can be used to provide the $i^{th}$ Zernike polynomial 590. The optical surface model can then be determined based on the $i^{th}$ Zernike polynomial 590.

Optionally, the second combined gradient field can be further iterated. For example, the second Fourier transform 550 can be used to provide an $(n-1)^{th}$ gradient field 560. Then, an $(n)^{th}$ combined gradient field 570 can be established, which includes the measured gradient field 500 disposed interior to the $(n-1)^{th}$ revised gradient field 560. Essentially, the $(n)^{th}$ exterior gradient field is that portion of the $(n-1)^{th}$ revised gradient field 260 that is not replaced with the measured gradient field 500. By applying a Fourier transform, the $(n)^{th}$ combined gradient field 570 is used to derived an $(n)^{th}$ reconstructed wavefront 580. The $(n)^{th}$ reconstructed wavefront 580, or at least a portion thereof, can be used to provide an $i^{th}$ Zernike polynomial 590. The optical surface model can then be determined based on the $i^{th}$ Zernike polynomial is 590. In practice, each iteration can bring each successive reconstructed wavefront closer to reality, particularly for the boundary or periphery of the pupil or aperture.

Arbitrary Shaped Apertures

Wavefront reconstruction over apertures of arbitrary shapes can be achieved by calculating an orthonormal set of Zernike basis over the arbitrary aperture using a Gram-Schmidt orthogonalization process. It is possible to perform iterative Fourier reconstruction of a wavefront, and convert the Fourier coefficients to and from the coefficients of the arbitrary orthonormal basis set. Such techniques can be applied to apertures having any of a variety of shapes, including, for example, elliptical, annular, hexagonal, irregular, and non-circular shapes.

Wavefront reconstruction from wavefront derivative data has been discussed in length in the literature. Modal reconstruction for circular apertures using Zernike circle polynomials with a singular value decomposition (SVD) algorithm is described in G.-m. Dai, *J. Opt. Soc. Am. A* 13, 1218-1225 (1996). For other type of apertures, such as elliptical, annular, hexagonal, or non-circular apertures, such approaches may not be optimal because Zernike circle polynomials are not orthogonal over elliptical, hexagonal, annular, or non-circular apertures. A Gram-Schmidt orthogonalization (GSO) process can be used to analytically or numerically calculate the orthonormal basis functions over a particular aperture (e.g. modified Zernike polynomials), such as a hexagon. Although a complete set of analytical formulae for hex-Zernike is possible, it is often not the case for an irregular aperture. With an orthonormal set of basis functions over the desired aperture, either numerical or analytical, it is possible to reconstruct the wavefront from the derivative data using SVD algorithm. An algorithm using Fourier series was recently proposed in G.-m. Dai, *Opt. Lett.* 31, 501-503 (2006).

It has been discovered that the application domain of Fourier series, as discussed in G.-m. Dai, *Opt. Lett.* 31, 501-503 (2006), can be extended to any type of orthonormal function and any type of aperture shape. Coefficients of any basis set can be converted to and from the coefficients of the Fourier series. With Zernike circle polynomials as examples, four different types of apertures are considered: elliptical, annular, hexagonal, and irregular. Wavefront reconstruction using the Fourier series can be compared to the SVD approach, and the respective accuracy and speed of these approaches can be evaluated.

Consider a wavefront defined by a first domain S (such as a circle) in polar coordinates, denoted as $W(\rho,\theta)$. Suppose a complete and analytical set of basis function $\{Z_i(\rho,\theta)\}$ is orthonormal over domain S, it is possible to expand the wavefront into this set as $$W(\rho,\theta) = \sum_{i=1}^{\infty} c_i Z_i(\rho,\theta), \tag{101}$$

where the expansion coefficient $c_i$ can be calculated from the orthonormality as $$c_i = \iint P_S(\rho) W(\rho,\theta) Z_i(\rho,\theta) d\rho, \tag{102}$$

where $d\rho = \rho d\rho d\theta$ and $P_S(\rho)$ is the aperture function bound by domain S. The integration in Eq. (102), and in other equations in this application, can cover the whole space.

Suppose domain T is inscribed by domain S such that T∈S. If the wavefront derivative data is only known within domain T, Eq. (102) may no longer be useful because the basis set $\{Z_i(\rho,\theta)\}$ is typically not orthogonal over domain T. A set of orthonormal basis functions $\{F_i(\rho,\theta)\}$ can be calculated with GSO as described in R. Upton and B. Ellerbroek, *Opt. Lett.* 29, 2840-2842 (2004)

$$F_i(\rho,\theta) = \sum_{j=1}^{L} c_{ij} Z_j(\rho,\theta), \tag{103}$$

where L is the total number of expansion terms and $C_{ij}$ is the conversion matrix that can be calculated recursively. Therefore, the wavefront within domain T can be written as $$W(\rho,\theta) = \sum_{i=1}^{L} b_i F_i(\rho,\theta). \tag{104}$$

Once the set of $\{F(\rho,\theta)\}$ is calculated, multiplying $P_T(\rho) F_i(\rho,\theta)$ on both sides of Eq. (104) and applying the orthonormality of basis set $\{F_i(\rho,\theta)\}$, we obtain the expansion coefficients over domain T as $$b_i = \iint P_T(\rho) W(\rho,\theta) F_i(\rho,\theta) d\rho, \tag{105}$$

where $P_T(\rho)$ is the aperture function bound by domain T.

When $F_i(\rho,\theta)$ can not be calculated analytically, a numerical method can be used to replace Eq. (105) as $$b_i = \frac{1}{N} \sum_{n=1}^{N} P_T(\rho_n, \theta_n) W(\rho_n, \theta_n) F_i(\rho_n, \theta_n), \quad (106)$$

where N is the total number of data points within domain T.

Substituting Eq. (104) into Eq. (102) and restricting to domain T only, we have $$c_i = \int P_S(\rho) \sum_{j=1}^{L} b_j F_j(\rho, \theta) Z_i(\rho, \theta) d\rho \quad (107)$$

$$= \sum_{j=1}^{L} b_j \int\int P_S(\rho) F_j(\rho, \theta) Z_i(\rho, \theta) d\rho$$

$$= \sum_{j=1}^{L} b_j \int\int P_T(\rho) F_j(\rho, \theta) Z_i(\rho, \theta) d\rho.$$

In deriving Eq. (107), we have used the observation that T∈S and $\{F_i(\rho,\theta)\}$ is often only supported in domain T. It is worth noting that the equal sign can be an approximation in a least squares sense. Equation (107) can also be written as numerical summation as $$c_i = \frac{1}{N} \sum_{j=1}^{L} b_j \sum_{n=1}^{N} P_T(\rho_n, \theta_n) F_j(\rho_n, \theta_n) Z_i(\rho_n, \theta_n). \quad (108)$$

Equations (107) and (108) are exemplary formulae for converting the $\{b_i\}$ coefficients to $\{c_i\}$ coefficients.

It is possible to obtain wavefront derivative data over domain T by means of an aberrometer or interferometer. Derivative data can be used to reconstruct the wavefront and to estimate classical aberrations contained in the wavefront. Because of the connection to classical aberrations, Zernike polynomials have been widely used as wavefront expansion basis functions. See M. Born and E. Wolf, *Principles of optics*, 5$^{th}$ ed. Sec. 9.2 (Pergamon, New York, 1965). Zernike polynomials can be used to replace basis set $\{Z_i(\rho,\theta)\}$ as an example. One way to reconstruct wavefront from the derivative data is to use the SVD algorithm over data set within domain T, as demonstrated in G.-m. Dai, *J. Opt. Soc. Am. A* 13, 1218-1225 (1996).

According to ANSI Z80.28-2004, *Methods for Reporting Optical Aberrations of Eyes*, American National Standards Institute (2004), Zernike circle polynomials can be defined as $$Z_n^m(\rho, \theta) = \begin{cases} N_n^m R_n^{|m|}(\rho) \cos(m\theta) & (m \geq 0) \\ N_n^m R_n^{|m|}(\rho) \sin(|m|\theta) & (m < 0), \end{cases} \quad (109)$$

where n and m denote the radial degree and the azimuthal frequency, respectively. According to M. Born and E. Wolf, *Principles of optics*, 5$^{th}$ ed. Sec. 9.2 (Pergamon, New York, 1965), radial polynomials can be defined as $$R_n^{|m|}(\rho) = \sum_{s=0}^{(n-|m|)/2} \frac{(-1)^s (n-s)! \rho^{n-2s}}{s![(n+m)/2-s]![(n-m)/2-s]!}, \quad (110)$$

and the normalization factor as $$N_n^m = \sqrt{(2-\delta_{m0})(n+1)}, \quad (111)$$

where $\delta_{m0}$ is the Kronecker symbol.

Reconstruction of wavefront from derivative data using iterative Fourier transform has been previously described. It is possible to define domain P as the rectangle area inscribing domain T, or T∈P. Sinusoidal functions (Fourier series) can be used as the basis functions. The wavefront expansion can be written as $$W(\rho,\theta) = \iint a(k,\phi) \exp(j2\pi k \cdot \rho) dk, \quad (112)$$

where $a(k,\phi)$ is the matrix of coefficient, or the Fourier coefficients (Fourier spectrum). Using the properties of Fourier transform, Eq. (112) can be written as $$a(k,\phi) = \iint W(\rho,\theta) \exp(-j2\pi k \cdot \rho) dk. \quad (113)$$

Substituting Eq. (112) into (105), we get $$b_i = \iint a(k,\phi) V_i^*(k,\theta) dk, \quad (114)$$

where * stands for the complex conjugate and the Fourier transform of basis function $\{F_i(\rho,\theta)\}$ $$V(k,\phi) = \iint P_T(\rho) F_i(\rho\theta) \exp(j2\pi k \cdot \rho) d\rho. \quad (115)$$

can be calculated either analytically or numerically. Substituting Eq. (104) into Eq. (113), we obtain the conversion of coefficients $\{b_i\}$ into Fourier coefficients as $$a(k, \phi) = \sum_{i=1}^{L} b_i U_i(k, \phi). \quad (116)$$

In some embodiments, coefficients of function $Z_i(\rho,\theta)$ can be calculated from the Fourier spectrum of the wavefront based on Fourier transform of Zernike circular polynomials.

To demonstrate the effectiveness of the above technique, common apertures of elliptical, annular, and hexagonal shapes, and an irregular shape were used.

A random wavefront was generated with the first four orders of Zernike circle polynomials. Wavefront derivative data was calculated within these four different apertures. Both the SVD technique (with reconstruction of the first four orders) and the Fourier technique were used to reconstruct the wavefronts. With the Fourier technique, coefficients of basis set $\{F_i(\rho,\theta)\}$ (for the first four orders) were calculated using Eq. (114), and 20 iterations were used for each case. The ratio of the short to the long axis of the elliptical aperture is 0.85, and the obscuration ratio of the annular aperture is 0.35. In some embodiments, coefficients of Zernike circular polynomials can be calculated using Eq. (108).

Figure 27:
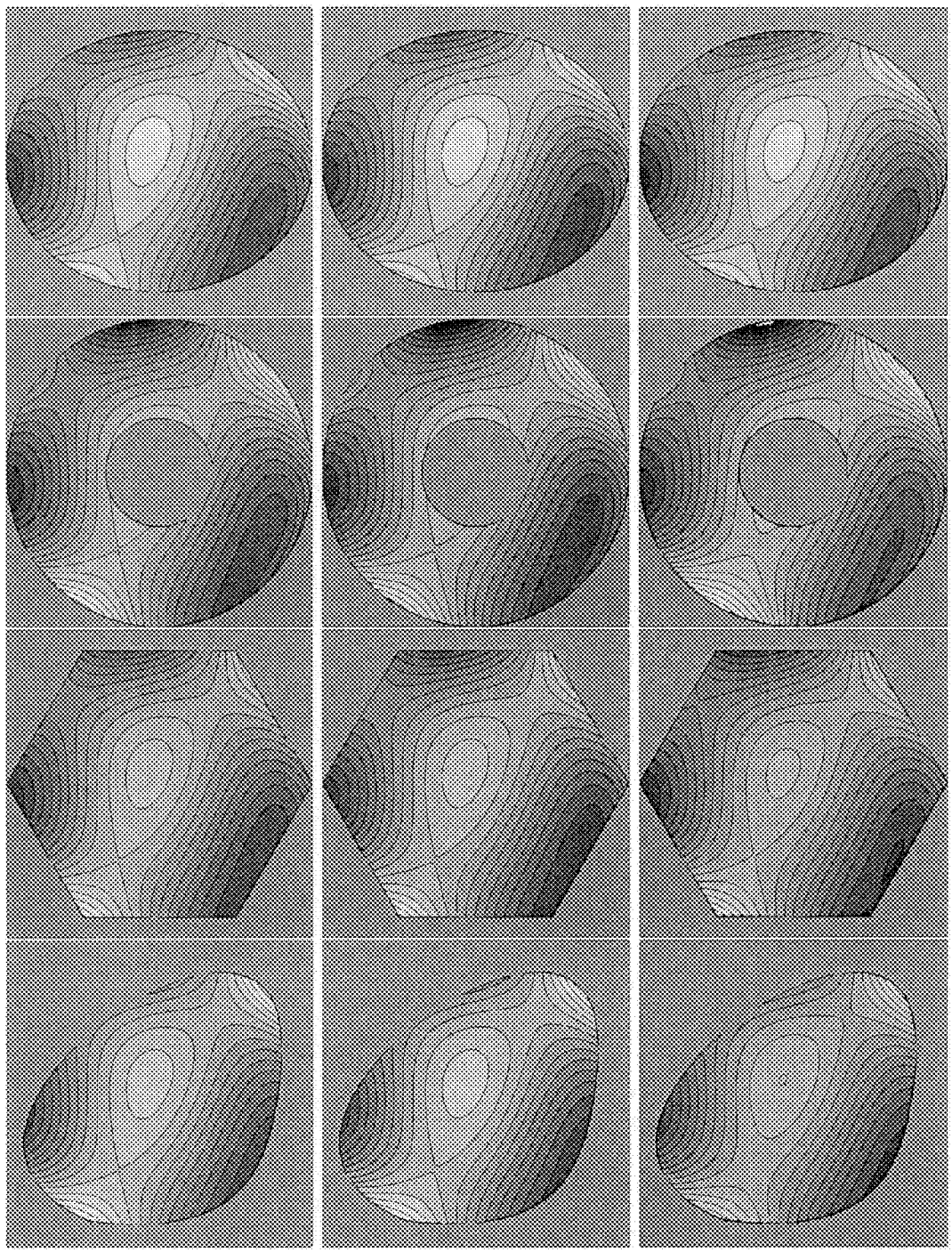
FIG. 27 depicts wavefront reconstruction data according to one embodiment of the present invention.

FIG. 27 depicts the input, SVD reconstructed, and the Fourier reconstructed wavefronts for elliptical, annular, hexagonal, and irregular apertures. The illustration provides contour plots for the input (first column), SVD reconstructed (middle column), and Fourier reconstructed (last column) wavefronts. Four Zernike orders were used for the input wavefront. The contour scales for all plots are identical. The corresponding input and calculated coefficients $\{b_i\}$ are shown in Table 4. The reconstructed coefficients $\{b_i\}$ are compared to the input coefficients. The four Zernike orders were used in the input wavefront. N=401×401. SVD reconstructed wavefronts show very good agreement with the input wavefronts and so do the coefficients. Fourier technique also show effectiveness, but with inferior results. The number of terms in the reconstruction is often always smaller than the number of terms in the input wavefront, because when the wavefront is unknown the number of terms is often unknown.

TABLE 4

| Zernike Term | Elliptical | | | Annular | | | Hexagonal | | | Irregular | | |
|---|---|---|---|---|---|---|---|---|---|---|---|---|
| | Input | SVD | Fourier | Input | SVD | Fourier | Input | SVD | Fourier | Input | SVD | Fourier |
| 1 | 0.104 | 0.104 | 0.060 | 0.037 | 0.037 | −0.018 | 0.061 | 0.060 | 0.046 | 0.133 | 0.133 | 0.019 |
| 2 | −0.055 | −0.055 | −0.100 | −0.055 | −0.055 | −0.005 | −0.101 | −0.100 | −0.095 | −0.156 | −0.155 | −0.045 |
| 3 | 0.296 | 0.296 | 0.339 | 0.403 | 0.402 | 0.457 | 0.340 | 0.339 | 0.368 | 0.211 | 0.210 | 0.163 |
| 4 | −0.336 | −0.336 | −0.312 | −0.171 | −0.171 | −0.170 | −0.313 | −0.312 | −0.310 | −0.309 | −0.309 | −0.232 |
| 5 | −0.144 | −0.144 | −0.193 | −0.134 | −0.133 | −0.130 | −0.194 | −0.193 | −0.190 | −0.249 | −0.248 | −0.161 |
| 6 | 0.170 | 0.169 | 0.156 | 0.249 | 0.248 | 0.252 | 0.157 | 0.156 | 0.156 | 0.104 | 0.103 | 0.184 |
| 7 | −0.044 | −0.044 | −0.053 | −0.068 | −0.068 | −0.064 | −0.053 | −0.053 | −0.053 | −0.046 | −0.046 | −0.051 |
| 8 | 0.145 | 0.145 | 0.095 | 0.122 | 0.121 | 0.117 | 0.095 | 0.095 | 0.099 | 0.099 | 0.099 | 0.022 |
| 9 | 0.097 | 0.097 | 0.110 | 0.137 | 0.136 | 0.144 | 0.110 | 0.110 | 0.115 | 0.046 | 0.046 | 0.106 |
| 10 | −0.091 | −0.091 | −0.083 | −0.130 | −0.130 | −0.150 | −0.083 | −0.083 | −0.092 | −0.014 | −0.014 | −0.032 |
| 11 | −0.004 | −0.004 | −0.004 | −0.006 | −0.006 | −0.021 | −0.004 | −0.004 | −0.013 | 0.143 | 0.143 | 0.082 |
| 12 | 0.166 | 0.165 | 0.129 | 0.130 | 0.129 | 0.123 | 0.129 | 0.129 | 0.131 | 0.050 | 0.050 | 0.069 |
| 13 | 0.019 | 0.019 | 0.040 | 0.115 | 0.115 | 0.109 | 0.040 | 0.040 | 0.038 | 0.044 | 0.044 | 0.026 |
| 14 | −0.140 | −0.140 | −0.137 | −0.221 | −0.220 | −0.212 | −0.137 | −0.137 | −0.132 | −0.073 | −0.072 | −0.062 |
| RMS | — | 0.001 | 0.117 | — | 0.002 | 0.096 | — | 0.001 | 0.036 | — | 0.001 | 0.250 |

Figure 28:
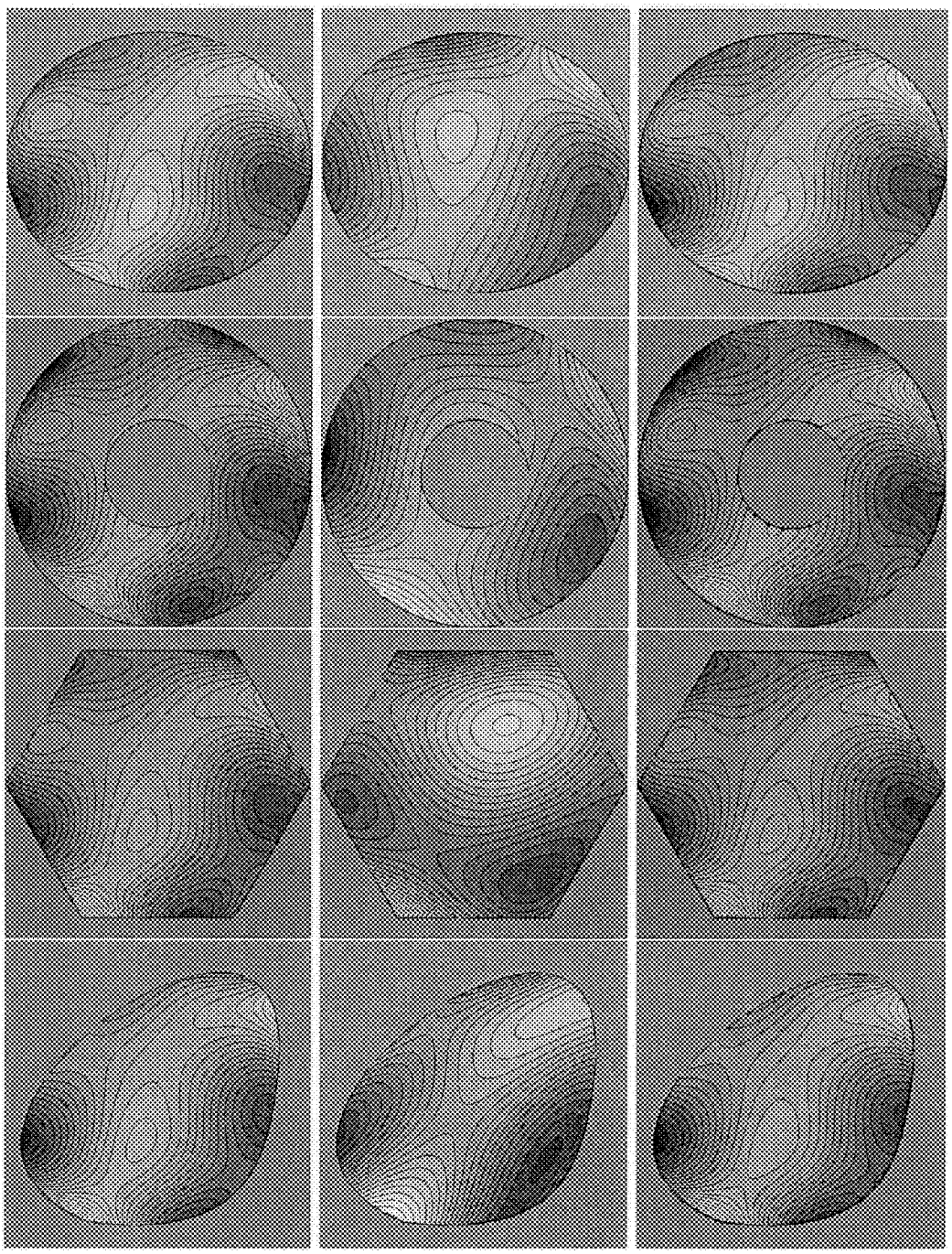
FIG. 28 depicts wavefront reconstruction data according to one embodiment of the present invention.

When the number of terms in the input wavefront was increased from four orders to six orders, the Fourier technique became superior to SVD technique as it used the information from the discrete data optimally. FIG. 28 shows the input and reconstructed wavefronts for these four different apertures. This illustration provides contour plots for the input (first column), SVD reconstructed (middle column), and Fourier reconstructed (last column) wavefronts. Six Zernike orders were used for the input wavefront. The contour scales for all plots are identical. The corresponding coefficients are shown in Table 5. In this embodiment, it is quite clear that the Fourier technique works better than the SVD technique. The reconstructed coefficients $\{b_i\}$ are compared to the input coefficients. Six Zernike orders were used in the input wavefront. N=401×401. Table 6 shows a comparison of the reconstruction time (in seconds) for the two techniques for different sampling sizes. In this embodiment, the Fourier technique is in general faster than the SVD technique.

Wavefront reconstruction with Fourier series can be extended to any set of orthonormal basis functions, whether they are analytical or numerical, and to any shapes of apertures. In exemplary embodiments, the Fourier technique is more effective and faster than the SVD technique.

Orthonormal Polynomials for Hexagonal Pupils

Orthonormal polynomials for hexagonal pupils can be determined by the Gram-Schmidt orthogonalization of Zernike circle polynomials. Closed-form expressions for the hexagonal polynomials are provided. It is possible to obtain orthonormal polynomials for hexagonal pupils by the Gram-Schmidt orthogonalization of Zernike circle polynomials. The polynomials thus obtained can depend on the sequence of the Zernike polynomials used in the orthogonalization process. See G. A. Korn and T. M. Korn, *Mathematical Handbook for Scientists and Engineers* (McGraw-Hill, New York, 1968. Others have proposed a matrix that converts Zernike

TABLE 5

| Zernike Term | Elliptical | | | Annular | | | Hexagonal | | | Irregular | | |
|---|---|---|---|---|---|---|---|---|---|---|---|---|
| | Input | SVD | Fourier | Input | SVD | Fourier | Input | SVD | Fourier | Input | SVD | Fourier |
| 1 | 0.141 | 0.134 | 0.138 | 0.037 | −0.173 | −0.010 | 0.061 | 0.469 | 0.012 | 0.133 | 0.222 | 0.003 |
| 2 | −0.053 | −0.046 | −0.019 | −0.055 | −0.020 | 0.002 | −0.101 | 0.140 | −0.136 | −0.156 | −0.137 | −0.009 |
| 3 | 0.290 | 0.288 | 0.315 | 0.403 | 0.439 | 0.448 | 0.340 | 0.342 | 0.349 | 0.211 | 0.479 | 0.177 |
| 4 | −0.330 | −0.329 | −0.328 | −0.171 | −0.170 | −0.174 | −0.313 | −0.315 | −0.312 | −0.309 | −0.336 | −0.234 |
| 5 | −0.125 | −0.123 | −0.119 | −0.134 | −0.227 | −0.127 | −0.194 | −0.243 | −0.159 | −0.249 | −0.299 | −0.237 |
| 6 | 0.290 | 0.207 | 0.287 | 0.249 | 0.151 | 0.236 | 0.157 | 0.180 | 0.215 | 0.104 | 0.118 | 0.298 |
| 7 | 0.010 | −0.070 | 0.009 | −0.068 | −0.085 | −0.076 | −0.053 | −0.442 | −0.057 | −0.046 | −0.200 | −0.064 |
| 8 | 0.141 | 0.185 | 0.142 | 0.122 | 0.128 | 0.118 | 0.095 | −0.127 | 0.050 | 0.099 | 0.108 | −0.020 |
| 9 | −0.012 | 0.057 | −0.010 | 0.137 | 0.269 | 0.134 | 0.110 | 0.142 | 0.067 | 0.046 | 0.113 | 0.119 |
| 10 | −0.179 | −0.067 | −0.177 | −0.130 | 0.040 | −0.124 | −0.083 | −0.090 | −0.175 | −0.014 | −0.079 | −0.046 |
| 11 | 0.018 | 0.050 | 0.001 | −0.006 | 0.010 | −0.023 | −0.004 | −0.051 | −0.071 | 0.143 | 0.002 | 0.063 |
| 12 | 0.159 | 0.113 | 0.154 | 0.130 | 0.132 | 0.122 | 0.129 | 0.123 | 0.129 | 0.050 | 0.056 | 0.057 |
| 13 | 0.076 | 0.025 | 0.078 | 0.115 | 0.060 | 0.109 | 0.040 | 0.017 | 0.104 | 0.044 | 0.136 | 0.081 |
| 14 | −0.221 | −0.171 | −0.209 | −0.221 | −0.119 | −0.210 | −0.137 | −0.161 | −0.208 | −0.073 | −0.273 | −0.057 |
| RMS | — | 0.202 | 0.048 | — | 0.357 | 0.095 | — | 0.676 | 0.044 | — | 0.348 | 0.371 |

TABLE 6

| N | SVD | Fourier |
|---|---|---|
| 100 | 0.016 | 0.000 |
| 400 | 0.031 | 0.002 |
| 1600 | 0.063 | 0.016 |
| 10000 | 0.453 | 0.141 |
| 40000 | 1.781 | 0.609 |
| 160000 | 7.266 | 2.531 | circle polynomials into hexagonal polynomials, however the matrix contains numerical errors which are apparently due to the finite number of points used in carrying out the integrations that arise in the orthogonalization process. However, it has been discovered that these integrations can be carried out analytically in a closed form.

It is quite common in optical design and testing to use Zernike circle polynomials to describe the aberrations of a system. These polynomials have the advantage that they represent balanced aberrations. Because of their orthogonality across a circular pupil, the Zernike expansion coefficients are independent of each other, each coefficient represents the standard deviation of the corresponding Zernike term (with the exception of the piston term), and the variance of the aberration is equal to the sum of the squares of the coefficients. However, in the case of a large segmented minor, the segments are typically hexagonal in shape, as in the Keck telescope. Although the aberration function of a hexagonal segment can be expanded in terms of Zernike circle polynomials, the advantages of orthogonality of the polynomials can be lost because Zernike polynomials are not orthogonal over a hexagonal region. Here, polynomials are developed that are orthonormal over a hexagonal segment by the Gram-Schmidt orthogonalization process. These polynomials can be compared to the circle polynomials by isometric, interferometric, and PSF plots.

Figure 29:
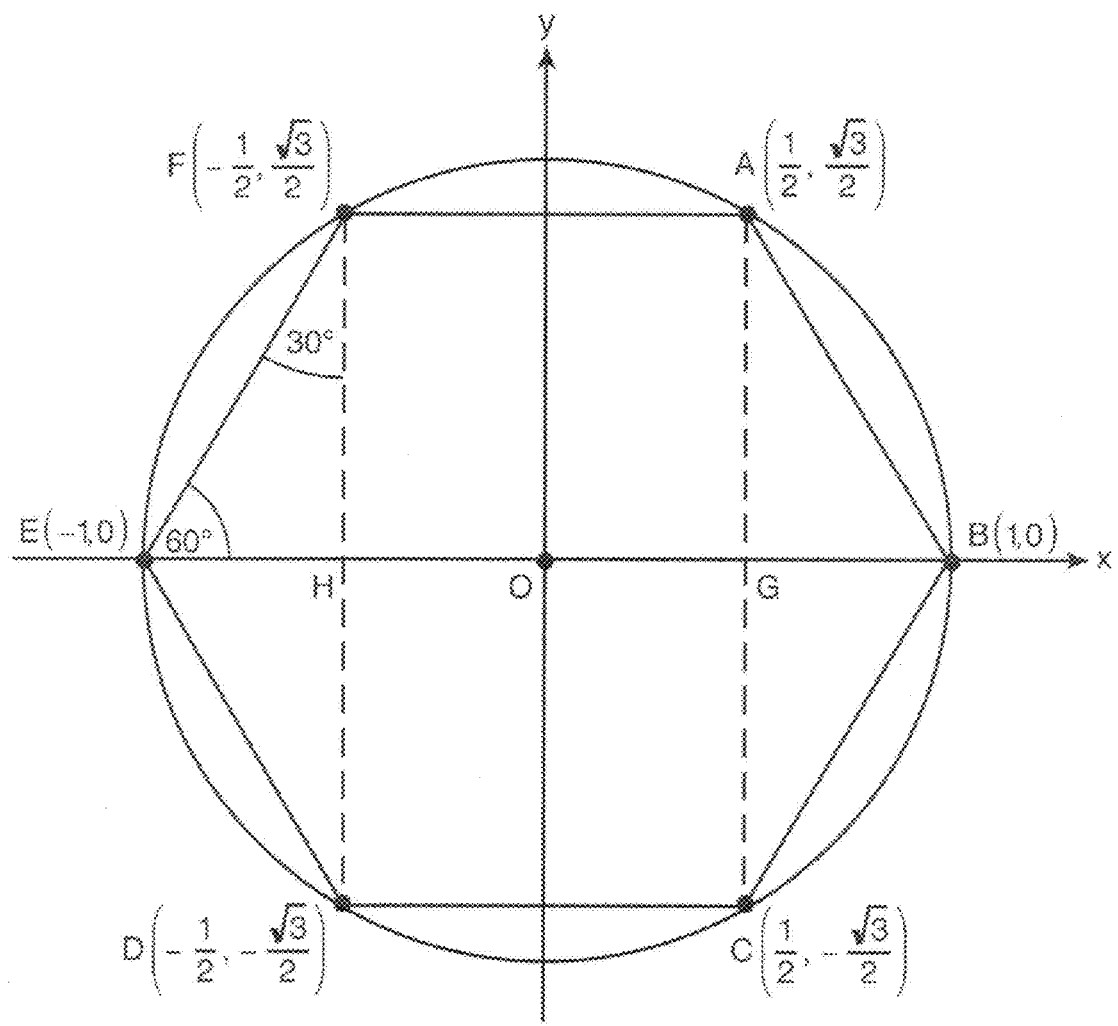
FIG. 29 shows a coordinate system for a hexagonal pupil according to one embodiment of the present invention.

In Cartesian coordinates (x,y), the aberration function for a hexagonal pupil can be expanded in terms of polynomials $H_j(x,y)$ that are orthonormal over the pupil:

$$W(x, y) = \sum_j a_j H_j(x, y), \tag{201}$$

where $a_j$ is an expansion or the aberration coefficient of the polynomial $H_i(x,y)$. The orthonormality of the polynomials is represented by $$\frac{1}{A} \int_{hexagon} H_j(x, y) H_{j'}(x, y) = dxdy = \delta_{jj'}, \tag{202}$$

where $$A \int_{hexagon} dxdy \tag{203}$$

is the area of a unit hexagon, i.e., one with each side of unity length, and the integrations are carried out over the hexagonal region of the pupil. FIG. 29 shows a coordinate system for a hexagonal pupil represented by a unit hexagon inscribed inside a unit circle. As illustrated here, where a unit hexagon is inscribed inside a unit circle, the area A is equal to the sum of the area $\sqrt{3}$ of the central rectangle ACDF and the combined area $\sqrt{3}/2$ of the two triangles ABC and DEF. Thus, $A=3\sqrt{3}/2$. The area of the unit hexagon is approximately 17.3% smaller than the area of the unit circle. The aberration coefficients and the variance are given by $$a_j = \frac{1}{A} \int_{hexagon} W(x, y) H_j(x, y) dxdy \tag{204}$$

and $$\sigma^2 = \sum_j a_j^2, j \neq 1, \tag{205}$$

respectively. The mean value of each polynomial, except for j=1, is zero. The number of polynomials, i.e., the maximum value of j is increased until the variance given by Eq. (205) is equal to the actual variance within a prechosen tolerance.

The orthonormal polynomials $H_j(x,y)$ can be obtained from the Zernike polynomials $Z_j(x,y)$ by the Gram-Schmidt orthogonalization process. Using abbreviated notation, where the argument (x,y) of the polynomials is omitted, $$G_1 = Z_1 = 1, \tag{206a}$$

$$G_{j+1} = \sum_{k=1}^{j} c_{j+1,k} H_k + Z_{j+1}, \tag{206b}$$

$$H_{j+1} = \frac{G_{j+1}}{\|G_{j+1}\|} \tag{206c}$$

$$= \frac{G_{j+1}}{\left[\frac{1}{2} \int_{hexagon} G_{j+1}^2 dxdy\right]^{1/2}},$$

where $$c_{j+1,k} = -\frac{1}{A} \int_{hexagon} Z_{j+1} H_k \, dxdy. \tag{206d}$$

Thus, the H-polynomials are obtained recursively starting with $H_1=1$. Each G- and, therefore, H-polynomial is a linear combination of the Zernike polynomials. The orthonormal H-polynomials represent the unit vectors of the space that spans the aberration function. They can be written in a matrix form according to $$H_l(x, y) = \sum_{i=1}^{l} M_{li} Z_i(x, y) \text{ with } M_{ll} = \frac{1}{\|G_l\|}. \tag{207}$$

While the diagonal elements of the M-matrix are simply equal to the normalization constants of the G-polynomials, there are no matrix elements above the diagonal. The matrix is triangular and the missing elements may be given a value of zero when multiplying a Zernike column vector ( . . . , $Z_j$, . . . ) to obtain the hexagonal column vector ( . . . , $H_j$, . . . ).

The region of integration across the hexagonal pupil consists of five parts: rectangle ACDF in which x varies from $-\frac{1}{2}$ to $\frac{1}{2}$ and y varies from $-\sqrt{3}/2$ to $\sqrt{3}/2$, triangle AGB with x varying from $1-y/\sqrt{3}$ to $\frac{1}{2}$ and y from 0 to $\sqrt{3}/2$ or with x varying from $\frac{1}{2}$ to 1 and y from $\sqrt{3}(1-x)$ to 0, triangle GCB with x varying from $1+y/\sqrt{3}$ to 1 and y from $-\sqrt{3}/2$ to 0 or x varying from $\frac{1}{2}$ to 1 and y varying from $-\sqrt{3}(1-x)$ to 0, triangle DHE with x varying from $-1-y/\sqrt{3}$ to $-\frac{1}{2}$ and y from $-\sqrt{3}/2$ to 0 or x varying from $-1$ to $-\frac{1}{2}$ and y from 0 to $-\sqrt{3}(1+x)$, triangle HFE with x varying from $-1+y/\sqrt{3}$ to $-\frac{1}{2}$ and from 0 to $\sqrt{3}/2$ or x varying from $-1$ to $-\frac{1}{2}$ and y from 0 to $\sqrt{3}(1+x)$. One or the other range of integration is convenient depending on whether the integration is carried over x first and then over y or vice versa. If the integrand is an odd function of x or y or both, then its integral is zero because of the hexagonal symmetry. If it is an even function of x and y, then the integral across the rectangle ACDF is four times its value for x varying from 0 to $\frac{1}{2}$ and y from 0 to $\sqrt{3}/2$.

The Zernike circle polynomials are orthonormal over a circular pupil of unit radius according to $$\int_{x^2+x^2 \leq 1} Z_j(x, y) Z_{j'}(x, y) dxdy \bigg/ \int_{x^2+x^2 \leq 1} dxdy = \delta_{jj'}. \tag{208}$$

Table 7 lists the first eleven Zernike circle polynomials in Cartesian coordinates, where $\rho^2=x^2+y^2$. See R. J. Noll, "Zernike polynomials and atmospheric turbulence," *J. Opt. Soc. Am.* 66, 207-211 (1976); V. N. Mahajan, *Optical Imaging and Aberrations, Part II: Wave Diffraction Optics*, SPIE Press, Bellingham, Wash. (Second Printing 2004). These polynomials are ordered such that an even j corresponds to $\cos m\theta$ term and an odd j corresponds to a $\sin m\theta$ term when written in polar coordinates (r, $\theta$). Substituting for the Zernike polynomials into Eqs. (206) and noting that the integral of an odd function over the hexagon is zero owing to its symmetry, it is possible to obtain $$G_2 = c_{21}H_1 + Z_2 = c_{21}Z_1 + Z_2 = Z_2 = 2x, \quad (209)$$

$$H_2 \frac{2x}{\left[\frac{1}{A}\int_{hexagon} 4x^2 \, dxdy\right]^{1/2}} = \sqrt{6/5}\,(2x) = 1.09545 Z_2$$

Similarly, $$H_3 = \sqrt{6/5}\,(2y) = 1.09545 Z_3, \quad (210)$$
$$c_{41} = 1/\sqrt{3},\ c_{42} = 0 = c_{43},$$
$$G_4 = (1/\sqrt{3})Z_1 + Z_4 = \sqrt{3}\,(2\rho^2 - 5/6),$$

$$H_4 = \frac{\sqrt{3}\,(2\rho^2 - 5/6)}{\left[\frac{1}{A}\int_{hexagon} 3(2\rho^2 - 5/6)^2 \, dxdy\right]^{1/2}} = \frac{\sqrt{3}\,(2\rho^2 - 5/6)}{\sqrt{43/60}}$$

$$= \sqrt{5/43}\,Z_1 + 2\sqrt{15/43}\,Z_4 = 0.34100 Z_1 + 1.18125 Z_4. \quad (211)$$

The other polynomials can be obtained in a similar manner. The first eleven hexagonal polynomials are also listed in Table 7. This table shows orthonormal Zernike circle polynomials $Z_j(x,y)$ in Cartesian coordinates (x,y), where $\rho^2=x^2+y^2$, $0 \leq \rho \leq 1$ for the circle polynomials and (x,y) lie within a unit hexagon for the hexagonal polynomials $H_j(x,y)$.

TABLE 7

| j | $Z_j(x, y)$ | $H_j(x, y)$ | Aberration Name |
|---|---|---|---|
| 1 | 1 | 1 | Piston |
| 2 | 2x | $\sqrt{6/5}\,Z_2$ | x tilt |
| 3 | 2y | $\sqrt{6/5}\,Z_3$ | y tilt |
| 4 | $\sqrt{3}(2\rho^2 - 1)$ | $\sqrt{5/43}\,Z_1 + 2\sqrt{15/43}\,Z_4$ | Defocus |
| 5 | $2\sqrt{6}xy$ | $\sqrt{10/7}\,Z_5$ | Astigmatism at 45° |
| 6 | $\sqrt{6}(x^2 - y^2)$ | $\sqrt{10/7}\,Z_6$ | Astigmatism at 0° |
| 7 | $\sqrt{8}y(3\rho^2 - 2)$ | $16\sqrt{\frac{14}{11055}}\,Z_3 + 10\sqrt{\frac{35}{2211}}\,Z_7$ | y coma |
| 8 | $\sqrt{8}x(3\rho^2 - 2)$ | $16\sqrt{\frac{14}{11055}}\,Z_2 + 10\sqrt{\frac{35}{2211}}\,Z_8$ | x coma |
| 9 | $\sqrt{8}y(3x^2 - y^2)$ | $\frac{2}{3}\sqrt{5}\,Z_9$ | y trefoil |
| 10 | $\sqrt{8}x(x^2 - 3y^2)$ | $2\sqrt{\frac{35}{103}}\,Z_{10}$ | x trefoil |
| 11 | $\sqrt{5}(6\rho^4 - 6\rho^2) + 1)$ | $\frac{521}{\sqrt{1072205}}\,Z_1 + 88\sqrt{\frac{15}{214441}}\,Z_4 + 14\sqrt{\frac{43}{4987}}\,Z_{11}$ | Spherical Aberration |

Table 8 gives the matrix M for obtaining the hexagonal polynomials from the circle polynomials according to Eq. (207). That is, it shows matrix M for obtaining hexagonal polynomials $H_j(x,y)$ from the Zernike circle polynomials $Z_j(x,y)$.

TABLE 8

| 1 | 0 | 0 | 0 | 0 | 0 | 0 | 0 | 0 | 0 | 0 |
|---|---|---|---|---|---|---|---|---|---|---|
| 0 | $\sqrt{6/5}$ | 0 | 0 | 0 | 0 | 0 | 0 | 0 | 0 | 0 |
| 0 | 0 | $\sqrt{6/5}$ | 0 | 0 | 0 | 0 | 0 | 0 | 0 | 0 |
| $\sqrt{5/43}$ | 0 | 0 | $2\sqrt{15/43}$ | 0 | 0 | 0 | 0 | 0 | 0 | 0 |
| 0 | 0 | 0 | 0 | $\sqrt{10/7}$ | 0 | 0 | 0 | 0 | 0 | 0 |
| 0 | 0 | 0 | 0 | 0 | $\sqrt{10/7}$ | 0 | 0 | 0 | 0 | 0 |
| 0 | 0 | $16\sqrt{\frac{14}{11055}}$ | 0 | 0 | 0 | $10\sqrt{\frac{35}{2211}}$ | 0 | 0 | 0 | 0 |

TABLE 8-continued

| | | | | | | | | | | | |
|---|---|---|---|---|---|---|---|---|---|---|---|
| 0 | $16\sqrt{\dfrac{14}{11055}}$ | 0 | 0 | 0 | 0 | 0 | $10\sqrt{\dfrac{35}{2211}}$ | 0 | 0 | 0 |
| 0 | 0 | 0 | 0 | 0 | 0 | 0 | 0 | $\dfrac{2}{3}\sqrt{5}$ | 0 | 0 |
| 0 | 0 | 0 | 0 | 0 | 0 | 0 | 0 | 0 | $2\sqrt{\dfrac{35}{103}}$ | 0 |
| $\dfrac{521}{\sqrt{1072207}}$ | 0 | 0 | $88\sqrt{\dfrac{15}{214441}}$ | 0 | 0 | 0 | 0 | 0 | 0 | $14\sqrt{\dfrac{43}{4987}}$ |

The polar form of Zernike polynomials and the Cartesian and polar form of the hexagonal polynomials are given in Table 9. This table shows Zernike circle polynomials in polar coordinates and hexagonal polynomials in Cartesian and polar coordinates, where $(x,y) = \rho(\cos\theta, \sin\theta)$. The peak-to-valley values for the Zernike and the hexagonal polynomials are also given in this table, where the first number is for the Zernike polynomial and the second number is for the hexagonal. In the case of $Z_{11}$, the aberration starts at a value of $-\sqrt{5}/2$, decreases to zero, reaches a negative value of $-\sqrt{5}/2$, and then increases to $-\sqrt{5}/2$. Hence, the, total number of fringes is equal to 6.7.

TABLE 9

| j | $Z_j(x, y)$ | $H_j(x, y)$ | P-V Value |
|---|---|---|---|
| 1 | 1 | 1 | Not applicable |
| 2 | $2\rho\cos\theta$ | $2\sqrt{6/5}\rho\cos\theta = 2\sqrt{6/5}x$ | 4: $4\sqrt{6/5}$ |
| 3 | $2\rho\sin\theta$ | $2\sqrt{6/5}\rho\sin\theta = 2\sqrt{6/5}y$ | 4: $4\sqrt{6/5}$ |
| 4 | $\sqrt{3}(2\rho^2 - 1)$ | $\sqrt{5/43}(12\rho^2 - 5)$ | $2\sqrt{3}$: $12\sqrt{5/43}$ |
| 5 | $\sqrt{6}\rho^2 \sin 2\theta$ | $2\sqrt{15/7}\rho^2 \sin 2\theta = 4\sqrt{15/7}xy$ | $2\sqrt{6}$: $4\sqrt{15/7}$ |
| 6 | $\sqrt{6}\rho^2 \cos 2\theta$ | $2\sqrt{15/7}\rho^2 \cos 2\theta = 2\sqrt{15/7}(x^2 - y^2)$ | $2\sqrt{6}$: $4\sqrt{15/7}$ |
| 7 | $\sqrt{8}(3\rho^3 - 2\rho)\sin\theta$ | $24\sqrt{42/3685}(25\rho^3 - 14\rho)\sin\theta = 24\sqrt{42/3685}y(25\rho^2 - 14)$ | $2\sqrt{8}$: |
| 8 | $\sqrt{8}(3\rho^3 - 2\rho)\cos\theta$ | $24\sqrt{42/3685}(25\rho^3 - 14\rho)\cos\theta = 24\sqrt{42/3685}x(25\rho^2 - 14)$ | $2\sqrt{8}$: |
| 9 | $\sqrt{8}\rho^3 \sin 3\theta$ | $(4/3)\sqrt{10}\rho^3 \sin 3\theta = (4/3)\sqrt{10}y(3x^2 - y^2)$ | $2\sqrt{8}$: $8\sqrt{70/103}$ |
| 10 | $\sqrt{8}\rho^3 \cos 3\theta$ | $4\sqrt{70/103}\rho^3 \cos 3\theta = 4\sqrt{70/103}x(x^2 - 3y^2)$ | $2\sqrt{8}$: $8\sqrt{70/103}$ |
| 11 | $\sqrt{5}(6\rho^4 - 6\rho^2 + 1)$ | $(3/\sqrt{1072205})(6020\rho^4 - 5140\rho^2 + 737)$ | $3\sqrt{5}$: |

Figure 30:
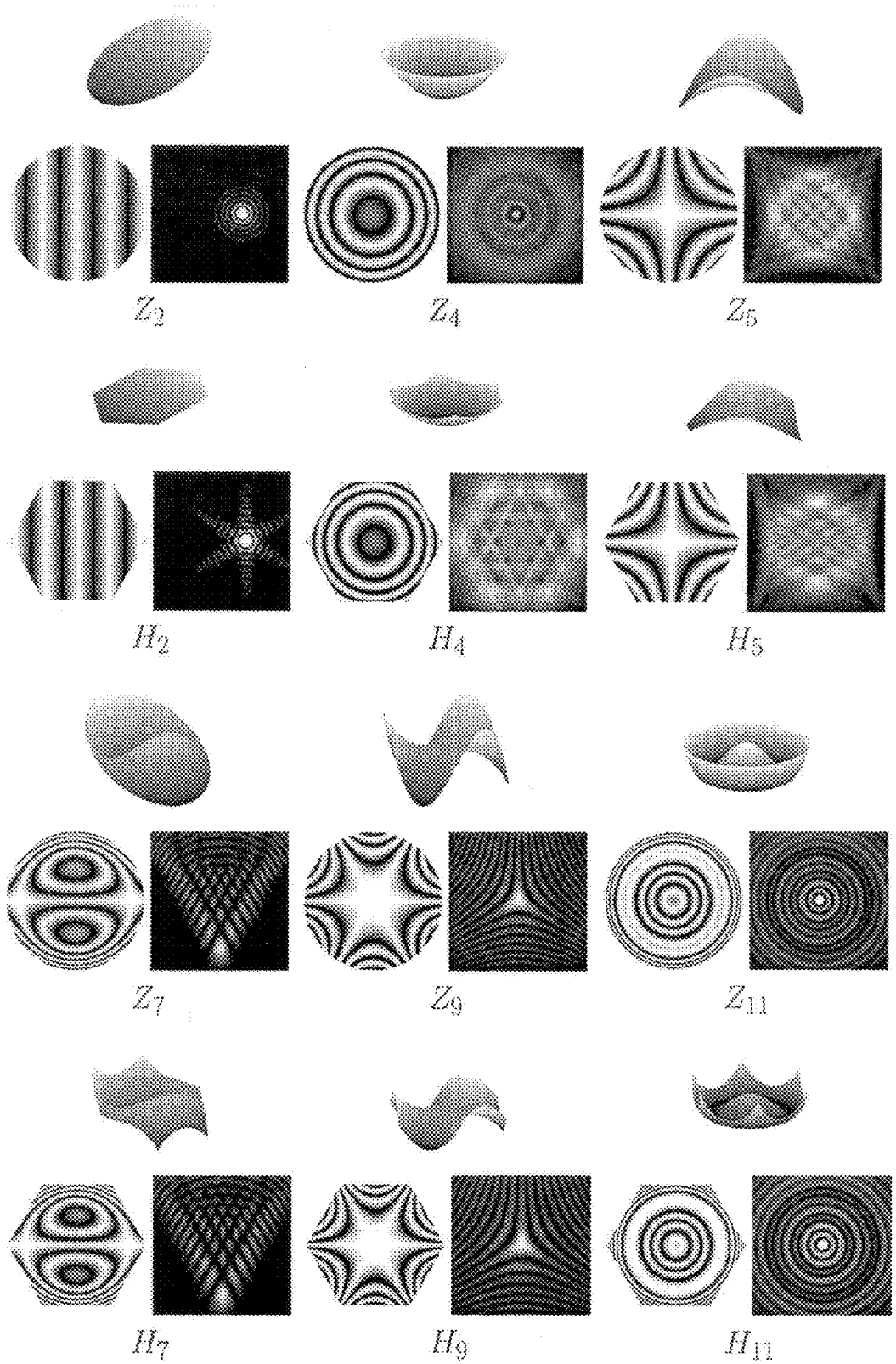
FIG. 30 illustrates isometric, interferometric, and PSF plots of orthonormal hexagonal and circle polynomials according to one embodiment of the present invention.

The isometric, interferometric, and PSF plots of the orthonormal hexagonal and circle polynomials with j=2, 4, 5, 7, 9, and 11, representing x tilt, defocus, astigmatism, coma, trefoil, and spherical aberration, are shown in FIG. 30 for a standard deviation of one wave. For each polynomial, the isometric plot at the top illustrates its shape as produced in a deformable mirror. An interferogram, as in optical testing, is shown on the left. Because, for a given value of a standard deviation, the peak-to-valley value for a hexagonal polynomial is somewhat larger than that for a corresponding circle polynomial, the hexagonal interferogram has somewhat larger number of fringes. The PSF (point-spread function) on the right shows the image of a point object in the presence of a polynomial aberration. The PSFs illustrate their visual appearance. In some cases, more light has been introduced to display their details.

Zernike circle polynomials represent optimally balanced aberrations for minimum variance for systems with circular pupils. See V. N. Mahajan, *Optical Imaging and Aberrations, Part II: Wave Diffraction Optics*, SPIE Press, Bellingham, Wash. (Second Printing 2004); M. Born and E. Wolf, *Principles of Optics*, 7th ed., Oxford, New York (1999); and V. N. Mahajan, "Zernike polynomials and aberration balancing," *SPIE Proc*. Vol 5173, 1-17 (2003). Similarly, the hexagonal polynomials also represent optimally balanced aberrations but for systems with hexagonal pupils. Thus, $H_5$ and $H_6$ represent optimal balancing of Seidel astigmatism with defocus, $H_7$ and $H_8$ represent optimal balancing of Seidel coma with tilt, and $H_{11}$ represents optimal balancing of Seidel spherical aberration with defocus. Strictly speaking, only $H_6$ and $H_8$ represent the balanced Seidel aberrations. However, if (x,y) axes are rotated by $\pi/4$, $H_5$ transforms into $H_6$. Similarly, when the axes are rotated by $\pi/2$, $H_7$ transforms into $H_8$. Hence, $H_5$ and $H_7$ can also be referred to as the balanced Seidel aberrations. The piston term in $H_4$ and $H_{11}$ makes their mean value zero. It is seen from Table 9 that the amount balancing defocus is independent of the shape of the pupil in the case of astigmatism, but its value is smaller for a hexagonal pupil compared to that for a circular pupil in the case of spherical aberration.

To determine the Zernike coefficients of a hexagonal aberration function, it is possible to write in the form $$W(x, y) = \sum_{j=1}^{11} b_j Z_j(x, y), \tag{212}$$

where $b_j$ are the coefficients and we have represented the function by eleven polynomials. Substituting Eq. (207) into Eq. (201), $$W(x, y) = \sum_{j=1}^{11} a_j \sum_{i=1}^{j} M_{ji} Z_i(x, y) \tag{213}$$

$$= \sum_{j=1}^{11} \sum_{i=j}^{11} a_i M_{ij} Z_j(x, y).$$

Comparing Eqs. (212) and (213), $$b_j = \sum_{i=j}^{11} a_i M_{ij}. \tag{214}$$

Because the matrix elements above the diagonal are zero, $b_j=a_jM_{jj}$. Thus, for example, $b_{11}=a_{11}M_{11,11}=\sqrt{43/4987}a_{11}=1.3a_{11}$. It should be evident that the hexagonal coefficients $a_j$ are independent of the number of polynomials used in the expansion of an aberration function. See Eq. (204). This is not true of the Zernike coefficients $b_j$, because the Zernike circle polynomials are not orthogonal over the hexagonal pupil.

Closed-form expressions for the polynomials that are orthonormal over a hexagonal pupil represent balanced classical aberrations, such as for the hexagonal segments of the primary mirror of the Keck telescope. These polynomials are the hexagonal analog of the well known Zernike circle polynomials. The differences between the circle and hexagonal polynomials are illustrated by isometric, interferometric, and PSF plots.

Hexagonal polynomials have properties similar to those of the Zernike polynomials, except that their domain is a unit hexagon instead of a unit circle. Thus, just as the mean value of a Zernike polynomial (except piston $Z_1$) across a unit circle is zero, similarly, the mean value of a hexagonal polynomial across a unit hexagon is also zero. Similarly, for example, just as $Z_{11}$ represents the balanced spherical aberration for a circular pupil, $H_{11}$ represents it for a hexagonal pupil. The coefficient of a polynomial in the expansion of an aberration function represents the standard deviation in each case. Although the Zernike coefficients of an aberration function for a hexagonal pupil can be obtained, the aberration variance can not be obtained by summing the sum of their squares. The variance is equal to the sum of the squares of the coefficients of the hexagonal polynomials (excluding the piston coefficient).

Figure 31:
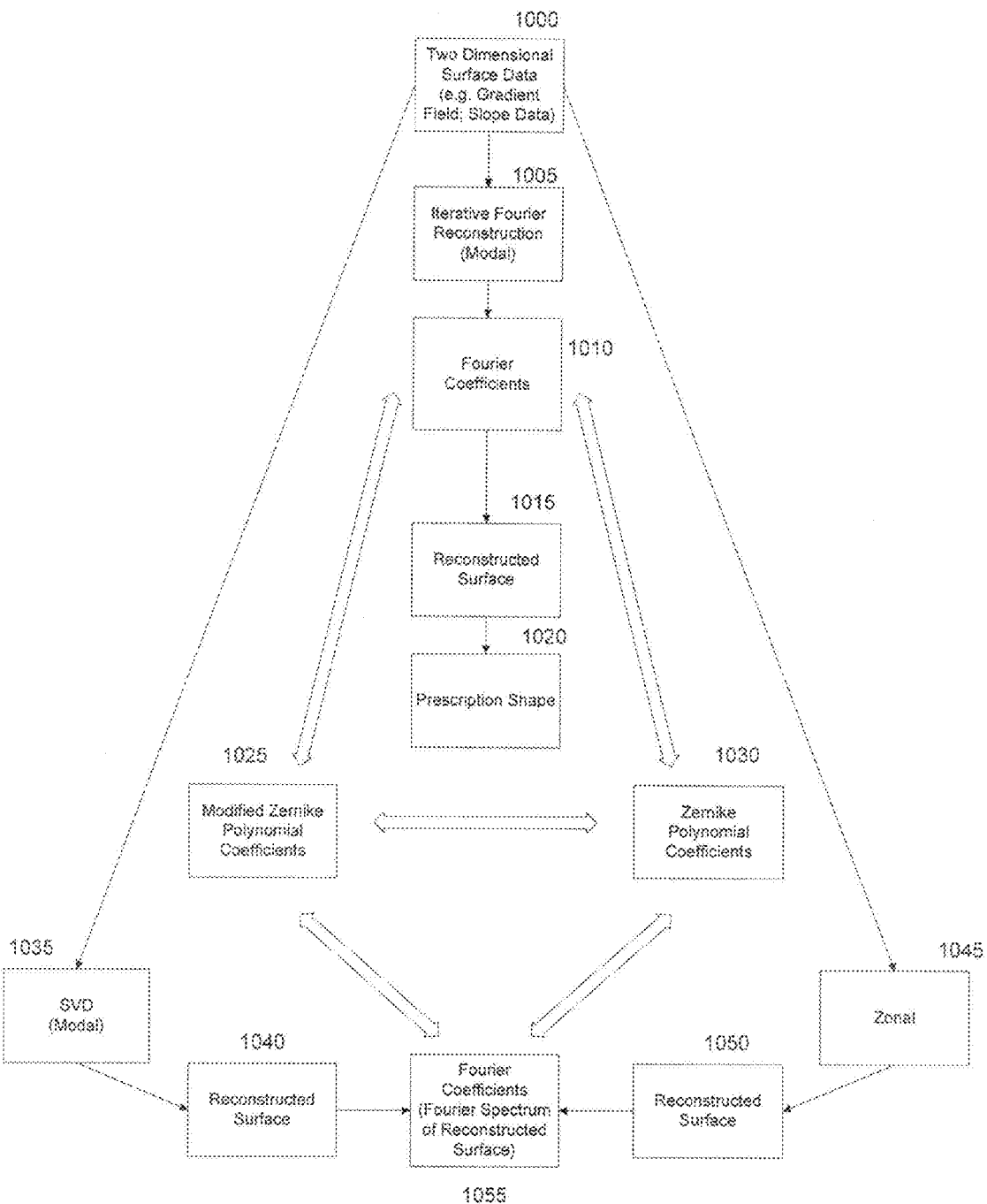
FIG. 31 provides an exemplary data flow chart according to one embodiment of the present invention.

FIG. 31 illustrates an exemplary flow chart for method embodiments. For instance, an exemplary method may include inputting or accepting two dimensional surface data, such as gradient field data or slope data, as indicated by step 1000. The method may also include performing an iterative Fourier reconstruction procedure (modal) on the data, as indicated in step 1005, to obtain a set of Fourier coefficients which correspond to the two dimensional surface data, as indicated by step 1010. As shown by step 1015, the method may also include establishing a reconstructed surface based on the set of Fourier coefficients. Further, as indicated by step 1020, the method may include establishing a prescription shape based on the reconstructed surface.

In some embodiments, an exemplary method may include inputting or accepting two dimensional surface data, such as gradient field data or slope data, as indicated by step 1000. The method may also include performing a singular value decomposition (SVD) procedure (modal) on the data, as indicated in step 1035, to determine a reconstructed surface, as indicated in step 1040. As shown by step 1055, the method may also include establishing a set of Fourier coefficients (e.g. Fourier spectrum of reconstructed surface) based on the reconstructed surface of step 1040. In some embodiments, an exemplary method may include inputting or accepting two dimensional surface data, such as gradient field data or slope data, as indicated by step 1000. The method may also include performing a zonal procedure on the data, as indicated in step 1045, to determine a reconstructed surface, as indicated in step 1050. As shown by step 1055, the method may also include establishing a set of Fourier coefficients (e.g. Fourier spectrum of reconstructed surface) based on the reconstructed surface of step 1050.

Step 1025 indicates that a set of modified Zernike polynomial coefficients can be determined based on the Fourier coefficients of step 1055. Similarly, step 1030 indicates that a set of Zernike polynomial coefficients can be determined based on the Fourier coefficients of step 1055. As seen in FIG. 31, it is possible to establish the set of Fourier coefficients (e.g. Fourier spectrum of reconstructed surface) of step 1055 based on modified Zernike polynomial coefficients of step 1025 or based on Zernike polynomial coefficients of step 1030. It is also possible to determine the set of Zernike polynomial coefficients of step 1030 based on the modified Zernike polynomial coefficients of step 1025, and similarly it is possible to determine the set of modified Zernike polynomial coefficients of step 1025 based on the set of Zernike polynomial coefficients of step 1030. What is more, it is possible to determine a set of Fourier coefficients as indicated in step 1010 based on either the modified Zernike polynomial coefficients of step 1025 or the Zernike polynomial coefficients of step 1030. Likewise, it is possible to determine the set of modified Zernike polynomial coefficients of step 1025, or the set of Zernike polynomial coefficients of step 1030, based on the Fourier coefficients of step 1010. It is clear that any of a variety of paths as shown in FIG. 31 may be taken to reach the set of Fourier coefficients represented at step 1010. Accordingly, method embodiments encompass any suitable or desired route to achieving the prescription shape of step 1020 via the set of Fourier coefficients as seen in step 1010.

Figure 32:
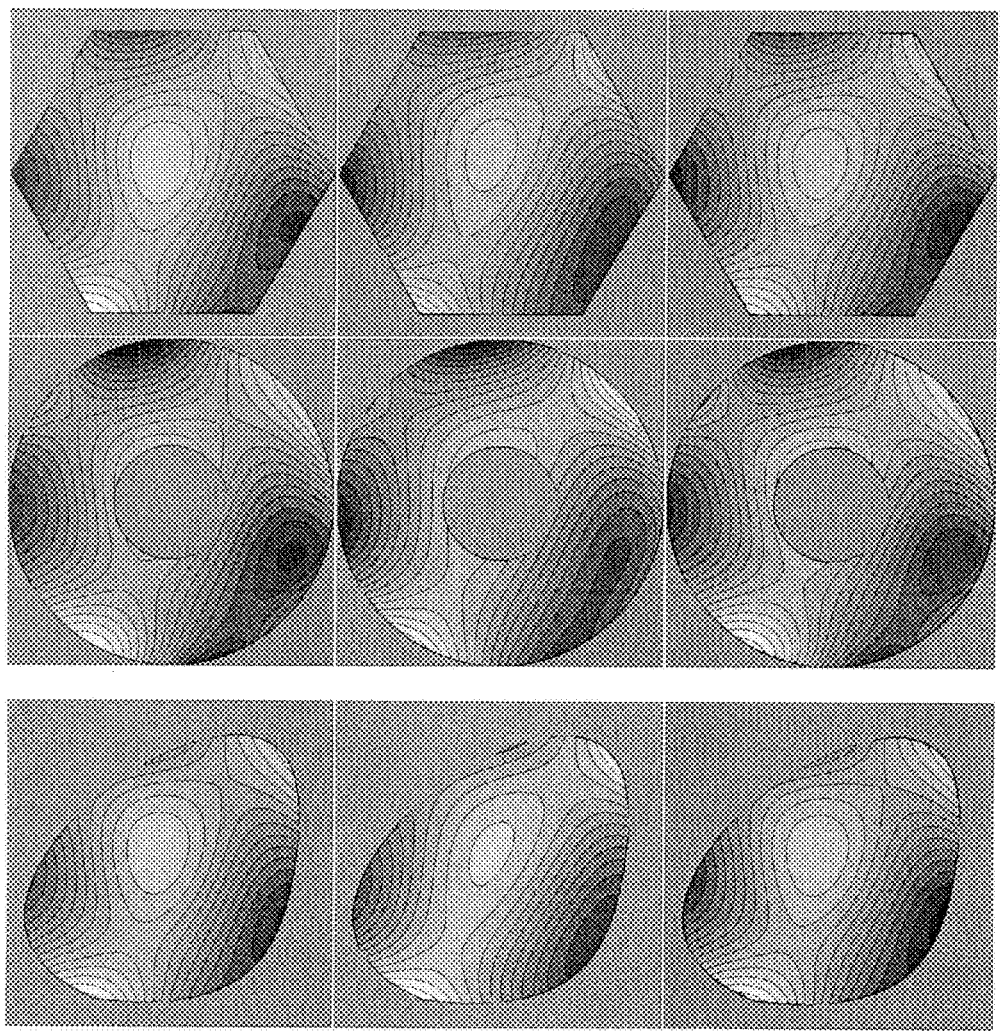
FIG. 32 depicts wavefront reconstruction data according to one embodiment of the present invention.

FIG. 32 depicts the input, SVD reconstructed, and the Fourier reconstructed wavefronts for hexagonal, annular, and irregular apertures, according to some embodiments of the present invention. The illustration provides contour plots for the input (first column), SVD reconstructed (middle column), and Fourier reconstructed (last column) wavefronts, thus showing how a reconstruction algorithm can work.

APPENDIX A

Iterative Fourier reconstruction works well with circular apertures. Zernike coefficients are convertible to and from Fourier coefficients. It would be desirable to have wavefront reconstruction and coefficient conversion for wavefronts with other aperture shapes. Hexagonal and annular apertures are common in adaptive optics, such as deformable mirrors or interferometers. Embodiments of the present invention include analytical and numerical techniques to reconstruct wavefronts of arbitrary shape with iterative Fourier reconstruction and calculate the coefficients of orthonormal basis functions over the aperture from the reconstructed Fourier spectrum.

Wavefront technology has been successfully applied in objective estimation of ocular aberrations with wavefront derivative measurements. Iterative Fourier reconstruction can address the edge effect of Zernike polynomials as well as speed issues. Theoretical and algorithmatical approaches have been demonstrated that Zernike coefficients and Fourier coefficients can be converted to each other. However, in some applications, such as in adaptive optics, aperture shapes or mirror shapes, can be different than circular shape. For example, hexagonal mirrors are commonly used as the deformable mirror in adaptive optics. In addition, in interferometers, aperture sizes are often hexagonal. For many astronomical applications, most telescopes have annular apertures. In vision, people have proposed inlays that effectively use annular apertures. It is desirable to be able to reconstruct a wavefront from slope data using iterative Fourier reconstruction and to convert the Fourier spectrum (coefficients) to coefficients of a set of basis functions that are orthogonal over the apertures of hexagonal or annular, or an arbitrary shape.

Embodiments include formulas to reconstruct wavefront with iterative Fourier transform from slope data and to convert the Fourier spectrum (coefficients) to the coefficients of a set of basis functions that are orthogonal over the aperture over which the slope data are collected.

I. Wavefront Representation

In doing the theoretical derivation, it is useful to discuss the representation of wavefront maps in a pure mathematical means. This will allow mathematical treatment and to relate wavefront expansion coefficients between two different sets of basis functions.

A. General Consideration

Let's consider a wavefront W(x,y) in Cartesian coordinates. It can be shown that the wavefront can be infinitely accurately represented with $$W(x, y) = \sum_{i=0}^{\infty} a_i G_i(x, y), \quad (1a)$$

when the set of basis functions $\{G_i(x,y)\}$ is complete. The completeness of a set of basis functions can mean that for any two sets of complete basis functions, the conversion of coefficients of the two sets always exists.

If the set of basis function $\{G_i(x,y)\}$ is orthogonal over an arbitrary aperture, defined by the aperture function P(x,y), we have $$\iint P(x,y) G_i(x,y) G_{i'}(x,y) dx dy = \delta_{ii'} \quad (2a)$$

where $\delta_{ii'}$ stands for the Kronecker symbol, which equals to 1 only if when i=i'. Multiplying $P(x,y)G_i(x,y)$ in both sides of Eq. (1a), making integrations to the whole space, and with the use of Eq. (2a), the expansion coefficient can be written as $$a_i = \iint P(x,y) W(x,y) G_i(x,y) dx dy. \quad (3a)$$

For other sets of basis functions that are neither complete nor orthogonal, expansion of wavefront may not be accurate. However, even with complete and orthogonal set of basis functions, practical application may not allow wavefront expansion to infinite number, as there may be truncation error. The merit with orthogonal set of basis functions is that the truncation is optimal as it gives minimum root mean squares (RMS) error.

B. Calculation of Zernike Polynomials Over Arbitrary Apertures

Zernike polynomials have long been used as wavefront expansion basis functions mainly because they are complete and orthogonal over circular apertures, and they related to classical aberrations. However, for aperture shapes other than circular, Zernike polynomials are not orthogonal. It is possible to calculate a set of Zernike polynomials (i.e. modified Zernike polynomials) that are orthogonal over apertures of arbitrary shape.

From the Gram-Schmidt orthogonalization (GSO) process, one can write the modified set of Zernike polynomials V as a linear combination of the regular Zernike polynomials as $$V_i = \sum_{m=1}^{n} C_{im} Z_m, \quad (4a)$$

where $Z_m$ is the regular Zernike polynomials and $C_{im}$ is the conversion matrix. Consider the inner product of V and Z as a matrix, defined as $$B_{jl} = \langle U_j, Z_l \rangle \quad (5a)$$

$$= \frac{\int P(x, y) U_j(x, y) Z_l(x, y) dx dy}{\int P(x, y) dx dy}.$$

Matrix C relates to matrix B by $$C = B^{-1}. \quad (6a)$$

Once matrix C is calculated, the modified Zernike polynomials can be calculated using Eqs. (4a)-(6a). Note that calculation of matrix B depends on modified Zernike polynomials V, calculation of V can be done recursively.

C. Fourier Series

Taking the wavefront in Cartesian coordinates in square apertures, represented as W(x,y), we can express the wavefront as a linear combination of sinusoidal functions as $$W(x, y) = \sum_{i=0}^{N^2} c_i F_i(x, y) \quad (7a)$$

$$= \sum_{u=0}^{N-1} \sum_{v=0}^{N-1} c(u, v) \exp\left[j \frac{2\pi}{N}(ux + vy)\right]$$

$$= N \times IFT[c(u, v)]$$

where IFT stands for inverse Fourier transform and $F_i(x,y)$ stands for the Fourier series. It should be noted that Fourier series are complete and orthogonal over rectangular apertures. Representation of Fourier series can be done with single-index or double-index. Conversion between the single-index i and the double-index u and v can be performed with $$u = \begin{cases} i - n^2 & (i - n^2 < n) \\ n & (i - n^2 \geq n), \end{cases} \quad (8a)$$

$$v = \begin{cases} n & (i - n^2 < n) \\ n^2 + 2n - i & (i - n^2 \geq n). \end{cases}$$

where the order n can be calculated with $$n = \begin{cases} \mathrm{int}(\sqrt{i}) \\ \max(u, v) \end{cases} \quad (9a)$$

From Eq. (7a), the coefficients c(u,v) can be written as $$c(u, v) = \sum_{x=0}^{N-1} \sum_{y=0}^{N-1} W(x, y) \exp\left[-j \frac{2\pi}{N}(ux + vy)\right] \quad (10a)$$

$$= \frac{1}{N} \times FT[W(x, y)].$$

where FT stands for Fourier transform.

D. Conversion Between Fourier Coefficients and Modified Zernike Coefficients

Conversion of the coefficients between two complete sets of basis functions often exists. This subsection develops the conversion between modified Zernike coefficients and Fourier coefficients.

Starting from Eq. (3a), if we replace the basis function G(x,y) with modified Zernike polynomials, we have $$a_i = \int_{-\infty}^{\infty}\int_{-\infty}^{\infty} P(x,y)W(x,y)V_i(x,y)dxdy. \qquad (11a)$$

In Eq. (7a), if we set N approach infinity, we get $$W(x,y) = \int_{-\infty}^{\infty}\int_{-\infty}^{\infty} c(x,y)\exp[j2\pi(ux+vy)]dudv. \qquad (12a)$$

Substituting Eq. (12a) into Eq. (11a), we obtain $$\begin{aligned}a_i &= \int_{-\infty}^{\infty}\int_{-\infty}^{\infty} P(x,y)W(x,y)V_i(x,y)dxdy \\ &= \int_{-\infty}^{\infty}\int_{-\infty}^{\infty} P(x,y)\int_{-\infty}^{\infty}\int_{-\infty}^{\infty} c(u,v) \\ &\quad \exp[j2\pi(ux+vy)]dudv\,V_i(x,y)dxdy \\ &= \int_{-\infty}^{\infty}\int_{-\infty}^{\infty} P(x,y)V_i(x,y)\exp[j2\pi(ux+vy)]dxdy \\ &\quad \int_{-\infty}^{\infty}\int_{-\infty}^{\infty} c(u,v)dudv.\end{aligned} \qquad (13a)$$

Notice that the first part is the inverse Fourier transform of modified Zernike polynomials, $$U_i^*(u,v) = \int_{-\infty}^{\infty}\int_{-\infty}^{\infty} P(x,y)V_i(x,y)\exp[j2\pi(ux+vy)]dxdy, \qquad (14a)$$

we can re-write Eq. (13a) as $$a_i = \int_{-\infty}^{\infty}\int_{-\infty}^{\infty} c(u,v)U_i^*(u,v)dudv. \qquad (15a)$$

Written in discrete format, Eq. (15a) can be written as $$a_i = \frac{1}{N^2}\sum_{u=0}^{N-1}\sum_{v=0}^{N-1} c(u,v)U_i^*(u,v). \qquad (16a)$$

Equation (16a) is an answer for calculating the modified Zernike coefficients directly from the Fourier transform of wavefront maps, i.e., it is the average sum, pixel by pixel, in the Fourier domain, the multiplication of the Fourier transform of the wavefront and the inverse Fourier transform of modified Zernike polynomials. Both c(u,v) and $U_i$(u,v) are complex matrices.

II. Wavefront Estimation from Slope Measurements

Wavefront reconstruction from wavefront slope measurements has been discussed extensively in the literature. Reconstruction may include, for example, a zonal approach or a modal approach. In a zonal approach, the wavefront can be estimated directly from a set of discrete phase-slope measurements; whereas in a modal approach, the wavefront can be expanded into a set of orthogonal basis functions and the coefficients of the set of basis functions are estimated from the discrete phase-slope measurements. A modal reconstruction can be performed with iterative Fourier transforms.

Let's start from Eq. (12a) in analytical form $$W(x,y) = \iint c(u,v)\exp[j2\pi(ux+vy)]dudv, \qquad (17a)$$

where c(u,v) is the matrix of expansion coefficients. Taking partial derivative to x and y, respectively, in Equation (17a), we have $$\begin{cases}\dfrac{\partial W(x,y)}{\partial x} = j2\pi\iint uc(u,v)\exp[j2\pi(ux+vy)]dudv \\ \dfrac{\partial W(x,y)}{\partial y} = j2\pi\iint vc(u,v)\exp[j2\pi(ux+vy)]dudv\end{cases} \qquad (18a)$$

Denote $c_u$ to be the Fourier transform of x-derivative of W(x,y) and $c_v$ to be the Fourier transform of y-derivative of W(x,y). From the definition of Fourier transform, we have $$\begin{cases}c_u(u,v) = \iint \dfrac{\partial W(x,y)}{\partial x}\exp[-j2\pi(ux+vy)]dxdy \\ c_v(u,v) = \iint \dfrac{\partial W(x,y)}{\partial y}\exp[-j2\pi(ux+vy)]dxdy\end{cases} \qquad (19a)$$

Equation (19a) can also be written in the inverse Fourier transform format as $$\begin{cases}\dfrac{\partial W(x,y)}{\partial x} = \iint c_u(u,v)\exp[j2\pi(ux+vy)]dudv \\ \dfrac{\partial W(x,y)}{\partial y} = \iint c_v(u,v)\exp[j2\pi(ux+vy)]dudv\end{cases} \qquad (20a)$$

Comparing Equations (18a) and (20a), we obtain $$c_u(u,v) = j2\pi uc(u,v) \qquad (21a)$$

$$c_v(u,v) = j2\pi vc(u,v) \qquad (22a)$$

If we multiple u in both sides of Equation (21a) and v in both sides of Equation (22a) and sum them together, we get $$uc_u(u,v) + vc_v(u,v) = j2\pi(u^2+v^2)c(u,v). \qquad (23a)$$

From Equation (23a), we obtain the Fourier expansion coefficients as $$c(u,v) = -j\frac{uc_u(u,v) + vc_v(u,v)}{2\pi(u^2+v^2)} \qquad (24a)$$

Hence, taking an inverse Fourier transform of Equation (24a), we obtained the wavefront as $$W(x,y) = \iint c(u,v)\exp[j2\pi(ux+vy)]dudv. \qquad (25a)$$

Equation (25a) is a solution for wavefront reconstruction. That is to say, if we know the wavefront slope data, we can calculate the coefficients of Fourier series using Equation (24a). With Equation (25a), the unknown wavefront can then be reconstructed. Because a Hartmann-Shack wavefront sensor can measure a set of local wavefront slopes, the application of Equation (24a) can be used with a Hartmann-Shack approach.

In some cases, this approach of wavefront reconstruction may apply only to unbounded functions. In order to obtain an estimate of wavefront with boundary conditions (aperture with arbitrary shape), an iterative reconstruction approach may be needed. First, we can follow the above approach to do an initial solution, which gives function values to a square grid larger than the function boundary. The local slopes of the estimated wavefront of the entire square grid can then be calculated. In the next step, known local slope data, i.e., the measured gradients from Hartmann-Shack device, can overwrite the calculated slopes. Based on the updated slopes, the above approach can be applied again and a new estimate of wavefront can be obtained. This procedure can be done until either a pre-defined number of iteration is reached or a pre-defined criterion is satisfied.

All patent filings, scientific journals, books, treatises, and other publications and materials discussed in this application are hereby incorporated by reference for all purposes. A variety of modifications are possible within the scope of the present invention. For example, the Fourier-based methods of the present invention may be used in the aforementioned ablation monitoring system feedback system for real-time intrasurgical measurement of a patient's eye during and/or between each laser pulse. The Fourier-based methods are particularly well suited for such use due to their measurement accuracy and high speed. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art. Although the invention has been described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with the current invention. The above systems are available from TRACEY Technologies of Bellaire, Tex., Wavelight of Erlangen, Germany, and Nidek, Inc. of Fremont, Calif., respectively. The invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to refractive laser corneal surgery.

Each of the above calculations may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed. Therefore, the scope of the present invention is limited solely by the claims.

What is claimed is:

1. A system for determining an aberration in an optical tissue system of an eye, the system comprising:
    a light source for transmitting an image through the optical tissue system;
    a sensor oriented for determining a set of local gradients for the optical tissue system by detecting the transmitted image, the set of local gradients corresponding to a non circular shaped aperture;
    a processor coupled with the sensor; and
    a memory coupled with the processor, the memory configured to store a plurality of code modules for execution by the processor, the plurality of code modules comprising:
        a module for inputting optical data from the optical tissue system of the eye, the optical data comprising the set of local gradients;
        a module for processing the optical data with an iterative Fourier transform to obtain a set of Fourier coefficients;
        a module for converting the set of Fourier coefficients to a set of modified Zernike coefficients that are orthogonal over the non-circular shaped aperture; and
        a module for determining the aberration in the optical tissue system of the eye based on the set of modified Zernike coefficients.

2. The system of claim 1, further comprising a module for establishing a prescription shape for the eye based on the aberration.

3. The system of claim 1, wherein the non-circular shaped aperture comprises a hexagonal aperture.

4. The system of claim 1, wherein the non-circular shaped aperture comprises an elliptical aperture.

5. The system of claim 1, wherein the non-circular shaped aperture comprises an annular aperture.

6. The system of claim 1, wherein the optical data comprises Hartmann-Shack wavefront sensor data.

7. The system of claim 1, wherein the module for converting the set of Fourier coefficients to a set of modified Zernike coefficients comprises a Gram-Schmidt orthogonalization module.

8. A system for determining an optical surface model for an optical tissue system of an eye, the system comprising:
    a light source for transmitting an image through the optical tissue system;
    a sensor oriented for determining a set of local gradients for the optical tissue system by detecting the transmitted image, the set of local gradients corresponding to a non-circular shaped aperture;
    a processor coupled with the sensor; and
    a memory coupled with the processor, the memory configured to store a plurality of code modules for execution by the processor, the plurality of code modules comprising:
        a module for inputting optical data from the optical tissue system of the eye, the optical data comprising the set of local gradients;
        a module for processing the optical data with an iterative Fourier transform to obtain a set of Fourier coefficients;
        a module for converting the set of Fourier coefficients to a set of modified Zernike coefficients that are orthogonal over the non-circular shaped aperture;
        a module for deriving a reconstructed surface based on the set of modified Zernike coefficients; and
        a module for determining the optical surface model based on the reconstructed surface.

9. The system of claim 8, further comprising a module for establishing a prescription shape for the eye based on the optical surface model.

10. The system of claim 8, wherein the non-circular shaped aperture comprises a hexagonal aperture.

11. The system of claim 8, wherein the non-circular shaped aperture comprises an elliptical aperture.

12. The system of claim 8, wherein the non-circular shaped aperture comprises an annular aperture.

13. The system of claim 8, wherein the optical data comprises Hartmann-Shack wavefront sensor data.

14. The system of claim 8, wherein the module for converting the set of Fourier coefficients to a set of modified Zernike coefficients comprises a Gram-Schmidt orthogonalization module.

15. A computer program product for determining an aberration in an optical tissue system of an eye, the computer program product comprising:
  code for accepting optical data corresponding to the optical tissue system of the eye, the optical data comprising a set of local gradients corresponding to a non-circular shaped aperture; and
  code for processing the optical data with an iterative Fourier transform to obtain a set of Fourier coefficients;
  code for converting the set of Fourier coefficients to a set of modified Zernike coefficients that are orthogonal over the non-circular shaped aperture;
  code for determining the aberration in the optical tissue system of the eye based on the set of modified Zernike coefficients; and
  a computer-readable medium that stores the codes.

16. The computer program product of claim 15, further comprising code for establishing a prescription shape for the eye based on the optical surface model.

17. The computer program product of claim 15, wherein the non-circular shaped aperture comprises a hexagonal aperture.

18. The computer program product of claim 15, wherein the non-circular shaped aperture comprises an elliptical aperture.

19. The computer program product of claim 15, wherein the non-circular shaped aperture comprises an annular aperture.

20. The computer program product of claim 15, wherein the optical data comprises Hartmann-Shack wavefront sensor data.

* * * * *